US012281363B2

(12) United States Patent
Mbisa

(10) Patent No.: US 12,281,363 B2
(45) Date of Patent: Apr. 22, 2025

(54) METHODS FOR DETECTING ANTIVIRAL-DRUG RESISTANT VIRUS

(71) Applicant: Secretary of State for Health and Social Care, London (GB)

(72) Inventor: Jean Lutamyo Mbisa, London (GB)

(73) Assignee: Secretary of State for Health and Social Care, London (GB)

( * ) Notice: Subject to any disclaimer, the term of this patent is extended or adjusted under 35 U.S.C. 154(b) by 1137 days.

(21) Appl. No.: 15/734,910

(22) PCT Filed: Jun. 4, 2019

(86) PCT No.: PCT/GB2019/051546
§ 371 (c)(1),
(2) Date: Dec. 3, 2020

(87) PCT Pub. No.: WO2019/234413
PCT Pub. Date: Dec. 12, 2019

(65) Prior Publication Data
US 2021/0230710 A1 Jul. 29, 2021

(30) Foreign Application Priority Data
Jun. 4, 2018 (GB) ..................................... 1809135

(51) Int. Cl.
*C12Q 1/68* (2018.01)
*C12Q 1/70* (2006.01)
*G01N 33/569* (2006.01)

(52) U.S. Cl.
CPC ....... *C12Q 1/705* (2013.01); *G01N 33/56994* (2013.01); *C12Q 2600/106* (2013.01); *C12Q 2600/156* (2013.01); *G01N 2800/52* (2013.01)

(58) Field of Classification Search
None
See application file for complete search history.

(56) References Cited

U.S. PATENT DOCUMENTS

2016/0089372 A1 3/2016 Clifford et al.

OTHER PUBLICATIONS

Sauerbrei et al; J Antimicrob Chemother; 2016, 71:6-16.*
Afshar, B., et al., "A European Multi-Centre External Quality Assessment (EQA) Study on Phenotypic and Genotypic Methods Used for Herpes Simplex Virus (HSV) Drug Resistance Testing," Journal of Clinical Virology 96:89-93, Nov. 2017.
Brunnemann, A-K., et al., "Relevance of Non-Synonymous Thymidine Kinase Mutations for Antiviral Resistance of Recombinant Herpes Simplex Virus Type 2 Strains," Antiviral Research 152:53-57, Feb. 2018.
Gilbert, C., et al., "Resistance of Herpesviruses to Antiviral Drugs: Clinical Impacts and Molecular Mechanisms," Drug Resistance Updates 5(2):88-114, Apr. 2002.
Frobert, E., et al., "Genotypic Detection of Acyclovir-Resistant HSV-1: Characterization of 67 ACV-Sensitive and 14 ACV-Resistant Viruses," Antiviral Research, 79:28-36, Feb. 2008.
Frobert, E., et al., "Genotyping Diagnosis of Acyclovir Resistant Herpes Simplex Virus," 55(10):504-511, Oct. 2007.
International Search Report and Written Opinion mailed Sep. 11, 2019, issued in corresponding Application No. PCT/GB2019/051546, filed Jun. 4, 2019, 18 pages.
International Preliminary Report on Patentability mailed Sep. 17, 2020, issued in corresponding Application No. PCT/GB2019/051546, filed Jun. 4, 2019, 28 pages.
Kaspar, M., et al., "Stepwise Characterization of Non-Synonymous Mutations in the HSV-1 Thymidine Kinase Gene by Different Functional Assays," Journal of Virological Methods, 247:51-57, May 2017.
Sauerbei, A., et al., "Database on Natural Polymorphisms and Resistance-Related Non-Synonymous Mutations in Thymidine Kinase and DNA Polymerase Genes of Herpes Simplex Virus Types 1 and 2," Journal of Antimicrobial Chemotherapy 71:6-16, 2016.
Second Written Opinion mailed May 27, 2020, issued in corresponding Application No. PCT/GB2019/051546, filed Jun. 4, 2019, 7 pages.
Search Report mailed Jan. 31, 2019, issued in corresponding Application No. GB1809135.5, filed Jun. 4, 2018, 4 pages.
Notice of Reasons for Rejection mailed Jun. 9, 2023, issued in corresponding Japanese Application No. 2020-563927, filed Jun. 4, 2019, 11 pages.
Hussin, A., et al., "Phenotypic and genotypic characterization of induced acyclovir-resistant clinical isolates of herpes simplex virus type 1," Antiviral Research 100 (2013): 306-313.
Topalis, D., et al., "Thymidine kinase and protein kinase in drug-resistant herpesviruses: Heads of a Lernaean Hydra," Drug Resistance Updates 37 (2018): 1-16.
Burrel, S., et al., "Surveillance of herpes simplex virus resistance to antivirals: A 4-year survey," Antiviral Research 100:365-372, 2013.
Piret, J., and G. Boivin, "Antiviral drug resistance in herpesviruses other than cytomegalovirus," Reviews in Medical Virology 24:186-218, 2014.

(Continued)

*Primary Examiner* — Jehanne S Sitton
(74) *Attorney, Agent, or Firm* — Christensen O'Connor Johnson Kindness PLLC

(57) ABSTRACT

The present invention is directed to a method for detecting the presence or absence of an antiviral drug-resistant HSV, comprising: (a) identifying one or more HSV mutation selected from: (i) a thymidine kinase (TK) mutation selected from 250G>A (HSV-2), 0C>T (HSV-1), 268C>T (HSV-2), 373C>T (HSV-1), 146T>G (HSV-1), 363G>A (HSV-), 497T>A (HSV-1), 558G>T (HSV-2), 641A>G (HSV-2), 715T>C (HSV-1), 938T>C(HSV-2), 437_438insA (HSV-1), 169delC (HSV-1), 170delC (HSV-1), 171delC (HSV-1), 1072delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1); and (ii) a DNA polymerase (DNA pol) mutation selected from 1882C>G(HSV-2), 2405T>G (HSV-1), 2500G>T (HSV-1), 2515A>G (HSV-1), 2892_2893insT (HSV-1), 2893_2894insT (HSV-1), 2894_2895insT (HSV-1), and 2895_2896insT (HSV-1); wherein the presence of said one or more HSV mutation confirms the presence of an antiviral drug-resistant HSV, and wherein the absence of said one or more HSV mutation is indicative of the absence of an antiviral drug-resistant HSV.

6 Claims, 6 Drawing Sheets

Specification includes a Sequence Listing.

(56) References Cited

OTHER PUBLICATIONS

Piret, J., and G. Boivin, "Resistance of Herpes Simplex Viruses to Nucleoside Analogues: Mechanisms, Prevalence, and Management," Antimicrobial Agents and Chemotherapy 55(2):459-472, Feb. 2011.
Examination Communication mailed Jan. 10, 2024, issued in corresponding European Application No. 19730900.8, filed Jun. 4, 2019, 8 pages.
Decision of Rejection mailed Dec. 5, 2023, issued in corresponding Japanese Application No. 2020-563927, filed Jun. 4, 2019, 7 pages.
Dunnen, J.T.D., et al., "Nomenclature for the Description of Human Sequence Variations," Human and Clinical Genetics, 109:121-124, 2001.
Mbisa, J.L., "Antiviral Resistance Testing," John Wiley & Sons, Ltd., pp. 1-12, 2013.

* cited by examiner

SEQUENCE LISTING

<160> NUMBER OF SEQ ID NOS: 8

<210> SEQ ID NO 1
<211> LENGTH: 1131
<212> TYPE: DNA
<213> ORGANISM: Herpes simplex virus 1

<400> SEQUENCE: 1
atggcttcgt acccctgcca tcaacacgcg tctgcgttcg accaggctgc gcgttctcgc 60
ggccataaca accgacgtac ggcgttgcgc cctcgccggc agcaaaaagc cacggaagtc 120
cgcctggagc agaaaatgcc cacgctactg cgggtttata tagacggtcc ccacgggatg 180
gggaaaacca ccaccacgca actgctggtg gccctgggtt cgcgcgacga tatcgtctac 240
gtacccgagc cgatgactta ctggcgggtg ttgggggctt ccgagacaat cgcgaacatc 300
tacaccacac aacaccgcct cgaccagggt gagatatcgg ccggggacgc ggcggtggta 360
atgacaagcg cccagataac aatgggcatg ccttatgccg tgaccgacgc cgttctggct 420
cctcatatcg gggggaggc tgggagctca catgccccgc ccccggccct caccctcatc 480
ttcgaccgcc atcccatcgc cgccctcctg tgctacccgg ccgcgcgata ccttatgggc 540
agcatgaccc cccaggccgt gctggcgttc gtggccctca tcccgccgac cttgcccggc 600
acaaacatcg tgttgggggc ccttccggag gacagacaca tcgaccgcct ggccaaacgc 660
cagcgccccg gcgagcggct tgacctggct atgctggccg cgattcgccg cgtttatggg 720
ctgcttgcca atacggtgcg gtatctgcag ggcggcgggt cgtggcggga ggattgggga 780
cagctttcgg gggcggccgt gccgccccag ggtgccgagc cccagagcaa cgcgggccca 840
cgaccccata tcggggacac gttatttacc ctgtttcggg cccccgagtt gctggccccc 900
aacggcgacc tgtataacgt gtttgcctgg gctttggacg tcttggccaa acgcctccgt 960
cccatgcacg tctttatcct ggattacgac caatcgcccg ccggctgccg ggacgccctg 1020
ctgcaactta cctccgggat ggtccagacc cacgtcacca ccccaggctc cataccgacg 1080
atctgcgacc tggcgcgcac gtttgcccgg gagatggggg aggctaactg a 1131

<210> SEQ ID NO 2
<211> LENGTH: 376
<212> TYPE: PRT
<213> ORGANISM: Herpes simplex virus 1

<400> SEQUENCE: 2

Met Ala Ser Tyr Pro Cys His Gln His Ala Ser Ala Phe Asp Gln Ala
1 5 10 15

Ala Arg Ser Arg Gly His Asn Asn Arg Arg Thr Ala Leu Arg Pro Arg
20 25 30

Arg Gln Gln Lys Ala Thr Glu Val Arg Leu Glu Gln Lys Met Pro Thr
35 40 45

Leu Leu Arg Val Tyr Ile Asp Gly Pro His Gly Met Gly Lys Thr Thr
50 55 60

Thr Thr Gln Leu Leu Val Ala Leu Gly Ser Arg Asp Asp Ile Val Tyr
65 70 75 80

Val Pro Glu Pro Met Thr Tyr Trp Arg Val Leu Gly Ala Ser Glu Thr
85 90 95

Ile Ala Asn Ile Tyr Thr Thr Gln His Arg Leu Asp Gln Gly Glu Ile
100 105 110

Ser Ala Gly Asp Ala Ala Val Val Met Thr Ser Ala Gln Ile Thr Met
115 120 125

```
Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Arg
                245                 250                 255

Glu Asp Trp Gly Gln Leu Ser Gly Ala Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375
```

<210> SEQ ID NO 3
<211> LENGTH: 3747
<212> TYPE: DNA
<213> ORGANISM: Herpes simplex virus 1

<400> SEQUENCE: 3

```
atgttttccg gtggcggcgg cccgctgtcc cccggaggaa agtcggcggc cagggcggcg      60

tccgggtttt ttgcgcccgc cggccctcgc ggagccagcc ggggaccccc gccttgtttg     120

aggcaaaact tttacaaccc ctacctcgcc ccagtcggga cgcaacagaa gccgaccggg     180

ccaacccagc gccatacgta ctatagcgaa tgcgatgaat ttcgattcat cgccccgcgg     240

gtgctggacg aggatgcccc cccggagaag cgcgccgggg tgcacgacgg tcacctcaag     300

cgcgccccca aggtgtactg cgggggggac gagcgcgacg tcctccgcgt cgggtcgggc     360

ggcttctggc cgcggcgctc gcgcctgtgg ggcggcgtgg accacgcccc ggcggggttc     420

aaccccaccg tcaccgtctt tcacgtgtac gacatcctgg agaacgtgga gcacgcgtac     480

ggcatgcgcg cggcccagtt ccacgcgcgg tttatggacg ccatcacacc gacggggacc     540

gtcatcacgc tcctgggcct gactccggaa ggccaccggg tggccgttca cgtttacggc     600

acgcggcagt acttttacat gaacaaggag gaggtcgaca ggcacctaca atgccgcgcc     660
```

-continued

```
ccacgagatc tctgcgagcg catggccgcg gccctgcgcg agtccccggg cgcgtcgttc    720
cgcggcatct ccgcggacca cttcgaggcg gaggtggtgg agcgcaccga cgtgtactac    780
tacgagacgc gccccgctct gttttaccgc gtctacgtcc gaagcgggcg cgtgctgtcg    840
tacctgtgcg acaacttctg cccggccatc aagaagtacg agggtggggt cgacgccacc    900
acccggttca tcctggacaa ccccgggttc gtcaccttcg gctggtaccg tctcaaaccg    960
ggccggaaca acacgctagc ccagccgcgg gccccgatgg ccttcgggac atccagcgac   1020
gtcgagttta actgtacggc ggacaacctg gccatcgagg ggggcatgag cgacctaccg   1080
gcatacaagc tcatgtgctt cgatatcgaa tgcaaggcgg ggggggagga cgagctggcc   1140
tttccggtgg ccgggcaccc ggaggacctg gtcatccaga tatcctgtct gctctacgac   1200
ctgtccacca ccgccctgga gcacgtcctc ctgttttcgc tcggttcctg cgacctcccc   1260
gaatcccacc tgaacgagct ggcggccagg ggcctgccca cgcccgtggt tctggaattc   1320
gacagcgaat tcgagatgct gttggccttc atgacccttg tgaaacagta cggccccgag   1380
ttcgtgaccg ggtacaacat catcaacttc gactggccct tcttgctggc caagctgacg   1440
gacatttaca aggtccccct ggacgggtac ggccgcatga acggccgggg cgtgtttcgc   1500
gtgtgggaca taggccagag ccacttccag aagcgcagca agataaaggt gaacggcatg   1560
gtgaacatcg acatgtacgg gattataacc gacaagatca agctctcgag ctacaagctc   1620
aacgccgtgg ccgaagccgt cctgaaggac aagaagaagg acctgagcta tcgcgacatc   1680
cccgcctact acgccgccgg gcccgcgcaa cgcggggtga tcggcgagta ctgcatacag   1740
gattccctgc tggtgggcca gctgtttttt aagtttttgc cccatctgga gctctcggcc   1800
gtcgcgcgct tggcgggtat taacatcacc cgcaccatct acgacggcca gcagatccgc   1860
gtctttacgt gcctgctgcg cctggccgac cagaagggct ttattctgcc ggacacccag   1920
gggcgattta ggggcgccgg gggggaggcg cccaagcgtc cggccgcagc ccgggaggac   1980
gaggagcggc cagaggagga gggggaggac gaggacgaac gcgaggaggg cgggggcgag   2040
cgggagccgg agggcgcgcg ggagaccgcc ggcaggcacg tggggtacca gggggccagg   2100
gtccttgacc ccacttccgg gtttcacgtg aaccccgtgg tggtgttcga ctttgccagc   2160
ctgtacccca gcatcatcca ggcccacaac ctgtgcttca gcacgctctc cctgagggcc   2220
gacgcagtgg cgcacctgga ggcgggcaag gactacctgg agatcgaggt gggggggcga   2280
cggctgttct tcgtcaaggc tcacgtgcga gagagcctcc tcagcatcct cctgcgggac   2340
tggctcgcca tgcgaaagca gatccgctcg cggattcccc agagcagccc cgaggaggcc   2400
gtgctcctgg acaagcagca ggccgccatc aaggtcgtgt gtaactcggt gtacgggttc   2460
acgggagtgc agcacggact cctgccgtgc ctgcacgttg ccgcgacggt gacgaccatc   2520
ggccgcgaga tgctgctcgc gacccgcgag tacgtccacg cgcgctgggc ggccttcgaa   2580
cagctcctgg ccgatttccc ggaggcggcc gacatgcgcg cccccgggcc ctattccatg   2640
cgcatcatct acggggacac ggactccatc tttgtgctgt gccgcggcct cacggccgcc   2700
gggctgacgg ccgtgggcga caagatggcg agccacatct cgcgcgcgct gtttctgccc   2760
cccatcaaac tcgagtgcga aaagacgttc accaagctgc tgctgatcgc caagaaaaag   2820
tacatcggcg tcatctacgg gggtaagatg ctcatcaagg gcgtggatct ggtgcgcaaa   2880
aacaactgcg cgtttatcaa ccgcacctcc agggccctgg tcgacctgct gttttacgac   2940
gataccgtct ccggagcggc cgccgcgtta gccgagcgcc ccgcggagga gtggctggcg   3000
cgacccctgc ccgagggact gcaggcgttc ggggccgtcc tcgtagacgc ccatcggcgc   3060
```

-continued

```
atcaccgacc cggagaggga catccaggac tttgtcctca ccgccgaact gagcagacac   3120

ccgcgcgcgt acaccaacaa gcgcctggcc cacctgacgg tgtattacaa gctcatggcc   3180

cgccgcgcgc aggtcccgtc catcaaggac cggatcccgt acgtgatcgt ggcccagacc   3240

cgcgaggtag aggagacggt cgcgcggctg gccgccctcc gcgagctaga cgccgccgcc   3300

ccaggggacg agcccgcccc ccccgcggcc ctgccctccc cggccaagcg cccccgggag   3360

acgccgtcgc ctgccgaccc cccgggaggc gcgtccaagc cccgcaagct gctggtgtcc   3420

gagctggccg aggatcccgc atacgccatt gcccacggcg tcgccctgaa cacggactat   3480

tacttctccc acctgttggg ggcggcgtgc gtgacattca aggccctgtt tgggaataac   3540

gccaagatca ccgagagtct gttaaaaagg tttattcccg aagtgtggca ccccccggac   3600

gacgtggccg cgcggctccg gaccgcaggg ttcggggcgg tgggtgccgg cgctacggcg   3660

gaggaaactc gtcgaatgtt gcatagagcc tttgatactc tagcatgagc cccccgtcga   3720

agctgatgtc cctcatttta caataaa                                       3747
```

<210> SEQ ID NO 4
<211> LENGTH: 1235
<212> TYPE: PRT
<213> ORGANISM: Herpes simplex virus 1

<400> SEQUENCE: 4

```
Met Phe Ser Gly Gly Gly Gly Pro Leu Ser Pro Gly Gly Lys Ser Ala
1               5                   10                  15

Ala Arg Ala Ala Ser Gly Phe Phe Ala Pro Ala Gly Pro Arg Gly Ala
            20                  25                  30

Ser Arg Gly Pro Pro Pro Cys Leu Arg Gln Asn Phe Tyr Asn Pro Tyr
        35                  40                  45

Leu Ala Pro Val Gly Thr Gln Gln Lys Pro Thr Gly Pro Thr Gln Arg
    50                  55                  60

His Thr Tyr Tyr Ser Glu Cys Asp Glu Phe Arg Phe Ile Ala Pro Arg
65                  70                  75                  80

Val Leu Asp Glu Asp Ala Pro Pro Glu Lys Arg Ala Gly Val His Asp
                85                  90                  95

Gly His Leu Lys Arg Ala Pro Lys Val Tyr Cys Gly Gly Asp Glu Arg
            100                 105                 110

Asp Val Leu Arg Val Gly Ser Gly Gly Phe Trp Pro Arg Arg Ser Arg
        115                 120                 125

Leu Trp Gly Gly Val Asp His Ala Pro Ala Gly Phe Asn Pro Thr Val
    130                 135                 140

Thr Val Phe His Val Tyr Asp Ile Leu Glu Asn Val Glu His Ala Tyr
145                 150                 155                 160

Gly Met Arg Ala Ala Gln Phe His Ala Arg Phe Met Asp Ala Ile Thr
                165                 170                 175

Pro Thr Gly Thr Val Ile Thr Leu Leu Gly Leu Thr Pro Glu Gly His
            180                 185                 190

Arg Val Ala Val His Val Tyr Gly Thr Arg Gln Tyr Phe Tyr Met Asn
        195                 200                 205

Lys Glu Glu Val Asp Arg His Leu Gln Cys Arg Ala Pro Arg Asp Leu
    210                 215                 220

Cys Glu Arg Met Ala Ala Ala Leu Arg Glu Ser Pro Gly Ala Ser Phe
225                 230                 235                 240

Arg Gly Ile Ser Ala Asp His Phe Glu Ala Glu Val Val Glu Arg Thr
```

-continued

```
                245                 250                 255

Asp Val Tyr Tyr Tyr Glu Thr Arg Pro Ala Leu Phe Tyr Arg Val Tyr
            260                 265                 270

Val Arg Ser Gly Arg Val Leu Ser Tyr Leu Cys Asp Asn Phe Cys Pro
        275                 280                 285

Ala Ile Lys Lys Tyr Glu Gly Gly Val Asp Ala Thr Thr Arg Phe Ile
    290                 295                 300

Leu Asp Asn Pro Gly Phe Val Thr Phe Gly Trp Tyr Arg Leu Lys Pro
305                 310                 315                 320

Gly Arg Asn Asn Thr Leu Ala Gln Pro Arg Ala Pro Met Ala Phe Gly
                325                 330                 335

Thr Ser Ser Asp Val Glu Phe Asn Cys Thr Ala Asp Asn Leu Ala Ile
            340                 345                 350

Glu Gly Gly Met Ser Asp Leu Pro Ala Tyr Lys Leu Met Cys Phe Asp
        355                 360                 365

Ile Glu Cys Lys Ala Gly Gly Glu Asp Glu Leu Ala Phe Pro Val Ala
    370                 375                 380

Gly His Pro Glu Asp Leu Val Ile Gln Ile Ser Cys Leu Leu Tyr Asp
385                 390                 395                 400

Leu Ser Thr Thr Ala Leu Glu His Val Leu Leu Phe Ser Leu Gly Ser
                405                 410                 415

Cys Asp Leu Pro Glu Ser His Leu Asn Glu Leu Ala Ala Arg Gly Leu
            420                 425                 430

Pro Thr Pro Val Val Leu Glu Phe Asp Ser Glu Phe Glu Met Leu Leu
        435                 440                 445

Ala Phe Met Thr Leu Val Lys Gln Tyr Gly Pro Glu Phe Val Thr Gly
    450                 455                 460

Tyr Asn Ile Ile Asn Phe Asp Trp Pro Phe Leu Leu Ala Lys Leu Thr
465                 470                 475                 480

Asp Ile Tyr Lys Val Pro Leu Asp Gly Tyr Gly Arg Met Asn Gly Arg
                485                 490                 495

Gly Val Phe Arg Val Trp Asp Ile Gly Gln Ser His Phe Gln Lys Arg
            500                 505                 510

Ser Lys Ile Lys Val Asn Gly Met Val Asn Ile Asp Met Tyr Gly Ile
        515                 520                 525

Ile Thr Asp Lys Ile Lys Leu Ser Ser Tyr Lys Leu Asn Ala Val Ala
    530                 535                 540

Glu Ala Val Leu Lys Asp Lys Lys Lys Asp Leu Ser Tyr Arg Asp Ile
545                 550                 555                 560

Pro Ala Tyr Tyr Ala Ala Gly Pro Ala Gln Arg Gly Val Ile Gly Glu
                565                 570                 575

Tyr Cys Ile Gln Asp Ser Leu Leu Val Gly Gln Leu Phe Phe Lys Phe
            580                 585                 590

Leu Pro His Leu Glu Leu Ser Ala Val Ala Arg Leu Ala Gly Ile Asn
        595                 600                 605

Ile Thr Arg Thr Ile Tyr Asp Gly Gln Gln Ile Arg Val Phe Thr Cys
    610                 615                 620

Leu Leu Arg Leu Ala Asp Gln Lys Gly Phe Ile Leu Pro Asp Thr Gln
625                 630                 635                 640

Gly Arg Phe Arg Gly Ala Gly Gly Glu Ala Pro Lys Arg Pro Ala Ala
                645                 650                 655

Ala Arg Glu Asp Glu Glu Arg Pro Glu Glu Glu Gly Glu Asp Glu Asp
            660                 665                 670
```

-continued

```
Glu Arg Glu Glu Gly Gly Gly Glu Arg Glu Pro Glu Gly Ala Arg Glu
        675                 680                 685

Thr Ala Gly Arg His Val Gly Tyr Gln Gly Ala Arg Val Leu Asp Pro
    690                 695                 700

Thr Ser Gly Phe His Val Asn Pro Val Val Val Phe Asp Phe Ala Ser
705                 710                 715                 720

Leu Tyr Pro Ser Ile Ile Gln Ala His Asn Leu Cys Phe Ser Thr Leu
                725                 730                 735

Ser Leu Arg Ala Asp Ala Val Ala His Leu Glu Ala Gly Lys Asp Tyr
            740                 745                 750

Leu Glu Ile Glu Val Gly Gly Arg Arg Leu Phe Phe Val Lys Ala His
        755                 760                 765

Val Arg Glu Ser Leu Leu Ser Ile Leu Leu Arg Asp Trp Leu Ala Met
    770                 775                 780

Arg Lys Gln Ile Arg Ser Arg Ile Pro Gln Ser Ser Pro Glu Glu Ala
785                 790                 795                 800

Val Leu Leu Asp Lys Gln Gln Ala Ala Ile Lys Val Val Cys Asn Ser
                805                 810                 815

Val Tyr Gly Phe Thr Gly Val Gln His Gly Leu Leu Pro Cys Leu His
            820                 825                 830

Val Ala Ala Thr Val Thr Thr Ile Gly Arg Glu Met Leu Leu Ala Thr
        835                 840                 845

Arg Glu Tyr Val His Ala Arg Trp Ala Ala Phe Glu Gln Leu Leu Ala
    850                 855                 860

Asp Phe Pro Glu Ala Ala Asp Met Arg Ala Pro Gly Pro Tyr Ser Met
865                 870                 875                 880

Arg Ile Ile Tyr Gly Asp Thr Asp Ser Ile Phe Val Leu Cys Arg Gly
                885                 890                 895

Leu Thr Ala Ala Gly Leu Thr Ala Val Gly Asp Lys Met Ala Ser His
            900                 905                 910

Ile Ser Arg Ala Leu Phe Leu Pro Pro Ile Lys Leu Glu Cys Glu Lys
        915                 920                 925

Thr Phe Thr Lys Leu Leu Leu Ile Ala Lys Lys Lys Tyr Ile Gly Val
    930                 935                 940

Ile Tyr Gly Gly Lys Met Leu Ile Lys Gly Val Asp Leu Val Arg Lys
945                 950                 955                 960

Asn Asn Cys Ala Phe Ile Asn Arg Thr Ser Arg Ala Leu Val Asp Leu
                965                 970                 975

Leu Phe Tyr Asp Asp Thr Val Ser Gly Ala Ala Ala Ala Leu Ala Glu
            980                 985                 990

Arg Pro Ala Glu Glu Trp Leu Ala  Arg Pro Leu Pro Glu  Gly Leu Gln
        995                 1000                1005

Ala Phe  Gly Ala Val Leu Val  Asp Ala His Arg Arg  Ile Thr Asp
    1010                1015                1020

Pro Glu  Arg Asp Ile Gln Asp  Phe Val Leu Thr Ala  Glu Leu Ser
    1025                1030                1035

Arg His  Pro Arg Ala Tyr Thr  Asn Lys Arg Leu Ala  His Leu Thr
    1040                1045                1050

Val Tyr  Tyr Lys Leu Met Ala  Arg Arg Ala Gln Val  Pro Ser Ile
    1055                1060                1065

Lys Asp  Arg Ile Pro Tyr Val  Ile Val Ala Gln Thr  Arg Glu Val
    1070                1075                1080
```

-continued

```
Glu Glu  Thr Val Ala Arg Leu  Ala Ala Leu Arg Glu  Leu Asp Ala
    1085                 1090                 1095

Ala Ala  Pro Gly Asp Glu Pro  Ala Pro Pro Ala Ala  Leu Pro Ser
    1100                 1105                 1110

Pro Ala  Lys Arg Pro Arg Glu  Thr Pro Ser Pro Ala  Asp Pro Pro
    1115                 1120                 1125

Gly Gly  Ala Ser Lys Pro Arg  Lys Leu Leu Val Ser  Glu Leu Ala
    1130                 1135                 1140

Glu Asp  Pro Ala Tyr Ala Ile  Ala His Gly Val Ala  Leu Asn Thr
    1145                 1150                 1155

Asp Tyr  Tyr Phe Ser His Leu  Leu Gly Ala Ala Cys  Val Thr Phe
    1160                 1165                 1170

Lys Ala  Leu Phe Gly Asn Asn  Ala Lys Ile Thr Glu  Ser Leu Leu
    1175                 1180                 1185

Lys Arg  Phe Ile Pro Glu Val  Trp His Pro Pro Asp  Asp Val Ala
    1190                 1195                 1200

Ala Arg  Leu Arg Thr Ala Gly  Phe Gly Ala Val Gly  Ala Gly Ala
    1205                 1210                 1215

Thr Ala  Glu Glu Thr Arg Arg  Met Leu His Arg Ala  Phe Asp Thr
    1220                 1225                 1230

Leu Ala
    1235


<210> SEQ ID NO 5
<211> LENGTH: 1131
<212> TYPE: DNA
<213> ORGANISM: Herpes simplex virus 2

<400> SEQUENCE: 5

atggcttctc acgccggcca acagcacgcg cctgcgttcg gtcaggctgc tcgtgcgagc     60

gggcctaccg acggccgcgc ggcgtcccgt cctagccatc gccagggggc ctccggagcc    120

cgcggggatc cggagctgcc cacgctgctg cgggtttata tagacggacc ccacggggtg    180

gggaagacca ccacctccgc gcagctgatg gaggccctgg ggccgcgcga caatatcgtc    240

tacgtccccg agccgatgac ttactggcag gtgctggggg cctccgagac cctgacgaac    300

atctacaaca cgcagcaccg tctggaccgc ggcgagatat cggccgggga ggcggcggtg    360

gtaatgacca gcgcccagat aacaatgagc acgccttatg cggcgacgga cgccgttttg    420

gctcctcata tcgggggggga ggctgtgggc ccgcaagccc cgcccccggc cctcaccctt    480

gttttcgacc ggcaccctat cgcctccctg ctgtgctacc cggccgcgcg gtacctcatg    540

ggaagcatga ccccccaggc cgtgttggcg ttcgtggccc tcatgccccc gaccgcgccc    600

ggcacgaacc tggtcctggg tgtccttccg gaggccgaac acgccgaccg cctggccaga    660

cgccaacgcc cgggcgagcg gcttgacctg gccatgctgt ccgccattcg ccgtgtctac    720

gatctactcg ccaacacggt gcggtacctg cagcgcggcg ggaggtggcg ggaggactgg    780

ggccggctga cgggggtcgc cgcggcgacc ccgcgccccg accccgagga cggcgcgggg    840

tctctgcccc gcatcgagga cacgctgttt gccctgttcc gcgttcccga gctgctggcc    900

cccaacgggg acttgtacca catttttgcc tgggtcttgg acgtcttggc cgaccgcctc    960

cttccgatgc atctatttgt cctggattac gatcagtcgc ccgtcgggtg tcgagacgcc   1020

ctgttgcgcc tcaccgccgg gatgatccca acccgcgtca caaccgccgg gtccatcgcc   1080

gagatacgcg acctggcgcg cacgtttgcc cgcgaggtgg ggggagttta g            1131
```

<210> SEQ ID NO 6
<211> LENGTH: 376
<212> TYPE: PRT
<213> ORGANISM: Herpes simplex virus 2

<400> SEQUENCE: 6

```
Met Ala Ser His Ala Gly Gln Gln His Ala Pro Ala Phe Gly Gln Ala
1               5                   10                  15

Ala Arg Ala Ser Gly Pro Thr Asp Gly Arg Ala Ala Ser Arg Pro Ser
            20                  25                  30

His Arg Gln Gly Ala Ser Gly Ala Arg Gly Asp Pro Glu Leu Pro Thr
        35                  40                  45

Leu Leu Arg Val Tyr Ile Asp Gly Pro His Gly Val Gly Lys Thr Thr
    50                  55                  60

Thr Ser Ala Gln Leu Met Glu Ala Leu Gly Pro Arg Asp Asn Ile Val
65                  70                  75                  80

Tyr Val Pro Glu Pro Met Thr Tyr Trp Gln Val Leu Gly Ala Ser Glu
                85                  90                  95

Thr Leu Thr Asn Ile Tyr Asn Thr Gln His Arg Leu Asp Arg Gly Glu
            100                 105                 110

Ile Ser Ala Gly Glu Ala Ala Val Val Met Thr Ser Ala Gln Ile Thr
        115                 120                 125

Met Ser Thr Pro Tyr Ala Ala Thr Asp Ala Val Leu Ala Pro His Ile
    130                 135                 140

Gly Gly Glu Ala Val Gly Pro Gln Ala Pro Pro Pro Ala Leu Thr Leu
145                 150                 155                 160

Val Phe Asp Arg His Pro Ile Ala Ser Leu Leu Cys Tyr Pro Ala Ala
                165                 170                 175

Arg Tyr Leu Met Gly Ser Met Thr Pro Gln Ala Val Leu Ala Phe Val
            180                 185                 190

Ala Leu Met Pro Pro Thr Ala Pro Gly Thr Asn Leu Val Leu Gly Val
        195                 200                 205

Leu Pro Glu Ala Glu His Ala Asp Arg Leu Ala Arg Arg Gln Arg Pro
    210                 215                 220

Gly Glu Arg Leu Asp Leu Ala Met Leu Ser Ala Ile Arg Arg Val Tyr
225                 230                 235                 240

Asp Leu Leu Ala Asn Thr Val Arg Tyr Leu Gln Arg Gly Gly Arg Trp
                245                 250                 255

Arg Glu Asp Trp Gly Arg Leu Thr Gly Val Ala Ala Ala Thr Pro Arg
            260                 265                 270

Pro Asp Pro Glu Asp Gly Ala Gly Ser Leu Pro Arg Ile Glu Asp Thr
        275                 280                 285

Leu Phe Ala Leu Phe Arg Val Pro Glu Leu Leu Ala Pro Asn Gly Asp
    290                 295                 300

Leu Tyr His Ile Phe Ala Trp Val Leu Asp Val Leu Ala Asp Arg Leu
305                 310                 315                 320

Leu Pro Met His Leu Phe Val Leu Asp Tyr Asp Gln Ser Pro Val Gly
                325                 330                 335

Cys Arg Asp Ala Leu Leu Arg Leu Thr Ala Gly Met Ile Pro Thr Arg
            340                 345                 350

Val Thr Thr Ala Gly Ser Ile Ala Glu Ile Arg Asp Leu Ala Arg Thr
        355                 360                 365

Phe Ala Arg Glu Val Gly Gly Val
    370                 375
```

-continued

<210> SEQ ID NO 7
<211> LENGTH: 3762
<212> TYPE: DNA
<213> ORGANISM: Herpes simplex virus 2

<400> SEQUENCE: 7

```
atgttttgtg ccgcgggcgg cccggcttcc cccgggggga agccggcggc tcgggcggcg     60
tctgggtttt ttgcccccca caacccccgg ggagccaccc agacggcacc gccgccttgc    120
cgccggcaga acttctacaa cccccacctc gctcagaccg gaacgcagcc aaaggccctc    180
gggccggctc agcgccatac gtactacagc gagtgcgacg aatttcgatt tatcgccccg    240
cgttcgctgg acgaggacgc cccccgcggag cagcgcaccg gggtccacga cggccgcctc    300
cggcgcgccc ctaaggtgta ctgcgggggg gacgagcgcg acgtcctccg cgtgggcccg    360
gagggcttct ggccgcgtcg cttgcgcctg tggggcggtg cggaccatgc ccccgagggg    420
ttcgacccca ccgtcaccgt cttccacgtg tacgacatcc tggagcacgt ggaacacgcg    480
tacagcatgc gcgccgccca gctccacgag cgatttatgg acgccatcac gcccgccggg    540
accgtcatca cgcttctggg tctgaccccc gaaggccatc gcgtcgccgt tcacgtctac    600
ggcacgcggc agtactttta catgaacaag gcggaggtgg atcggcacct gcagtgccgt    660
gccccgcgcg atctctgcga gcgcctggcg gcggccctgc gcgagtcgcc gggggcgtcg    720
ttccgcggca tctccgcgga ccacttcgag gcggaggtgg tggagcgcgc cgacgtgtac    780
tattacgaaa cgcgcccgac cctgtactac cgcgtcttcg tgcgaagcgg gcgcgcgctg    840
gcctacctgt gcgacaactt ttgccccgcg atcaggaagt acgagggggg cgtcgacgcc    900
accacccggt ttatcctgga caacccgggg tttgtcacct tcggctggta ccgcctcaag    960
cccggccgcg ggaacgcgcc ggcccaaccg cgcccccga cggcgttcgg aacctcgagc   1020
gacgtcgagt ttaactgcac ggcggacaac ctggccgtcg aggggggccat gtgtgacctg   1080
ccggcctaca agctcatgtg cttcgatatc gaatgcaagg ccgggggggga ggacgagctg   1140
gcctttccgg tcgcggaacg cccggaagac ctcgtcatcc agatctcctg tctgctctac   1200
gacctgtcca ccaccgccct cgagcacatc ctcctgtttt cgctcggatc ctgcgacctc   1260
cccgagtccc acctcagcga tctcgcctcc aggggcctgc cggcccccgt cgtcctggag   1320
tttgacagcg aattcgagat gctgctggcc ttcatgacct tcgtcaagca gtacggcccc   1380
gagttcgtga ccgggtacaa catcatcaac ttcgactggc ccttcgtcct gaccaagctg   1440
acggagatct acaaggtccc gctcgacggg tacgggcgca tgaacggccg gggtgtgttc   1500
cgcgtgtggg acatcggcca gagccacttt cagaagcgca gcaagatcaa ggtgaacggg   1560
atggtgaaca tcgacatgta cggcatcatc accgacaagg tcaaactctc cagctacaag   1620
ctgaacgccg tcgccgaggc cgtcttgaag gacaagaaga aggatctgag ctaccgcgac   1680
atccccgcct actacgcctc cgggcccgcg cagcgcgggg tgatcggcga gtattgtgtg   1740
caggactcgc tgctggtcgg gcagctgttc ttcaagtttc tgccgcacct ggagctttcc   1800
gccgtcgcgc gcctggcggg catcaacatc acccgcacca tctacgacgg ccagcagatc   1860
cgcgtcttca cgtgcctcct gcgccttgcg ggccagaagg gcttcatcct gccggacacc   1920
caggggcggt ttcggggcct cgacaaggag gcgcccaagc gcccggccgt gcctcggggg   1980
gaaggggagc ggccggggga cgggaacggg gacgaggata aggacgacga cgaggacggg   2040
gacgaggacg ggggacgagcg cgaggaggtc gcgcgcgaga ccgggggccg gcacgttggg   2100
```

-continued

```
taccaggggg cccgggtcct cgaccccacc tccgggtttc acgtcgaccc cgtggtggtg   2160

tttgactttg ccagcctgta ccccagcatc atccaggccc acaacctgtg cttcagtacg   2220

ctctccctgc ggcccgaggc cgtcgcgcac ctggaggcgg accgggacta cctggagatc   2280

gaggtggggg gccgacggct gttcttcgtg aaggcccacg tacgcgagag cctgctgagc   2340

atcctgctgc gcgactggct ggccatgcga aagcagatcc gctcgcggat cccccagagc   2400

acccccgagg aggccgtcct cctcgacaag caacaggccg ccatcaaggt ggtgtgcaac   2460

tcggtgtacg ggttcaccgg ggtgcagcac ggtcttctgc cctgcctgca cgtggccgcc   2520

accgtgacga ccatcggccg cgagatgctc ctcgcgacgc gcgcgtacgt gcacgcgcgc   2580

tgggcggagt tcgatcagct gctggccgac tttccggagg cggccggcat gcgcgccccc   2640

ggtccgtact ccatgcgcat catctacggg gacacggact ccattttcgt tttgtgccgc   2700

ggcctcacgg ccgcgggcct ggtggccatg ggcgacaaga tggcgagcca catctcgcgc   2760

gcgctgttcc tcccccgat caagctcgag tgcgaaaaaa cgttcaccaa gctgctgctc   2820

atcgccaaga aaaagtacat cggcgtcatc tgcgggggca agatgctcat caagggcgtg   2880

gatctggtgc gcaaaaacaa ctgcgcgttt atcaaccgca cctccagggc cctggtcgac   2940

ctgctgtttt acgacgatac cgtatccgga gcggccgccg cgttagccga gcgcccgca   3000

gaggagtggc tggcgcgacc cctgcccgag ggactgcagg cgttcggggc cgtcctcgta   3060

gacgcccatc ggcgcatcac cgacccggag agggacatcc aggactttgt cctcaccgcc   3120

gaactgagca gacacccgcg cgcgtacacc aacaagcgcc tggcccacct gacggtgtat   3180

tacaagctca tggcccgccg cgcgcaggtc ccgtccatca aggaccggat cccgtacgtg   3240

atcgtggccc agacccgcga ggtagaggag acggtcgcgc ggctggccgc cctccgcgag   3300

ctagacgccg ccgccccagg ggacgagccc gcccccccag cggccctgcc ctccccggcc   3360

aagcgccccc gggagacgcc gtcgcatgcc gacccccggg gaggcgcgtc caagccccgc   3420

aagctgctgg tgtccgagct ggcggaggat cccgggtacg ccatcgcccg gggcgttccg   3480

ctcaacacgg actattactt ctcgcacctg ctgggggcgg cctgcgtgac gttcaaggcc   3540

ctgtttggaa ataacgccaa gatcaccgag agtctgttaa agaggtttat tcccgagacg   3600

tggcaccccc cggacgacgt ggccgcgcgg ctcagggccg cggggttcgg gccggcgggg   3660

gccggcgcta cggcggagga aactcgtcga atgttgcata gagcctttga tactctagca   3720

tgagcccccc gtcgaagctg atgtcccgca tcttgcaata aa                      3762
```

<210> SEQ ID NO 8
<211> LENGTH: 1240
<212> TYPE: PRT
<213> ORGANISM: Herpes simplex virus 2

<400> SEQUENCE: 8

```
Met Phe Cys Ala Ala Gly Gly Pro Ala Ser Pro Gly Gly Lys Pro Ala
1               5                   10                  15

Ala Arg Ala Ala Ser Gly Phe Phe Ala Pro His Asn Pro Arg Gly Ala
            20                  25                  30

Thr Gln Thr Ala Pro Pro Pro Cys Arg Arg Gln Asn Phe Tyr Asn Pro
        35                  40                  45

His Leu Ala Gln Thr Gly Thr Gln Pro Lys Ala Leu Gly Pro Ala Gln
    50                  55                  60

Arg His Thr Tyr Tyr Ser Glu Cys Asp Glu Phe Arg Phe Ile Ala Pro
65                  70                  75                  80
```

-continued

```
Arg Ser Leu Asp Glu Asp Ala Pro Ala Glu Gln Arg Thr Gly Val His
                85                  90                  95

Asp Gly Arg Leu Arg Arg Ala Pro Lys Val Tyr Cys Gly Gly Asp Glu
            100                 105                 110

Arg Asp Val Leu Arg Val Gly Pro Glu Gly Phe Trp Pro Arg Arg Leu
        115                 120                 125

Arg Leu Trp Gly Gly Ala Asp His Ala Pro Glu Gly Phe Asp Pro Thr
    130                 135                 140

Val Thr Val Phe His Val Tyr Asp Ile Leu Glu His Val Glu His Ala
145                 150                 155                 160

Tyr Ser Met Arg Ala Ala Gln Leu His Glu Arg Phe Met Asp Ala Ile
                165                 170                 175

Thr Pro Ala Gly Thr Val Ile Thr Leu Leu Gly Leu Thr Pro Glu Gly
            180                 185                 190

His Arg Val Ala Val His Val Tyr Gly Thr Arg Gln Tyr Phe Tyr Met
        195                 200                 205

Asn Lys Ala Glu Val Asp Arg His Leu Gln Cys Arg Ala Pro Arg Asp
    210                 215                 220

Leu Cys Glu Arg Leu Ala Ala Ala Leu Arg Glu Ser Pro Gly Ala Ser
225                 230                 235                 240

Phe Arg Gly Ile Ser Ala Asp His Phe Glu Ala Glu Val Val Glu Arg
                245                 250                 255

Ala Asp Val Tyr Tyr Tyr Glu Thr Arg Pro Thr Leu Tyr Tyr Arg Val
            260                 265                 270

Phe Val Arg Ser Gly Arg Ala Leu Ala Tyr Leu Cys Asp Asn Phe Cys
        275                 280                 285

Pro Ala Ile Arg Lys Tyr Glu Gly Gly Val Asp Ala Thr Thr Arg Phe
    290                 295                 300

Ile Leu Asp Asn Pro Gly Phe Val Thr Phe Gly Trp Tyr Arg Leu Lys
305                 310                 315                 320

Pro Gly Arg Gly Asn Ala Pro Ala Gln Pro Arg Pro Pro Thr Ala Phe
                325                 330                 335

Gly Thr Ser Ser Asp Val Glu Phe Asn Cys Thr Ala Asp Asn Leu Ala
            340                 345                 350

Val Glu Gly Ala Met Cys Asp Leu Pro Ala Tyr Lys Leu Met Cys Phe
        355                 360                 365

Asp Ile Glu Cys Lys Ala Gly Gly Glu Asp Glu Leu Ala Phe Pro Val
    370                 375                 380

Ala Glu Arg Pro Glu Asp Leu Val Ile Gln Ile Ser Cys Leu Leu Tyr
385                 390                 395                 400

Asp Leu Ser Thr Thr Ala Leu Glu His Ile Leu Leu Phe Ser Leu Gly
                405                 410                 415

Ser Cys Asp Leu Pro Glu Ser His Leu Ser Asp Leu Ala Ser Arg Gly
            420                 425                 430

Leu Pro Ala Pro Val Val Leu Glu Phe Asp Ser Glu Phe Glu Met Leu
        435                 440                 445

Leu Ala Phe Met Thr Phe Val Lys Gln Tyr Gly Pro Glu Phe Val Thr
    450                 455                 460

Gly Tyr Asn Ile Ile Asn Phe Asp Trp Pro Phe Val Leu Thr Lys Leu
465                 470                 475                 480

Thr Glu Ile Tyr Lys Val Pro Leu Asp Gly Tyr Gly Arg Met Asn Gly
                485                 490                 495

Arg Gly Val Phe Arg Val Trp Asp Ile Gly Gln Ser His Phe Gln Lys
```

-continued

```
            500                 505                 510

Arg Ser Lys Ile Lys Val Asn Gly Met Val Asn Ile Asp Met Tyr Gly
        515                 520                 525

Ile Ile Thr Asp Lys Val Lys Leu Ser Ser Tyr Lys Leu Asn Ala Val
    530                 535                 540

Ala Glu Ala Val Leu Lys Asp Lys Lys Lys Asp Leu Ser Tyr Arg Asp
545                 550                 555                 560

Ile Pro Ala Tyr Tyr Ala Ser Gly Pro Ala Gln Arg Gly Val Ile Gly
                565                 570                 575

Glu Tyr Cys Val Gln Asp Ser Leu Leu Val Gly Gln Leu Phe Phe Lys
            580                 585                 590

Phe Leu Pro His Leu Glu Leu Ser Ala Val Ala Arg Leu Ala Gly Ile
        595                 600                 605

Asn Ile Thr Arg Thr Ile Tyr Asp Gly Gln Gln Ile Arg Val Phe Thr
    610                 615                 620

Cys Leu Leu Arg Leu Ala Gly Gln Lys Gly Phe Ile Leu Pro Asp Thr
625                 630                 635                 640

Gln Gly Arg Phe Arg Gly Leu Asp Lys Glu Ala Pro Lys Arg Pro Ala
                645                 650                 655

Val Pro Arg Gly Glu Gly Glu Arg Pro Gly Asp Gly Asn Gly Asp Glu
            660                 665                 670

Asp Lys Asp Asp Asp Glu Asp Gly Asp Glu Asp Gly Asp Glu Arg Glu
        675                 680                 685

Glu Val Ala Arg Glu Thr Gly Gly Arg His Val Gly Tyr Gln Gly Ala
    690                 695                 700

Arg Val Leu Asp Pro Thr Ser Gly Phe His Val Asp Pro Val Val Val
705                 710                 715                 720

Phe Asp Phe Ala Ser Leu Tyr Pro Ser Ile Ile Gln Ala His Asn Leu
                725                 730                 735

Cys Phe Ser Thr Leu Ser Leu Arg Pro Glu Ala Val Ala His Leu Glu
            740                 745                 750

Ala Asp Arg Asp Tyr Leu Glu Ile Glu Val Gly Gly Arg Arg Leu Phe
        755                 760                 765

Phe Val Lys Ala His Val Arg Glu Ser Leu Leu Ser Ile Leu Leu Arg
    770                 775                 780

Asp Trp Leu Ala Met Arg Lys Gln Ile Arg Ser Arg Ile Pro Gln Ser
785                 790                 795                 800

Thr Pro Glu Glu Ala Val Leu Leu Asp Lys Gln Gln Ala Ala Ile Lys
                805                 810                 815

Val Val Cys Asn Ser Val Tyr Gly Phe Thr Gly Val Gln His Gly Leu
            820                 825                 830

Leu Pro Cys Leu His Val Ala Ala Thr Val Thr Thr Ile Gly Arg Glu
        835                 840                 845

Met Leu Leu Ala Thr Arg Ala Tyr Val His Ala Arg Trp Ala Glu Phe
    850                 855                 860

Asp Gln Leu Leu Ala Asp Phe Pro Glu Ala Ala Gly Met Arg Ala Pro
865                 870                 875                 880

Gly Pro Tyr Ser Met Arg Ile Ile Tyr Gly Asp Thr Asp Ser Ile Phe
                885                 890                 895

Val Leu Cys Arg Gly Leu Thr Ala Ala Gly Leu Val Ala Met Gly Asp
            900                 905                 910

Lys Met Ala Ser His Ile Ser Arg Ala Leu Phe Leu Pro Pro Ile Lys
        915                 920                 925
```

-continued

```
Leu Glu Cys Glu Lys Thr Phe Thr Lys Leu Leu Leu Ile Ala Lys Lys
    930                 935                 940

Lys Tyr Ile Gly Val Ile Cys Gly Gly Lys Met Leu Ile Lys Gly Val
945                 950                 955                 960

Asp Leu Val Arg Lys Asn Asn Cys Ala Phe Ile Asn Arg Thr Ser Arg
                965                 970                 975

Ala Leu Val Asp Leu Leu Phe Tyr Asp Asp Thr Val Ser Gly Ala Ala
            980                 985                 990

Ala Ala Leu Ala Glu Arg Pro Ala  Glu Glu Trp Leu Ala  Arg Pro Leu
        995                 1000                1005

Pro Glu  Gly Leu Gln Ala Phe  Gly Ala Val Leu Val  Asp Ala His
    1010                 1015                 1020

Arg Arg  Ile Thr Asp Pro Glu  Arg Asp Ile Gln Asp  Phe Val Leu
    1025                 1030                 1035

Thr Ala  Glu Leu Ser Arg His  Pro Arg Ala Tyr Thr  Asn Lys Arg
    1040                 1045                 1050

Leu Ala  His Leu Thr Val Tyr  Tyr Lys Leu Met Ala  Arg Arg Ala
    1055                 1060                 1065

Gln Val  Pro Ser Ile Lys Asp  Arg Ile Pro Tyr Val  Ile Val Ala
    1070                 1075                 1080

Gln Thr  Arg Glu Val Glu Glu  Thr Val Ala Arg Leu  Ala Ala Leu
    1085                 1090                 1095

Arg Glu  Leu Asp Ala Ala Ala  Pro Gly Asp Glu Pro  Ala Pro Pro
    1100                 1105                 1110

Ala Ala  Leu Pro Ser Pro Ala  Lys Arg Pro Arg Glu  Thr Pro Ser
    1115                 1120                 1125

His Ala  Asp Pro Pro Gly Gly  Ala Ser Lys Pro Arg  Lys Leu Leu
    1130                 1135                 1140

Val Ser  Glu Leu Ala Glu Asp  Pro Gly Tyr Ala Ile  Ala Arg Gly
    1145                 1150                 1155

Val Pro  Leu Asn Thr Asp Tyr  Tyr Phe Ser His Leu  Leu Gly Ala
    1160                 1165                 1170

Ala Cys  Val Thr Phe Lys Ala  Leu Phe Gly Asn Asn  Ala Lys Ile
    1175                 1180                 1185

Thr Glu  Ser Leu Leu Lys Arg  Phe Ile Pro Glu Thr  Trp His Pro
    1190                 1195                 1200

Pro Asp  Asp Val Ala Ala Arg  Leu Arg Ala Ala Gly  Phe Gly Pro
    1205                 1210                 1215

Ala Gly  Ala Gly Ala Thr Ala  Glu Glu Thr Arg Arg  Met Leu His
    1220                 1225                 1230

Arg Ala  Phe Asp Thr Leu Ala
    1235                 1240
```

METHODS FOR DETECTING ANTIVIRAL-DRUG RESISTANT VIRUS

The present invention relates to methods for detecting an antiviral drug resistant Herpes Simplex Virus (HSV), and for diagnosing an infection with an antiviral drug-resistant HSV comprising the use of an HSV mutation/polymorphism.

Herpes simplex is a viral disease caused by the herpes simplex virus and is categorised based on the part of the body infected. Oral herpes involves the face or mouth. It may result in small blisters in groups often called cold sores or fever blisters or may just cause a sore throat. Genital herpes may form blisters that break open and result in small ulcers. Infection with HSV results in significant discomfort and may result in fever, muscle pains, swollen lymph nodes and headaches.

HSV comprises type 1 (HSV-1) and type 2 (HSV-2). HSV-1 more commonly causes infections around the mouth while HSV-2 more commonly causes genital infections. They can be transmitted by direct contact with body fluids or lesions of an infected individual and transmission may still occur when symptoms are not present. Genital herpes is classified as a sexually transmitted infection. It may be spread to an infant during childbirth. After infection, the viruses are transported along sensory nerves to the nerve cell bodies, where they reside lifelong. Recurrence of the viral infection can occur during immune suppression; for example, in patients undergoing bone marrow or solid organ transplantation, anticancer therapy or individuals in high-risk groups, for example, pregnant women, newborns and the elderly.

Over 70% of the adult population in the UK is infected with HSV. The infection is of clinical significance in immunocompromised individuals especially those undergoing bone marrow transplantation (BMT) and is treated with antivirals such as acyclovir (ACV) and penciclovir (PCV) (first line drugs), as well as foscarnet and cidofovir (second-line drugs). However, HSV (e.g. HSV-1 and HSV-2) can develop resistance to one of more of these drugs, and there is evidence that resistance to these treatments is increasing.

ACV and PCV are guanine analogues that act as chain terminators and block viral replication by inhibiting the viral DNA polymerase. Both drugs need to be triphosphorylated to become active and the first phosphorylation step is carried out by the HSV thymidine kinase (TK). Resistance to the drugs develops usually via the development of mutations (e.g. non-synonymous mutations) in the TK genes (UL23) and occasionally in the viral DNA polymerase genes (UL30). The resistance mutations are variable and consist of substitutions, deletions and insertions. The latter two types of mutations often occur in homopolymeric regions (usually a run of Cs or Gs) and often result in premature stop codons. Substitutions often result in corresponding amino acid sequence substitution polymorphisms. The antivirals foscarnet (FOS) and cidofovir (CDV) are viral DNA polymerase inhibitors (that are often used as second-line therapy) do not require activation by viral TK. Therefore, resistance to these two drugs usually develops via emergence of mutations in viral DNA polymerase and can result in cross-resistance to ACV and PCV.

Currently, there is no reliable test for drug-resistant HSV based on sequence analysis (e.g. detecting mutations/polymorphisms). Diagnosis of an antiviral drug-resistant HSV infection relies on assays based on assessing the phenotype of a virus. The gold standard assay involves phenotypic drug susceptibility testing using a plaque reduction assay. This requires isolation of virus (e.g. whole intact virus) which is difficult and time consuming. Therefore, the assay has long turnaround times of weeks; however, it is well standardised. Nonetheless, due to the cost and expertise required it is usually only performed by reference laboratories.

The interpretation of the potential resistance-causing effect of any mutation/polymorphism by genotypic methods is complex. Substitution mutations/polymorphisms are particularly difficult to interpret as the number of 'natural' mutations/polymorphisms in HSV, which do not result in drug resistance, vastly outnumbers the number of resistance-causing mutations/polymorphisms (e.g. substitutions), such that it is very difficult to determine resistance based on the sequence of TK or DNA pol alone. Therefore, it is highly unexpected that any one mutation (e.g. substitution) will cause resistance. This problem is exacerbated due to the fact that a public database of known and phenotypically characterised drug resistance-associated mutations/polymorphisms does not exist. While a number of resistance-associated mutations have previously been reported, these mutations were not interpreted/verified via a standardised assay and thus the resistance associated with these mutations is not directly comparable.

The present invention solves at least one of the above-mentioned problems.

In one aspect there is provided a method for detecting an antiviral drug-resistant HSV (e.g. in a subject), comprising:

a. identifying one or more HSV mutation selected from:
   i. a thymidine kinase (TK) mutation selected from 100C>T (HSV-1), 268C>T (HSV-2), 373C>T (HSV-1), 376C>T (HSV-2), 146T>G (HSV-1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>C (HSV-1), 938T>C (HSV-2), 437_438insA (HSV-1), 169delC (HSV-1), 170delC (HSV-1), 171delC (HSV-1), 172delC (HSV-1), 276delG (HSV-2), 278delG (HSV-2), 279delG (HSV-2), 280delG (HSV-2), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1); and
   ii. a DNA polymerase (DNA pol) mutation selected from 18790>G (HSV-1), 18820>G (HSV-2), 2405T>G (HSV-1), 2420T>G (HSV-2), 2500G>T (HSV-1), 2515G>T (HSV-2), 2515A>G (HSV-1), 2530A>G (HSV-2), 2892_2893 insT (HSV-1), 2893_2894 insT (HSV-1), 2894_2895 insT (HSV-1), 2895_2896 insT (HSV-1), 2907_2908 insT (HSV-2), 2908_2909 T (HSV-2), 2909_2910 T (HSV-2), and 2910_2911 T (HSV-2);

wherein the presence of said one or more HSV mutation confirms the presence of an antiviral drug-resistant HSV, and the absence of said one or more HSV mutation is indicative of the absence of an antiviral drug-resistant HSV.

The term "indicative" as used in the context of "the absence of said one or more HSV mutation is indicative of the absence of an antiviral drug-resistant HSV" means that the HSV may be less likely to be an antiviral drug-resistant HSV when compared with an HSV comprising said mutation. The skilled person will understand that antiviral drug-resistance may (regardless) be conferred by an alternative mutation.

Mutations followed by "HSV-1" in parentheses may be identified in a HSV-1 virus. Mutations followed by "HSV-2" in parentheses may be identified in a HSV-2 virus.

Surprisingly, these mutations find utility as robust markers for detecting antiviral drug-resistant HSV. Furthermore, a comprehensive database of such mutations (including associated HSV phenotypes) is provided together with algorithms for interpreting the phenotype resulting from a given mutation or mutation profile.

For the first time, the present inventors have genotyped numerous clinical isolates comprising antiviral drug-resistant HSV with a standardised assay, and have generated an extensive list of mutations which are particularly suitable for use in detecting an antiviral drug-resistant HSV and for diagnosis with an infection of the same. Advantageously, each of these mutations (as well as previously identified mutations) have been verified by the gold standard plaque reduction assay, such that the resulting phenotypes are directly comparable.

The same assay was also used to validate the phenotype of a large number of mutations not associated with antiviral drug-resistance (e.g. natural) mutations/polymorphisms.

In a preferable embodiment, said thymidine kinase (TK) mutation is selected from 250G>A (HSV-2), 100C>T (HSV-1), 268C>T (HSV-2), 373C>T (HSV-1), 146T>G (HSV-1), 363G>A (HSV-1), 497T>A (HSV-1), 558G>T (HSV-2), 641A>G (HSV-2), 715T>C (HSV-1), 938T>C (HSV-2), 437_438 insA (HSV-1), 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1). In a preferable embodiment, said DNA polymerase (DNA pol) mutation is selected from 1882C>G (HSV-2), 2405T>G (HSV-1), 2500G>T (HSV-1), 2515A>G (HSV-1), 2892_2893 insT (HSV-1), 2893_2894 insT (HSV-1), 2894_2895 insT (HSV-1), and 2895_2896insT (HSV-1).

In a preferable embodiment, said TK polymorphism selected from E84K (HSV-2), Q34* (HSV-1), Q90* (HSV-2), Q125* (HSV-1), L49R (HSV-1), M1211 (HSV-1), 1166N (HSV-1), Q186H (HSV-2), H214R (HSV-2), E146fs (HSV-1), D228* (HSV-1), Y239H (HSV-1), L313S (HSV-2), T183* (HSV-1), H58fs (HSV-1), M85* (HSV-1), P154fs (HSV-2), M183* (HSV-2), A294fs (HSV-1), P295fs (HSV-1), and E296fs (HSV-1). In a preferable embodiment, R628G (HSV-2), L802R (HSV-1), A834S (HSV-1), T839A (HSV-1), F965_I966insF (HSV-1), and 1966* (HSV-1).

In one embodiment, the mutation is a pyridine to pyridine substitution. In one embodiment, the mutation is a pyrimidine to pyrimidine substitution.

The mutation/polymorphism nomenclature used herein is described for example in J. T. den Dunnen, S. E. Antonarakis: Hum Genet 109(1): 121-124 (2001), which is incorporated herein by reference. Mutations may be detected in genomic DNA, cDNA or RNA. Optionally, a description of a mutation may be preceded by a sign selected from g., c., and r to denote identification of a mutation in DNA, cDNA or RNA, respectively. For example, a mutation 748G>C in genomic DNA may be referred to as g.748G>C.

This method may be performed on a sequence (e.g. nucleic acid sequence) comprised within a HSV sequence (e.g. comprised within a TK and/or DNA pol sequence). Said sequence may be determined (e.g. obtained) either prior to carrying out the present method or at the same time as carrying out the present method. In one embodiment, the method comprises identifying the presence or absence of said one or more HSV mutation in a sequence, preferably a TK and/or DNA pol sequence. In one embodiment the presence or absence of said one or more HSV mutation is detected in a database of HSV mutations, wherein said database comprises said one or more HSV mutation.

The methods of the present invention may be performed in silico e.g. by aligning a HSV sequence with the sequence of a reference HSV (e.g. wild-type HSV). Alternatively, the sequence may be investigated (e.g. parsed) for the presence of one or more of said HSV mutations.

In a further aspect, the invention provides a method for treating an infection of an antiviral drug-resistant HSV in a subject, comprising:

a. confirming an antiviral drug-resistant HSV comprises a TK mutation selected from 100C>T (HSV-1), 268C>T (HSV-2), 373C>T (HSV-1), 376C>T (HSV-2), 146T>G (HSV-1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>C (HSV-1), 938T>C (HSV-2), 437_438 insA (HSV-1), 169delC (HSV-1), 170delC (HSV-1), 171delC (HSV-1), 172delC (HSV-1), 276delG (HSV-2), 278delG (HSV-2), 279delG (HSV-2), 280delG (HSV-2), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1); and b. administering to said subject a drug selected from foscarnet, cidofovir drug and docosanol.

In a preferable embodiment, said thymidine kinase (TK) mutation is selected from 250G>A (HSV-2), 100C>T (HSV-1), 268C>T (HSV-2), 373C>T (HSV-1), 146T>G (HSV-1), 363G>A (HSV-1), 497T>A (HSV-1), 558G>T (HSV-2), 641A>G (HSV-2), 715T>C (HSV-1), 938T>C (HSV-2), 437_438 insA (HSV-1), 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1).

Suitably, step a. may further comprise confirming said antiviral drug-resistant HSV does not comprise a DNA Pol mutation associated with resistance to an antiviral drug. In one embodiment, step a. further comprises confirming said antiviral drug-resistant HSV does not comprise a DNA Pol mutation is selected from 1879C>G (HSV-1), 1882C>G (HSV-2), 2405T>G (HSV-1), 2420T>G (HSV-2), 2500G>T (HSV-1), 2515G>T (HSV-2), 2515A>G (HSV-1), 2530A>G (HSV-2), 2892_2893 insT (HSV-1), 2893_2894 insT (HSV-1), 2894_2895 insT (HSV-1), 2895_2896 insT (HSV-1), 2907_2908 insT (HSV-2), 2908_2909 insT (HSV-2), 2909_2910 insT (HSV-2), and 2910_2911 insT (HSV-2) (preferably 18820>G (HSV-2), 2405T>G (HSV-1), 2500G>T (HSV-1), 2515A>G (HSV-1), 2892_2893 insT (HSV-1), 2893_2894 insT (HSV-1), 2894_2895 insT (HSV-1), and/or 2895_2896 insT (HSV-1)).

In one embodiment, step b. comprises administering to the subject a non-acyclovir and/or non-penciclovir drug. In one embodiment, step b. comprises administering to said subject a drug selected from a foscarnet, a cidofovir drug, a docosanol drug, BAY 54-6322, ASP2151 and BAY 57-1293.

In another aspect, there is provided a method for treating an infection of an antiviral drug-resistant HSV in a subject, comprising:

a. confirming an antiviral drug-resistant HSV comprises a DNA Pol mutation selected from 18790>G (HSV-1), 18820>G (HSV-2), 2405T>G (HSV-1), 2420T>G (HSV-2), 2500G>T (HSV-1), 2515G>T (HSV-2), 2515A>G (HSV-1), 2530A>G (HSV-2), 2892_2893 insT (HSV-1), 2893_2894 insT (HSV-1), 2894_2895 insT (HSV-1), 2895_2896 insT (HSV-1), 2907_2908 insT (HSV-2), 2908_2909 insT (HSV-2), 2909_2910 insT (HSV-2), and 2910_2911 insT (HSV-2); and b. administering to said subject a drug selected from a docosanol drug, BAY 54-6322, ASP2151 and BAY 57-1293.

In a preferable embodiment, said DNA polymerase (DNA pol) mutation is selected from 18820>G (HSV-2), 2405T>G (HSV-1), 2500G>T (HSV-1), 2515A>G (HSV-1), 2892_2893 insT (HSV-1), 2893_2894 insT (HSV-1), 2894_2895 insT (HSV-1), and 2895_2896 insT (HSV-1).

Suitably, step a. may further comprise confirming said antiviral drug-resistant HSV does not comprise a TK mutation associated with resistance to an antiviral drug. In one embodiment, step a. further comprises confirming said antiviral drug-resistant HSV does not comprise a TK mutation selected from 100C>T (HSV-1), 268C>T (HSV-2), 373C>T (HSV-1), 3760>T (HSV-2), 146T>G (HSV-1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>C (HSV-1), 938T>C (HSV-2), 437_438 insA (HSV-1), 169delC (HSV-1), 170delC (HSV-1), 171delC (HSV-1), 172delC (HSV-1), 276delG (HSV-2), 278delG (HSV-2), 279delG (HSV-2), 280delG (HSV-2), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1) (preferably 250G>A (HSV-2), 100C>T (HSV-1), 268C>T (HSV-2), 373C>T (HSV-1), 146T>G (HSV-1), 363G>A (HSV-1), 497T>A (HSV-1), 558G>T (HSV-2), 641A>G (HSV-2), 715T>C (HSV-1), 938T>C (HSV-2), 437_438 insA (HSV-1), 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and/or 885delC (HSV-1)).

In one embodiment, step b. above comprises administering to the subject a non-acyclovir drug, a non-penciclovir drug, a non-foscarnet drug and/or a non-cidofovir drug.

The methods of the invention are intended to encompass all known treatments for an HSV infection.

In one embodiment, the method comprises confirming that an antiviral drug-resistant HSV comprises a DNA Pol mutation selected from 2405T>G (HSV-1), 2420T>G (HSV-2), 2500G>T (HSV-1), and 2515G>T (HSV-2) (preferably 2405T>G (HSV-1), and/or 2500G>T (HSV-1); and administering to said subject a cidofovir drug.

In one embodiment, the method comprises confirming that an antiviral drug-resistant HSV comprises a DNA Pol mutation selected from 2515A>G (HSV-1), and 2530A>G (HSV-2) (preferably 2515A>G (HSV-1)); and administering to said subject a foscarnet and/or cidofovir drug.

In one embodiment, the method comprises confirming that an antiviral drug-resistant HSV comprises a DNA Pol mutation selected from 2892_2893 insT (HSV-1), 2893_2894 insT (HSV-1), 2894_2895 insT (HSV-1), 2895_2896 insT (HSV-1), 2907_2908 insT (HSV-2), 2908_2909 insT (HSV-2), 2909_2910 insT (HSV-2), and 2910_2911 insT (HSV-2) (preferably from 2892_2893 insT (HSV-1), 2893_2894 insT (HSV-1), 2894_2895 insT (HSV-1), 2895_2896 insT (HSV-1)); and administering to said subject an acyclovir drug, a penciclovir drug, and/or a foscarnet drug.

In one embodiment, the method comprises confirming that an antiviral drug-resistant HSV comprises a DNA Pol mutation selected from 18790>G (HSV-1), and 18820>G (HSV-2) (preferably 18820>G (HSV-2)); and administering to said subject a cidofovir drug.

In one embodiment, the method comprises confirming that an antiviral drug-resistant HSV comprises a TK and/or DNA pol mutation as described herein (e.g. a TK and/or DNA pol mutation associated with resistance to an antiviral drug) and administering to a subject a drug selected from a docosanol drug, BAY 54-6322, ASP2151 and BAY 57-1293.

The absence of one or more HSV mutation as described herein is indicative of the absence of an antiviral drug-resistant HSV. Various further resistance-associated mutations exist, such that there may be presence of an antiviral drug-resistant HSV when the absence of one or more HSV mutation described herein is identified. As such, the absence of one or more of said HSV mutation is an indicator of the absence of an antiviral drug-resistant HSV.

In one embodiment, a method of the invention comprises identifying (or confirming the presence of) one or more further HSV TK and/or HSV mutation.

In one embodiment, a method of the invention comprises identifying one or more further HSV-1 TK mutation selected from 11_12 insC, 12_13 insC, 13_14 insC, 14_15 insC, 15_16 insC, 122G>A, 1510>T, 158A>G, 157T>G, 157T>C, 159T>A, 163G>A, 166G>T, 177G>C, 170C>A, 172C>A, 173A>G, 175G>C, 175G>T, 186A>C, 187A>G, 1880>T, 194C>A, 1990>T, 2210>G, 222C>A, 238T>A, 247G>T, 2520>T, 2500>T, 184delA, 185delA, 186delA, 187delA, 180delG, 181delG, 182delG, 183delG, 259T>C, 262T>C, 2650>T, 283G>A, 307A>C, 3100>T, 312A>T, 3100>T, 314A>C, 181_182 insG, 182_183insG, 183_184insG, 184_185insG, 185_186insG, 186_187insG, 272_273insG, 273_274insG, 274_275insG, 275_276insG, 276_277insG, 277_278insG, 278_279insG, 346G>A, 277delG, 362T>G, 369C>A, 3690>G, 375G>C, 382A>C, 386G>A, 3910>T, 427A>G, 485A>C, 484G>C, 484G>A, 488G>A, 500G>T, 502G>A, 509T>C, 515A>G, 5180>T, 5180>G, 520G>C, 5240>T, 527G>A, 5260>T, 5260>T, 528A>G, 533T>G, 542G>A, 455delC, 456delC, 457delC, 458delC, 460delC, 461delC, 462delC, 463delC, 464delC, 430delG, 431delG, 432delG, 433delG, 434delG, 435delG, 436delG, 429_430insGG, 430_431insGG, 431_432insGG, 432_433insGG, 433_434insGG, 434_435insGG, 435_436insGG, 436_437insGG, 437_438insGG, 438_439insGG, 553C>A, 554A>G, 559G>A, 5660>T, 582_584 del, 598G>T, 599G>A, 598G>T, 599G>C, 601A>C, 611T>G, 616G>A, 619G>C, 6220>T, 623T>A, 6460>T, 647G>A, 6460>T, 647G>C, 6580>T, 659G>A, 6640>T, 665G>A, 666delC, 667delC, 668delC, 669delC, 6790>T, 363_364insT, 429_430insG, 430_431insG, 431_432insG, 432_433insG, 433_434insG, 434_435insG, 435_436 insG, 436_437 insG, 437_438 insG, 459_460 insC, 460_461 insC, 461_462insC, 462_463 insC, 463_464 insC, 464_465 insC, 465_466 insC, 547_548 insC, 548_549insC, 549_550 insC, 551_552 insC, 552_553 insC, 553_554 insC, 650_651 insT, 716A>C, 2450>T, 733A>C, 746T>C, 7480>T, 7660>T, 769G>A, 782A>G, 782A>T, 781_793del, 548delC, 549delC, 550delC, 551delC, 552delC, 553delC, 8410>T, 853delG, 854delC, 855delC, 856delC, 8600>T, 862T>A, 872T>G, 878delG, 879delG, 880delG, 890T>C, 896del, 897delG, 898delC, 899delG, 900delG, 895_896 insGCC, 896_897 insGCC, 697_698insC, 698_699 insC, 699_700 insC, 700_701 insC, 832_833 insC, 833_834 insC, 834_835insC, 835_836 insC, 836_837 insC, 837_838 insC, 838_839 insC, 900_901 insA, 901_902insA, 902_903 insA, 903_904 insA, 903_904 insA, 904_905 insA, 905_906 insA, 906_907insA, 919delG, 944T>C, 965T>A, 996delG, 1007G>A, 10240>T, 1025A>G, 1060A>C, 1061delC, 1062delC, 1063delC, 1064delC, 1065delC, 1065delA, 1039G>A, 1117delG, 1118delG, 1119delG, 1120delG, 1121delG, 363_1128+201 del, 665insC, 666insC, 667insC, 668insC, 669insC, 918_919 insG, 928_929 insT, 1060_1061 insC, 1061_1062 insC, 1062_1063insC, 1063_1064 insC, 1064_1065 insC, and 1065_1066insC.

In one embodiment, a method of the invention comprises identifying one or more further HSV-2 TK mutation selected from 1_742 del, 8_9 insT, 1000>T, 153T>C, 157T>A, 25delC, 43delC, 175G>C, 176G>C, 181G>T, 186A>C, 196T>C, 180delG, 181delG, 182delG, 183delG, 214G>A, 2150>G, 219delG, 220delG, 221delG, 222delG, 2810>T, 280delG, 302T>G, 314A>C, 363_1128+204 del, 391A>C, 398A>T, 409G>T, 411C>A, 4110>G, 472T>C, 5290>T, 544A>G, 545G>A, 545G>C, 549G>A, 549G>C, 549G>U, 450delC, 451delC, 452delC, 463delC, 464delC, 465delC, 466delC, 467delC, 470delC, 471delC, 472delC, 519delC, 520delC, 521delC, 433delG, 434delG, 435delG, 436delG, 437delG, 438delG, 439delG, 416delT, 417delT, 418delT, 419delT, 482delT, 483delT, 484delT, 485delT, 432_433 insGG, 433_434 insGG, 434_435 insGG, 435_436 insGG, 436_437 insGG, 437_438insGG, 438_439 insGG, 439_440 insGG, 602G>A, 649G>A, 658A>T, 658A>C, 6640>T, 669G>A, 111_127 del, 365_366 insT, 551delC, 552delC, 553delC, 554delC, 555delC, 556delC, 550_551 insC, 551_552 insC, 552_553 insC, 553_554 insC, 554_555 insC, 555_556insC, 556_557insC, 585_586insC, 586_587 insC, 587_588 insC, 588_589 insC, 586_587 insC, 587_588 insC, 588_589 insC, 589_590insC, 590_591insC, 433delG, 434delG, 435delG, 436delG, 437delG, 438delG, 439delG432_433 insG, 433_434 insG, 434_435 insG, 435_436insG, 436_437insG, 437_438insG, 438_439insG, 439_440 insG, 439_440 insG, 440_441insG, 441_442 insG, 442_443 insG, 625_626 insT, 626_627 insT, 627_628 insT, 720T>G, 720T>A, 773_774 insG, 773_774 insG, 774_775 insG, 775_776 insG, 551_556 del, 551delC, 552delC, 553delC, 554delC, 555delC, 586delC, 587delC, 588delC, 589delC, 590delC, 651_654 del, 779delG, 780delG, 781delG, 782delG, 8140>G, 815G>T, 8140>T, 820G>A, 820G>C, 8210>G, 8630>T, 862_863 del, 921_922 insA, 999_1000 insC, 1000_1001insC, 1001_1002insC, 1002_1003insC, 1007G>A, 821_833del, 809delC, 810delC, 811delC, 812delC, 816delC, 817delC, 818delC, 819delC, 814_826 del, 856delG, 923delT, 924delT, 925delT, 926delT, and 927delT.

In one embodiment, a method of the invention comprises identifying one or more further HSV-1 DNA pol mutation selected from 1_742 del, 8_9 insT, 100C>T, 153T>C, 157T>A, 25delC, 43delC, 175G>C, 176G>C, 181G>T, 186A>C, 196T>C, 180delG, 181delG, 182delG, 183delG, 214G>A, 215C>G, 219delG, 220delG, 221delG, 222delG, 281C>T, 280delG, 302T>G, 314A>C, 363_1128+204 del, 391A>C, 398A>T, 409G>T, 411C>A, 411C>G, 472T>C, 529C>T, 544A>G, 545G>A, 545G>C, 549G>A, 549G>C, 549G>U, 450delC, 451delC, 452delC, 463delC, 464delC, 465delC, 466delC, 467delC, 470delC, 471delC, 472delC, 519delC, 520delC, 521delC, 433delG, 434delG, 435delG, 436delG, 437delG, 438delG, 439delG, 416delT, 417delT, 418delT, 419delT, 482delT, 483delT, 484delT, 485delT, 432_433 insGG, 433_434 insGG, 434_435 insGG, 435_436 insGG, 436_437insGG, 437_438insGG, 438_439insGG, 439_440insGG, 602G>A, 649G>A, 658A>T, 658A>C, 664C>T, 669G>A, 111_127 del, 365_366 insT, 551delC, 552delC, 553delC, 554delC, 555delC, 556delC, 550_551 insC, 551_552 insC, 552_553 insC, 553_554insC, 554_555insC, 555_556insC, 556_557insC, 585_586insC, 586_587 insC, 587_588 insC, 588_589 insC, 586_587 insC, 587_588 insC, 588_589 insC, 589_590insC, 590_591insC, 433delG, 434delG, 435delG, 436delG, 437delG, 438delG, 439delG432_433 insG, 433_434 insG, 434_435 insG, 435_436 insG, 436_437 insG, 437_438insG, 438_439insG, 439_440 insG, 439_440 insG, 440_441insG, 441_442insG, 442_443insG, 625_626insT, 626_627insT, 627_628insT, 720T>G, 720T>A, 773_774 insG, 773_774 insG, 774_775insG, 775_776insG, 551_556del, 551delC, 552delC, 553delC, 554delC, 555delC, 586delC, 587delC, 588delC, 589delC, 590delC, 651_654 del, 779delG, 780delG, 781delG, 782delG, 814C>G, 815G>T, 814C>T, 820G>A, 820G>C, 821C>G, 8630>T, 862_863 del, 921_922 insA, 999_1000 insC, 1000_1001 insC, 1001_1002 insC, 1002_1003insC, 1007G>A, 821_833 del, 809delC, 810delC, 811delC, 812delC, 816delC, 817delC, 818delC, 819delC, 814_826 del, 856delG, 923delT, 924delT, 925delT, 926delT, and 927delT.

In one embodiment, a method of the invention comprises identifying one or more further HSV-2 DNA pol mutation selected from 748G>C, 919G>A, 1882C>T, 2033A>G, 2049_2056insGAAGAC, 2170G>A, 2171C>T, 2173A>G, 2186G>A, 2194C>A, 2347C>A, 2353G>A, 2485C>A, 2548C>A, 2729T>C, 2734G>A, 2735A>T, and 2744C>T.

In a preferable embodiment, the presence of said one or more further HSV mutation (e.g. further HSV-1 TK mutation, further HSV-2 TK mutation, further HSV-1 DNA pol mutation and/or further HSV-2 DNA pol mutation) is indicative of the presence of an antiviral drug-resistant HSV. In one embodiment, the presence of said one or more HSV mutation confirms the presence of an antiviral drug-resistant HSV.

In a preferable embodiment, the absence of said one or more further HSV mutation (e.g. further HSV-1 TK mutation, further HSV-2 TK mutation, further HSV-1 DNA pol mutation and/or further HSV-2 DNA pol mutation) is indicative of the absence of an antiviral drug-resistant HSV. In one embodiment, the absence of said one or more HSV mutation confirms the absence of an antiviral drug-resistant HSV.

The presence or absence of said one or more further HSV mutation may be identified either within (i.e. constituting a step of) or externally to methods of the invention. In one embodiment, the methods of the invention comprise a step of identifying the presence or absence of said one or more further HSV mutation. The presence or absence of said one or more further HSV mutation may have been previously identified. In one embodiment, the presence or absence of said one or more further HSV mutation is identified externally to methods of the invention.

The person skilled in the art understands the nomenclature used to describe the mutations (e.g. nucleotide mutations) and polymorphisms (e.g. polypeptide polymorphisms) which are described herein. Nucleotide positions of TK and DNA pol genes are numbered relative to the first nucleotide of the coding sequence of the respective genes, wherein the first nucleotide of the coding sequence (e.g. the 'adenine', A, of the ATG start codon) corresponds to position 1. Preferably, the nucleotide positions of HSV-1 TK are numbered relative to the first nucleotide of SEQ ID NO: 1 (e.g. a reference sequence); the nucleotide positions of HSV-1 DNA pol are numbered relative to the first nucleotide of SEQ ID NO: 3 (e.g. a reference sequence); the nucleotide positions of HSV-2 TK are numbered relative to the first nucleotide of SEQ ID NO: 5 (e.g. a reference sequence); and/or the nucleotide positions of HSV-2 DNA pol are numbered relative to the first nucleotide of SEQ ID NO: 7 (e.g. a reference sequence).

Advantageously, diagnosis of infection and the severity of drug resistance can be made by the identification of a mutation in a TK or DNA pol sequence (e.g. via DNA sequencing or sequencing of the polypeptide sequence). The present method of diagnosis is objective and is highly accurate. It may be performed by non-experts with routine training in molecular techniques in a short period of time. The method of the invention may be used for diagnosing infection of a subject with an antiviral drug-resistant HSV. In a preferable embodiment, the presence or absence of one or more of said HSV mutations is identified in an isolated sample obtained from a subject.

Thus, in one aspect there is provided a method for diagnosing an infection with an antiviral drug-resistant herpes simplex virus (e.g. HSV-1 and/or HSV-2) in a subject, comprising:

a. obtaining an isolated sample from said subject; and
b. detecting the presence or absence of one or more HSV in said sample, wherein said one or more HSV mutation is selected from:
   i. a thymidine kinase (TK) mutation selected from 100C>T (HSV-1), 268C>T (HSV-2), 373C>T (HSV-1), 376C>T (HSV-2), 146T>G (HSV-1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>C (HSV-1), 938T>C (HSV-2), 437_438 insA (HSV-1), 169delC (HSV-1), 170delC (HSV-1), 171delC (HSV-1), 172delC (HSV-1), 276delG (HSV-2), 278delG (HSV-2), 279delG (HSV-2), 280delG (HSV-2), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1); and
   ii. a DNA polymerase (DNA pol) mutation selected from 1879C>G (HSV-1), 1882C>G (HSV-2), 2405T>G (HSV-1), 2420T>G (HSV-2), 2500G>T (HSV-1), 2515G>T (HSV-2), 2515A>G (HSV-1), 2530A>G (HSV-2), 2892_2893 insT (HSV-1), 2893_2894 insT (HSV-1), 2894_2895 insT (HSV-1), 2895_2896 insT (HSV-1), 2907_2908 insT (HSV-2), 2908_2909 T (HSV-2), 2909_2910 T (HSV-2), and 2910_2911 T (HSV-2);

wherein the presence of said one or more HSV mutation confirms (e.g. is indicative of) the presence of an infection with an antiviral drug-resistant HSV, and the absence of said one or more HSV mutation is indicative of (e.g. correlates with) the absence of an infection with an antiviral drug-resistant HSV.

In a preferable embodiment, said thymidine kinase (TK) mutation is selected from 250G>A (HSV-2), 100C>T (HSV-1), 268C>T (HSV-2), 373C>T (HSV-1), 146T>G (HSV-1), 363G>A (HSV-1), 497T>A (HSV-1), 558G>T (HSV-2), 641A>G (HSV-2), 715T>C (HSV-1), 938T>C (HSV-2), 437_438 insA (HSV-1), 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1). In a preferable embodiment, said DNA polymerase (DNA pol) mutation is selected from 1882C>G (HSV-2), 2405T>G (HSV-1), 2500G>T (HSV-1), 2515A>G (HSV-1), 2892_2893 insT (HSV-1), 2893_2894 insT (HSV-1), 2894_2895 insT (HSV-1), and 2895_2896insT (HSV-1).

The term "diagnosis" as used herein encompasses identification, confirmation and/or characterisation of an antiviral drug-resistant HSV infection. Methods of diagnosis according to the invention are useful to confirm the existence of an infection. Methods of diagnosis are also useful in methods for assessment of clinical screening, prognosis, choice of therapy, evaluation of therapeutic benefit, i.e. for drug screening and drug development. Efficient diagnosis allows rapid identification of the most appropriate treatment (thus lessening unnecessary exposure to harmful drug side effects), and reducing relapse rates.

TK and/or DNA pol mutations described herein also find utility in the detection of antiviral drug-resistant HSV in e.g. non-patient samples, such as those obtained from medical equipment, surgical devices, or environmental samples.

In one embodiment, the method comprises detecting the presence or absence of one or more of said HSV mutations in a database of HSV mutations (e.g. TK and/or DNA pol mutations) associated with antiviral drug resistance. Suitably, said database comprises the mutations described herein.

In a preferable embodiment, said database comprises phenotypic data associated with the HSV mutation, preferably wherein said data is data on the susceptibility and/or resistance of an HSV comprising a mutation described herein to an antiviral drug.

In another aspect, there is provided a method for determining prognosis of an infection with an antiviral drug-resistant HSV in a subject, comprising detecting the presence or absence of one or more HSV mutation described herein in a sample obtained from a subject. In such aspects, the presence of said one or more HSV mutation correlates with a poor prognosis, and the absence of said one or more HSV mutation correlates with a good prognosis.

The term "Herpes Simplex Virus" (HSV) as used herein suitably encompasses both HSV-1 and HSV-2. The TK and DNA pol genes are highly conserved across HSV-1 and HSV-2, such that a resistance-associated mutation in one virus may also cause resistance in the other virus when present in the corresponding position (e.g. the corresponding position of the polypeptide and/or nucleic acid sequence). Thus, in one embodiment the HSV is HSV-1. In another embodiment, the HSV is HSV-2.

The term "antiviral drug-resistant" means that the HSV demonstrates resistance to an antiviral drug which is typically used to treat an HSV infection. The term "resistant" encompasses both weak (e.g. intermediate) resistance and strong resistance to one or more antiviral drug. The presence of weak (intermediate) and/or strong resistance may be determined using a plaque reduction assay, as described below. The term "susceptible" (e.g. in the context of an "antiviral drug-susceptible HSV" means that the HSV is not resistant to one or more antiviral drug which is typically used to treat an HSV infection.

In a preferable embodiment, the antiviral drug is one or more selected from foscarnet, cidofovir, penciclovir and aciclovir, or a combination thereof.

In one embodiment, the antiviral drug is one or more selected from foscarnet, cidofovir, or a combination thereof.

In one embodiment, the antiviral drug is one or more selected from penciclovir and aciclovir, or a combination thereof.

In one embodiment, an antiviral drug resistant HSV has weak/intermediate resistance to an antiviral drug. In one embodiment, an antiviral drug resistant HSV has strong resistance to an antiviral drug.

An assessment of said "antiviral drug-resistance", is demonstrated by reference to the accompanying Examples, and may be assessed using the methodology described in the Examples (e.g. Example 2). For example, Example 3 describes a plaque reduction assay, which measures the "1050" of a drug against an HSV.

An assessment of "antiviral drug-resistance" can be made using a "plaque reduction assay" as is understood by the person skilled in the art. The plaque reduction assay may be carried out e.g. as described in Mbisa, Jean Lutamyo (September 2013), Antiviral Resistance Testing. In: eLS. John Wiley & Sons, Ltd: Chichester, which is incorporated herein by reference.

By way of example, a "plaque reduction assay" may comprise:

a. contacting a test sample and a control sample with defined concentration of a HSV, wherein the test sample and the control sample comprise a confluent monolayer of non-HSV infected cells (e.g. a confluent monolayer of cells which lack an HSV infection);
b. contacting the test sample with a defined concentration of an antiviral drug, either together with or subsequent to step a., incubating the test sample in the presence of the antiviral drug and incubating the control sample in the absence of an antiviral drug;
c. detecting the number of cells infected with an HSV in the test sample and in the control sample;
d. calculating the percentage of cells infected with an HSV in the test sample relative to the number of cells infected with an HSV in the control sample;
e. repeating steps (a)-(d), either simultaneously or separately, at least one time (e.g. 2, 3, 4, 5, 6, 7, 8, 9 or 10 times) with a lower defined concentration of the antiviral drug; and
f. calculating the $IC_{50}$ (or $IC_{20}$, $IC_{40}$, $IC_{60}$, $IC_{80}$ or $IC_{90}$) of the antiviral drug.

The "$IC_{50}$" value is the concentration of antiviral drug sufficient to reduce the percentage of cells infected with a HSV in the test sample relative to the number of cells infected with a HSV in the control sample by 50%. Likewise, the "1020", "1040", "1060", "1080" and "1090" values mean the concentration of antiviral drug sufficient to reduce the percentage of cells infected with a HSV in the test sample relative to the number of cells infected with a HSV in the control sample by 20%, 40%, 60%, 80% or 90%, respectively.

The test sample and the control sample are typically incubated at step b. for at least one hour (e.g. at least 2, 3, 4, 5, 6, 7, 8, 9, 10, 11, 12, 13, 14 or 15 hours).

The "lower defined concentration" of step e. is typically at least 2 times lower (e.g. at least 3, 4, 5, 6, 7, 8, 9, 10, 11, 12, 13, 14 or 15 times lower). Suitably each time steps a.-d. are repeated (i.e. in step e.), the defined concentration of the drug is lowered accordingly.

Certain $IC_{50}$ values of antiviral drugs correlate with certain levels of resistance, as outlined below.

Thus, in one embodiment a method of the invention comprises determining the level of resistance of a detected antiviral drug resistant HSV to an antiviral drug (e.g. strong resistance, weak/intermediate resistance, or no resistance/susceptibility). This can inform an appropriate choice of drug treatment and/or dosage of drug required for treatment. For example, where a mutation correlating with weak resistance is detected, a higher dose and/or longer course of treatment may be chosen.

The term "resistance phenotype" means the level of resistance of an HSV comprising a mutation described herein to an antiviral drug. Suitably, a resistance phenotype is selected from weak (e.g. intermediate) and strong resistance. Preferably, said resistance phenotype is determined via a plaque reduction assay.

In HSV infected cells, nucleoside analogue drugs (e.g. acyclovir and penciclovir) are phosphorylated by viral thymidine kinase and subsequently converted by cellular kinases into the active metabolite (e.g. acyclovir triphosphate and penciclovir triphosphate), which competitively inhibits viral HSV polymerase by competing with natural nucleoside (e.g. deoxyguanosine triphosphate) substrate binding. As a result, herpes viral DNA synthesis and replication are selectively inhibited. Without wishing to be bound by theory, it is believed that a TK enzyme comprising a mutation/polymorphism as described herein has reduced kinase activity, such that a nucleoside analogue drug (e.g. acyclovir and penciclovir) is not effectively phosphorylated (or is not phosphorylated at all) to produce an active drug. Thus, in one embodiment a TK comprising a TK mutation/polymorphism as described herein has reduced kinase (e.g. phosphorylation) activity. Suitably, a TK comprising a TK mutation/polymorphism as described herein does not phosphorylate a nucleoside analogue drug (e.g. acyclovir and penciclovir). Antiviral drugs which do not require phosphorylation by TK (e.g. cidofovir and foscarnet) are believed to directly inhibit viral DNA polymerase activity. Suitably, a DNA pol comprising a DNA pol mutation/polymorphism as described herein is not inhibited by an antiviral drug (e.g. cidofovir and foscarnet). Docosanol (PubChem CID: 12620) is a further antiviral drug used to treat HSV. The helicase-primase (e.g. of HSV-1) inhibitor BAY 54-6322 (Chemical Formula: $C_{20}H_{21}N_3O_3S_2$; IUPAC Name: N-methyl-N-[4-methyl-5-(methylsulfamoyl)-1,3-thiazol-2-yl]-2-(4-phenylphenyl)acetamide) is a further antiviral drug used to treat HSV. The helicase-primase (e.g. of HSV-1) inhibitor ASP2151, also known as Amenamevir (PubChem CID: 11397521; Molecular Formula: $C_{24}H_{26}N_4O_5S$) is a further antiviral drug used to treat HSV. The helicase-primase (e.g. of HSV-1) inhibitor BAY 57-1293, also known as pritelivir (PubChem CID: 491941; Molecular Formula: $C_{18}H_{18}N_4O_3S_2$) is a further antiviral drug used to treat HSV.

In one embodiment, the antiviral drug is acyclovir (PubChem CID: 2022; CAS Registry Number: 59277-89-3). In one embodiment, an antiviral-drug resistant HSV (e.g. HSV-1 or HSV-2) has strong resistance to acyclovir when the $IC_{50}$ of the drug is greater than 40 μM (e.g. greater than 50 μM, 65 μM, 80 μM, 95 μM, 110 μM, 125 μM or 140 μM). In one embodiment, an antiviral-drug resistant HSV-1 has weak (intermediate) resistance to acyclovir when the $IC_{50}$ of the drug is between about 3-40 μM (e.g. between about 6.5-40 μM, 5-35 μM, 10-30 μM, or 15-25 μM). In one embodiment, an antiviral-drug resistant HSV-2 has weak (intermediate) resistance to acyclovir when the $IC_{50}$ of the drug is between about 6.5-40 μM (e.g. between about 10-30 μM, or 15-25 μM). In one embodiment, a HSV-1 is susceptible (e.g. non-resistant) to acyclovir when the $IC_{50}$ is less than 3 μM (e.g. less than 2.5 μM, 2 μM, 1.5 μM, 1 μM or 0.5 μM). In one embodiment, a HSV-2 is susceptible (e.g. non-resistant) to acyclovir when the $IC_{50}$ is less than 6.5 μM (e.g. less than 5 μM, 4 μM, 3 μM, 2 μM or 1 μM). In a preferable embodiment, the $IC_{50}$ is determined in (e.g. via) a plaque reduction assay.

In one embodiment, the antiviral drug is penciclovir (PubChem CID: 4725; CAS Registry Number: 39809-25-1). In one embodiment, the antiviral-drug resistant HSV (e.g. HSV-1 or HSV-2) has strong resistance to pencyclovir when the $IC_{50}$ of the drug is greater than 40 μM (e.g. greater than 50 μM, 65 μM, 80 μM, 95 μM, 110 μM, 125 μM or 140 μM).

In one embodiment, an antiviral-drug resistant HSV-1 has weak (e.g. intermediate) resistance to pencyclovir when the $IC_{50}$ of the drug (e.g. as determined in a plaque reduction assay) is between about 10-40 μM (e.g. between about 15-35 μM, or 20-30 μM). In one embodiment, an antiviral-drug resistant HSV-2 has weak (e.g. intermediate) resistance to pencyclovir when the $IC_{50}$ of the drug is between about 38-40 μM (e.g. about 39 μM). In one embodiment, a HSV-1 is susceptible (e.g. non-resistant) to pencyclovir when the $IC_{50}$ is less than 10 μM (e.g. less than 8 μM, 6 μM, 4 μM, 2 μM or 0.5 μM). In one embodiment, a HSV-2 is susceptible (e.g. non-resistant) to pencyclovir when the $IC_{50}$ is less than 38 μM (e.g. less than 30 μM, 25 μM, 20 μM, 15 μM or 10 μM). In a preferable embodiment, the $IC_{50}$ is determined in (e.g. via) a plaque reduction assay.

In one embodiment, the antiviral drug is foscarnet (PubChem CID: 3415). In one embodiment, an antiviral-drug resistant HSV (e.g. HSV-1 or HSV-2) has strong resistance to foscarnet when the $IC_{50}$ of the drug is greater than 400 μM (e.g. greater than 450 μM, 500 μM, 550 μM, 600 μM, 650 μM, 700 μM or 750 μM). In one embodiment, the antiviral-drug resistant HSV (e.g. HSV-1 or HSV-2) has weak resistance to foscarnet when the $IC_{50}$ of the drug is between about 250-400 μM (e.g. between about 275-385 μM, 300-360 μM, or 325-335 μM). In one embodiment, a HSV is susceptible (e.g. non-resistant) to foscarnet when the $IC_{50}$ is less than 250 μM (e.g. less than 200 μM, 150 μM, 100 μM, 50 μM or 10 μM). In a preferable embodiment, the $IC_{50}$ is determined in (e.g. via) a plaque reduction assay.

In one embodiment, the antiviral drug is cidofovir (PubChem CID: 60613; CAS Registry Number: 113852-37-2). In one embodiment, an antiviral-drug resistant HSV (e.g. HSV-1 or HSV-2) has strong resistance to cidofovir when the $IC_{50}$ of the drug is greater than 30 μM (e.g. greater than 40 μM, 50 μM, 60 μM, 70 μM, 80 μM, 90 μM or 100 μM). In one embodiment, an antiviral-drug resistant HSV (e.g. HSV-1 or HSV-2) has weak resistance to cidofovir when the $IC_{50}$ of the drug is between about 24-30 μM (e.g. between about 25-29 μM, or 26-28 μM). In one embodiment, a HSV is susceptible (e.g. non-resistant) to cidofovir when the $IC_{50}$ is less than 24 μM (e.g. less than 20 μM, 15 μM, 10 μM, 5 μM or 1 μM). In a preferable embodiment, the $IC_{50}$ is determined in (e.g. via) a plaque reduction assay.

In a preferable embodiment, identifying the presence of a TK mutation described herein confirms the presence of a acyclovir and/or penciclovir drug-resistant HSV. Suitably, identifying the absence of a TK mutation described herein is indicative of the absence of a acyclovir and/or penciclovir drug-resistant HSV. In another preferable embodiment, identifying the presence of a DNA pol mutation described herein confirms the presence of a acyclovir, penciclovir, foscarnet and/or cidofovir resistant HSV. Suitably, identifying the absence of a DNA pol mutation described herein is indicative of the absence of acyclovir, penciclovir, foscarnet and/or cidofovir resistant HSV.

The terms "subject", "individual" and "patient" are used interchangeably herein to refer to a mammalian subject. In one embodiment the "subject" is a human, a companion animal (e.g. a pet such as dogs, cats, and rabbits), livestock (e.g. pigs, sheep, cattle, and goats), and horses. In a preferable embodiment, the subject is a human. Suitably, the subject (e.g. human) is immunocompromised. An immunocompromised subject may be a pregnant subject, a subject comprising an alternative infection (e.g. a HIV or meningococcal infection), or a haemato-oncology patient (e.g. undergoing bone-marrow transplant therapy). Suitably, the subject is a human undergoing bone-marrow transplant therapy. In methods of the invention, the subject may not have been previously diagnosed as having an HSV infection. Alternatively, the subject may have been previously diagnosed as having an HSV infection. The subject may also be one who exhibits disease risk factors, or one who is asymptomatic for an HSV infection. The subject may also be one who is suffering from or is at risk of developing an HSV infection. Thus, in one embodiment, a method of the invention may be used to confirm the presence of an HSV infection (e.g. an infection with an antiviral drug-resistant HSV) in a subject. For example, the subject may previously have been diagnosed with ASD through analysis of symptoms that the subject presents. In one embodiment, the subject has been previously administered an antiviral drug.

An "identifying" step (e.g. of one or more HSV mutation) may be performed manually, for example, by analysing a nucleic acid and/or polypeptide sequence. An identifying step may also be performed using any suitable method known in the art. A mutation may be identified within either the nucleic acid sequence or the polypeptide sequence. In one embodiment, DNA sequencing (e.g. of a PCR fragment/amplicon) may be used. In one embodiment, a TK sequence or fragment thereof is amplified. In one embodiment, a DNA pol sequence or fragment thereof is amplified. Said fragment may be of any length, and suitably encompasses the regions of the gene in which one or more of said mutations are present (and optionally includes 3' and/or 5' untranslated regions). Thus, in one embodiment a TK fragment (e.g. amplicon) comprises at least about 0.1 kilobases (kb), 0.2 kb, 0.3 kb, 0.4 kb, 0.5 kb, 0.6 kb, 0.7 kb, 0.8 kb, 0.9 kb, 1 kb, 1.1 kb, or 1.2 kb. In one embodiment, a DNA pol fragment (e.g. amplicon) comprises at least about 0.1 kilobases (kb), 0.2 kb, 0.3 kb, 0.4 kb, 0.5 kb, 0.6 kb, 0.7 kb, 0.8 kb, 0.9 kb, 1 kb, 1.1 kb, 1.2 kb, or 1.3 kb.

In another embodiment, the identifying step utilises a nucleic acid probe specific for one of more TK and/or DNA pol mutation (e.g. for use in PCR detection). In one embodiment, the identifying step is performed by mass spectrometry (e.g. to detect a polymorphism in a polypeptide sequence resulting from a mutation described herein). In another embodiment, the identifying step is performed by way of an immunoassay. Said immunoassay may employ the use of one or more antibodies that bind to one or more mutein(s) comprising a polymorphism described herein. Thus, in one aspect, there is provided an antibody composition for use in detecting one or more HSV mutation/polymorphism described herein. In another aspect, there is provided an antibody composition for use in the diagnosis of an infection with an antiviral-drug resistant HSV in a subject, wherein said antibody composition binds one or more mutein(s) comprising a polymorphism described herein. In another embodiment, the detecting step is performed by Western Blot or Enzyme activity assay. A method of the invention may comprise the use of a kit of the invention or a part thereof. For example, the method may comprise the use of a reagent described herein (preferably a nucleic acid PCR primer).

The methods or uses of the invention may encompass the detection of a HSV comprising a mutation described herein. The methods or uses of the invention may also encompass detecting no HSV comprising a mutation as described herein.

A method of the invention preferably involves the use of an algorithm or other data-driven combinatorial approach. In one embodiment, the identified mutations (e.g. TK and/or DNA pol mutations) are entered into an algorithm (e.g. as part of a computer software programme which may be provided in one aspect of the present invention), and said algorithm indicates whether an antiviral drug-resistant HSV is present, preferably by indicating whether the mutation is associated with antiviral drug resistance. In a preferable embodiment, said algorithm additionally indicates whether said mutation confers weak/intermediate or strong resistance to an antiviral drug.

In one embodiment, the algorithm interacts with a database comprising one or more HSV mutation. In a preferable embodiment, said database further comprises phenotypic data associated with one or more HSV mutation, preferably wherein said data is data on antiviral drug susceptibility/resistance. In one embodiment, the algorithm provides as an output the level (e.g. magnitude) of resistance associated with one or more HSV mutation, wherein said level of resistance is selected from one or more of weak/intermediate resistance, strong resistance and susceptibility (e.g. not resistant to one or more antiviral drug).

In one aspect, there is provided software adapted to provide an algorithm or diagnostic method of the invention. The invention also extends to a processor adapted to provide said software, algorithm and/or diagnostic method.

The skilled person will appreciate that any suitable algorithm can be used (including any one of the algorithms described herein). In one embodiment, the algorithm is an interpretation algorithm. In one embodiment, the algorithm is a machine learning algorithm. In one embodiment the algorithm is one or more selected from: Random Forests, logistic regression, ensemble classifier, Support Vector Machines (SVMs), general linear models (GLM), and GLMNET.

In one embodiment, the identifying (e.g. identification) steps of methods of the present invention comprise using a diagnostic algorithm configured to diagnose the presence or absence of an infection with an antiviral drug-resistant HSV (or to detect the presence or absence of an antiviral drug-resistant HSV), optionally wherein the diagnostic algorithm is trained on the mutations present in an antiviral drug-resistant HSV. In some embodiments, the algorithm predicts/provides the level of resistance (e.g. weak or strong resistance to an antiviral drug) associated with a mutation. Preferably, the algorithm is trained on the corresponding resistance phenotype for one or more of said mutation. Said embodiment can be applied to other methods such as the methods for determining prognosis.

Similar methods for identifying a therapy suitable for treating an antiviral drug-resistant HSV, and monitoring the efficacy of an antiviral drug-resistant HSV infection therapy are also provided.

In embodiments related to methods for identifying a therapy for an antiviral drug-resistant HSV, a candidate therapeutic is identified as suitable for treating an antiviral drug-resistant HSV infection when the viral load of said HSV comprising said one or more mutation in the test sample is lower than the viral load of a HSV comprising said one or more mutation in a control sample, wherein the control is incubated in the absence of an antiviral drug; and/or said candidate therapy is identified as not suitable for treating an antiviral drug-resistant HSV infection when the viral load of said HSV comprising said one or more mutation in the test sample is the same as (or greater than) the viral load of a HSV comprising said one or more mutation in a control sample, wherein the control is incubated in the absence of an antiviral drug.

A "sample" for use in the present invention is any sample that could comprises a HSV (e.g. antiviral drug-resistant HSV) or fragment thereof. Suitably, said sample may be isolated from a subject suspected of having an infection with an antiviral-drug resistant HSV. In some embodiments, the sample is isolated from a subject diagnosed as having an HSV infection. Suitably, a sample may be selected from one or more of a lesion, bodily fluid isolated from a lesion, blood, urine, eye fluid, lymphatic fluid, saliva, synovial fluid, seminal fluid, cerebrospinal fluid, sebaceous secretions, and/or sputum. In one embodiment, the sample is a viral suspension, optionally suspended in a suitable viral transport medium (e.g. Universal Transport Medium from Copan). In one embodiment, the sample is obtained from surgical or other medical equipment. In one embodiment, the sample is an environmental sample (e.g. water, soil and/or sediment).

Preferably the sample is a lesion (e.g. herpetic lesion) or fragment thereof. The term "lesion" encompasses any abnormality of tissue and/or an organ present in a subject having or suspected of having a HSV infection. Suitably, the sample is bodily fluid isolated from a lesion.

A key advantage to using a lesion or fragment thereof in methods of the present invention is that these sample are readily obtainable from a subject suspected of having an infection with an antiviral-drug resistant HSV and can be obtained using minimally invasive techniques (e.g. by contacting the lesion with a swab or other collecting device).

In one embodiment, a sample may be processed to isolate an HSV from a sample prior to detecting the presence or absence of an HSV comprising a mutation as described herein. In a preferable embodiment, the HSV is cultured from a sample prior to a detecting step of methods of the invention. In another embodiment, the viral genome or fragment thereof is first amplified and subsequently inserted (e.g. ligated) into a suitable vector (e.g. via restriction enzymes or by homologous recombination). The recombinant vectors may be introduced into cells by transfection to produce recombinant HSV.

In one embodiment, the sample comprises a recombinant (e.g. in vitro recombinant) HSV. Suitably, a recombinant HSV comprises one or more mutations/polymorphisms (e.g. TK and/or DNA pol mutations/polymorphisms) described herein.

In one aspect there is provided a recombinant (e.g. in vitro recombinant) HSV (e.g. HSV-1 and/or HSV-2) or fragment thereof comprising a mutation selected from: (i) a TK mutation selected from 100C>T (HSV-1), 268C>T (HSV-2), 373C>T (HSV-1), 376C>T (HSV-2), 146T>G (HSV-1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>C (HSV-1), 938T>C (HSV-2), 437_438 insA (HSV-1), 169delC (HSV-1), 170delC (HSV-1), 171delC (HSV-1), 172delC (HSV-1), 276delG (HSV-2), 278delG (HSV-2), 279delG (HSV-2), 280delG (HSV-2), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1); and (ii) a DNA pol mutation selected from 1879C>G (HSV-1), 1882C>G (HSV-2), 2405T>G (HSV-1), 2420T>G (HSV-2), 2500G>T (HSV-1), 2515G>T (HSV-2), 2515A>G (HSV-1), 2530A>G (HSV-2), 2892_2893 insT (HSV-1), 2893_2894 insT (HSV-1), 2894_2895 insT (HSV-1), 2895_2896 insT, 2907_2908 insT (HSV-2), 2908_2909 insT (HSV-2), 2909_2910 insT (HSV-2) and 2910_2911 insT (HSV-2).

In a preferable embodiment, said thymidine kinase (TK) mutation is selected from 250G>A (HSV-2), 100C>T (HSV-1), 268C>T (HSV-2), 373C>T (HSV-1), 146T>G (HSV-1), 363G>A (HSV-1), 497T>A (HSV-1), 558G>T (HSV-2), 641A>G (HSV-2), 715T>C (HSV-1), 938T>C (HSV-2), 437_438 insA (HSV-1), 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1). In a preferable embodiment, said DNA polymerase (DNA pol) mutation is selected from 1882C>G (HSV-2), 2405T>G (HSV-1), 2500G>T (HSV-1), 2515A>G (HSV-1), 2892_2893 insT (HSV-1), 2893_2894 insT (HSV-1), 2894_2895 insT (HSV-1), and 2895_2896 insT (HSV-1).

As used herein, the term "mutation" refers to any change in a nucleic acid, preferably relative to a reference sequence. Suitably, a mutation reduces (e.g. prevents) the interaction between TK and/or DNA pol polypeptide encoded thereby with an antiviral drug. The term "polymorphism" refers to any change in the polypeptide sequence, preferably relative to a reference sequence. Suitably, a polymorphism reduces (e.g. prevents) the interaction between TK and/or DNA pol with an antiviral drug.

In one embodiment, the mutation is a single nucleotide polymorphism (SNP).

In one embodiment, a TK SNP is selected from 100C>T (HSV-1), 268C>T (HSV-2), 3730>T (HSV-1), 376C>T (HSV-2), 146T>G (HSV-1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>C (HSV-1), and 938T>C (HSV-2). In one embodiment, a DNA pol SNP is selected from 18790>G (HSV-1), 18820>G (HSV-2), 2405T>G (HSV-1), 2420T>G (HSV-2), 2500G>T (HSV-1), 2515G>T (HSV-2), 2515A>G (HSV-1), and 2530A>G (HSV-2). In one embodiment, a TK SNP is selected from 1000>T (HSV-1), 268C>T (HSV-2), 373C>T (HSV-1), 376C>T (HSV-2), 146T>G (HSV-1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>C (HSV-1), and 938T>C (HSV-2); and a DNA pol SNP is selected from 18790>G (HSV-1), 18820>G (HSV-2), 2405T>G (HSV-1), 2420T>G (HSV-2), 2500G>T (HSV-1), 2515G>T (HSV-2), 2515A>G (HSV-1), and 2530A>G (HSV-2). In a preferably embodiment, a TK SNP is selected from 250G>A (HSV-2), 100C>T (HSV-1), 268C>T (HSV-2), 373C>T (HSV-1), 146T>G (HSV-1), 363G>A (HSV-1), 497T>A (HSV-1), 558G>T (HSV-2), 641A>G (HSV-2), 715T>C (HSV-1), and 938T>C (HSV-2). The skilled person understands that the sign ">" means that the first nucleotide referred to is substituted with/for the second nucleotide referred to at the position referred to. For example, where the substitution mutation is 100C>T (HSV-1), this means that the cytosine ("C") at position 100 (nucleotide number 100) of the TK nucleic acid sequence is substituted for thymine ("T").

In one embodiment, the mutation is an insertion (e.g. of one or more nucleotides).

In one embodiment, a TK insertion is 437_438 insA (HSV-1). In one embodiment, a DNA pol insertion is one or more selected from 2892_2893 insT (HSV-1), 2893_2894 insT (HSV-1), 2894_2895 insT (HSV-1), 2895_2896 insT (HSV-1), 2907_2908 insT (HSV-2), 2908_2909 insT (HSV-2), 2909_2910 T (HSV-2), and 2910_2911 T (HSV-2) (preferably 2892_2893 insT (HSV-1), 2893_2894 insT (HSV-1), 2894_2895 insT (HSV-1), and/or 2895_2896 insT (HSV-1)). In one embodiment, a TK insertion is 437_438 insA (HSV-1); and a DNA pol insertion is one or more selected from 2892_2893 insT (HSV-1), 2893_2894 insT (HSV-1), 2894_2895 insT (HSV-1), 2895_2895 insT (HSV-1), 2907_2908 insT (HSV-2), 2908_2909 insT (HSV-2), 2909_2910 insT (HSV-2) and 2910_2911 insT (HSV-2) (preferably 2892_2893 insT (HSV-1), 2893_2894 insT (HSV-1), 2894_2895 insT (HSV-1), and/or 2895_2896 insT (HSV-1)). The skilled person understands that the sign "ins" as used herein in the context of an insertion mutation means that a nucleotide(s) is inserted within the TK/DNA pol nucleic acid sequence between the positions referred to. For example, where the TK insertion mutation is 437_438 insA, this means that the nucleotide adenine ("A") has been inserted after position 437 of the TK nucleic acid sequence (with said "A" now occupying position 438 of the mutated nucleic acid sequence).

In one embodiment, the mutation is a deletion (e.g. of one or more nucleotides).

In one embodiment, a TK deletion is selected from 169delC (HSV-1), 170delC (HSV-1), 171delC (HSV-1), 172delC (HSV-1), 276delG (HSV-2), 278delG (HSV-2), 279delG (HSV-2), 290delG (HSV-2), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1) (preferably 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and/or 885delC (HSV-1)). The skilled person understands the sign "del" as used herein in the context of a deletion polymorphism means that a nucleotide is deleted from the TK/DNA pol nucleic acid sequence at the position(s) referred to. For example, where the deletion mutation is 169delC, this means the cytosine ("C") base has been deleted from position 169 of the TK nucleic acid sequence.

In one embodiment, the mutation causes a stop codon (e.g. early stop codon).

In one embodiment, a TK mutation causing a stop codon is selected from 100C>T (HSV-1), 268C>T (HSV-2), 373C>T (HSV-1), 376C>T (HSV-2), 169delC (HSV-1), 170delC (HSV-1), 171delC (HSV-1), 172delC (HSV-1), 437_438 insA (HSV-1), 276delG (HSV-2), 278delG (HSV-2), 279delG (HSV-2), 280delG (HSV-2), 458delC (HSV-2), 459delC (HSV-2), 460delC (HSV-2), and 461delC (HSV-2) (preferably 100C>T (HSV-1), 268C>T (HSV-2), 3730>T (HSV-1), 169delC (HSV-1), 170delC (HSV-1), 171delC (HSV-1), 172delC (HSV-1), 437_438 insA (HSV-1), 458delC (HSV-2), 459delC (HSV-2), 460delC (HSV-2), and/or 461delC (HSV-2)). In one embodiment, a DNA pol mutation causing a stop codon (e.g. early stop codon) is selected from 2892_2893 insT (HSV-1), 2893_2894 insT (HSV-1), 2894_2895 insT (HSV-1) and 2895_2896 insT. In one embodiment, a TK mutation causing a stop codon is selected from 100C>T (HSV-1), 268C>T (HSV-2), 373C>T (HSV-1), 3760>T (HSV-2), 169delC (HSV-1), 170delC (HSV-1), 171delC (HSV-1), 172delC (HSV-1), 437_438 insA, 276delG (HSV-2), 278delG (HSV-2), 279delG (HSV-2), 280delG (HSV-2), 458delC (HSV-2), 459delC (HSV-2), 460delC (HSV-2), and 461delC (HSV-2) (preferably 100C>T (HSV-1), 268C>T (HSV-2), 373C>T (HSV-1), 169delC (HSV-1), 170delC (HSV-1), 171delC (HSV-1), 172delC (HSV-1), 437_438 insA (HSV-1), 458delC (HSV-2), 459delC (HSV-2), 460delC (HSV-2), and/or 461delC (HSV-2)); and a DNA pol mutation causing a stop codon is selected from 2892_2893 insT (HSV-1), 2893_2894 insT (HSV-1), 2894_2895insT (HSV-1), and 2895_2896insT (HSV-1).

In one embodiment, the mutation causes a substitution polymorphism (e.g. an amino acid substitution) in the TK or DNA pol polypeptide sequence.

In one embodiment, a TK mutation causing a substitution polymorphism is selected from 146T>G (HSV-1), 363G>A (HSV-1), 366G>A (HSV-2), 497T>A (HSV-1), 500T>A (HSV-2), 715T>C (HSV-1), 718T>C (HSV-2), 250G>A (HSV-2), 253A>C (HSV-1), 256A>C (HSV-2), 558G>T (HSV-2), 935T>C (HSV-1), and 938T>C (HSV-2) (preferably 146T>G (HSV-1), 363G>A (HSV-1), 497T>A (HSV-1), 715T>C (HSV-1), 250G>A (HSV-2), 558G>T (HSV-2), and/or 938T>C (HSV-2). In one embodiment, a DNA pol mutation causing a substitution polymorphism is selected from 18790>G (HSV-1), 18820>G (HSV-2), 2405T>G (HSV-1), 2420T>G (HSV-2), 2500G>T (HSV-1), 2515G>T (HSV-2), 2515A>G (HSV-1), and 2530A>G (HSV-2) (preferably 18820>G (HSV-2), 2405T>G (HSV-1), 2500G>T (HSV-1), and/or 2515A>G (HSV-1)). In one embodiment, a TK mutation causing a substitution polymorphism is selected from 146T>G (HSV-1), 363G>A (HSV-1), 366G>A (HSV-2), 497T>A (HSV-1), 500T>A (HSV-2), 715T>C (HSV-1), 718T>C (HSV-2), 250G>A (HSV-2), 253A>C (HSV-1), 256A>C (HSV-2), 558G>T (HSV-2), 935T>C (HSV-1), and 938T>C (HSV-2) (preferably 146T>G (HSV-1), 363G>A (HSV-1), 497T>A (HSV-1), 715T>C (HSV-1), 250G>A (HSV-2), 558G>T (HSV-2), and/or 938T>C (HSV-2); and a DNA pol mutation causing a substitution polymorphism is selected from 18790>G (HSV-1), 18820>G (HSV-2), 2405T>G (HSV-1), 2420T>G (HSV-2), 2500G>T (HSV-1), 2515G>T (HSV-2), 2515A>G (HSV-1), and 2530A>G (HSV-2) (preferably 18820>G (HSV-2), 2405T>G (HSV-1), 2500G>T (HSV-1), and/or 2515A>G (HSV-1)).

In one embodiment, the mutation causes a frameshift (e.g. in the remainder of the coding sequence). In one embodiment, a TK mutation causing a frameshift is selected from 437_438 insA (HSV-1), 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1)), In one embodiment, a TK mutation causing a frameshift is selected from 881delC (HSV-1), 882delC (HSV-1), 883delC (HSV-1), 884delC (HSV-1), and 885delC (HSV-1).

In one embodiment, an HSV-1 TK mutation is one or more selected from 100C>T, 373C>T, 146T>G, 253A>C, 363G>A, 497T>A, 715T>C, 935T>C, 437_438 insA, 169delC, 170delC, 171delC, 172delC, 881delC, 882delC, 883delC, 884delC, and 885delC (preferably 100C>T, 373C>T, 146T>G, 363G>A, 497T>A, 715T>C, 437_438 insA, 169delC, 170delC, 171delC, 172delC, 881delC, 882delC, 883delC, 884delC, and/or 885delC). In one embodiment, an HSV-1 TK mutation is one or more selected from 100C>T, 146T>G, 363G>A, 373C>T, 497T>A, 715T>C, 169delC, 170delC, 171delC, 172delC, 437_438 insA, 881delC, 882delC, 883delC, 884delC, and 885delC. In one embodiment, an HSV-1 TK mutation is one or more selected from 146T>G, 497T>A, 169delC, 170delC, 171delC, 172delC, 437_438 insA, 881delC, 882delC, 883delC, 884delC, and 885delC.

In one embodiment, an HSV-2 TK mutation is one or more selected from 268C>T, 376C>T, 250G>A, 256A>C, 366G>A, 500T>A, 558G>T, 718T>C, 938T>C, 276delG, 278delG, 279delG, 280delG, 458delC, 459delC, 460delC, and 461delC (preferably 268C>T, 250G>A, 558G>T, 938T>C, 458delC, 459delC, 460delC, and/or 461delC). In one embodiment, an HSV-2 TK mutation is one or more selected from 250G>A, 256A>C, 268C>T, 558G>T, 938T>C, 1094C>T, 276delG, 278delG, 279delG, 280delG, 458delC, 459delC, 460delC, and 461delC (preferably 250G>A, 268C>T, 558G>T, 938T>C, 458delC, 459delC, 460delC, and/or 461delC). In one embodiment, an HSV-2 TK mutation is one or more selected from 256A>C, 558G>T, 938T>C, 1094C>T, 276delG, 278delG, and 279delG (preferably 558G>T, and/or 938T>C).

In one embodiment, a TK mutation is one or more selected from 100C>T, 373C>T, 146T>G, 253A>C, 363G>A, 497T>A, 715T>C, 935T>C, 437_438 insA, 169delC, 170delC, 171delC, 172delC, 881delC, 882delC, 883delC, 884delC, and 885delC (preferably 100C>T, 373C>T, 146T>G, 363G>A, 497T>A, 715T>C, 437_438 insA, 169delC, 170delC, 171delC, 172delC, 881delC, 882delC, 883delC, 884delC, and/or 885delC) wherein the HSV is HSV-1 and the TK mutation is one or more selected from 268C>T, 376C>T, 250G>A, 256A>C, 366G>A, 500T>A, 558G>T, 718T>C, 938T>C, 276delG, 278delG, 279delG, 280delG, 458delC, 459delC, 460delC, and 461delC (preferably 268C>T, 250G>A, 558G>T, 938T>C, 458delC, 459delC, 460delC, and/or 461delC) wherein the HSV is HSV-2.

In one embodiment, a HSV-1 DNA pol mutation is one or more selected from 1879C>G, 2405T>G, 2500G>T, 2515A>G, 2892_2893 insT, 2893_2894 insT, 2894_2895 insT, and 2895_2896 insT (preferably 2405T>G, 2500G>T, 2515A>G, 2892_2893 insT, 2893_2894 insT, 2894_2895 insT, and/or 2895_2896 insT). In one embodiment, an HSV-1 DNA pol mutation is one or more selected from 2405T>G, 2500G>T, 2515A>G, 2892_2893 insT, 2893_2894 insT, 2894_2895 insT, and 2895_2896 insT. In one embodiment, an HSV-1 DNA pol mutation is one or more selected from 2500G>T, 2515A>G, 2892_2893 insT, 2893_2894 insT, 2894_2895 insT, and 2895_2896 insT.

In one embodiment, a HSV-2 DNA pol mutation is one or more selected from 18820>G, 2420T>G, 2515G>T, 2530A>G, 2907_2908 insT, 2908_2909 insT, 2909_2910 insT, and 2910_2911insT (preferably 18820>G). In one embodiment, a HSV-2 DNA pol mutation is one or more selected from 2420T>G, 2515G>T, 2530A>G, 2907_2908 insT, 2908_2909 insT, 2909_2910insT, 2910_2911insT. In one embodiment, an HSV-2 DNA pol mutation is 18820>G.

In one embodiment, the DNA pol mutation is one or more selected from 18790>G, 2405T>G, 2500G>T, 2515A>G, 2892_2893 insT, 2893_2894 insT, 2894_2895 insT, and 2895_2896 insT preferably 2405T>G, 2500G>T, 2515A>G, 2892_2893 insT, 2893_2894 insT, 2894_2895 insT, and/or 2895_2896 insT) wherein the HSV is HSV-1 and the DNA pol mutation is one or more selected from 18820>G, 2420T>G, 2515G>T, 2530A>G, 2907_2908 insT, 2908_2909 insT, 2909_2910insT and 2910_2911insT (preferably 18820>G) wherein the HSV is HSV-2.

An HSV comprising said one or more mutation and/or may be referred to as a modified HSV, having a modified nucleic acid and/or amino acid sequence relative to a reference (wild-type) HSV sequence.

In a preferable embodiment, one or more (preferably all) of the mutations described herein are not present in a reference (e.g. wild-type) HSV sequence. Preferably, a HSV (e.g. HSV-1 or HSV-2) comprising the reference sequence is not resistant to an antiviral drug as described herein. The nucleic acid and polypeptide sequences of preferable reference HSV sequences are publically available. In one embodiment, the reference HSV-1 sequence (e.g. publically available sequence) is accessible on GenBank with accession number JN555585.1. The TK nucleic acid sequence, the TK polypeptide sequence, the DNA pol nucleic sequence and the DNA pol polypeptide sequence of this HSV-1 sequence corresponds to SEQ ID NO: 1, SEQ ID NO: 2, SEQ ID NO: 3, SEQ ID NO: 4, respectively. In one embodiment, the reference HSV-2 sequence (e.g. publically available sequence) is accessible on GenBank with accession number JN561323.2. The TK nucleic acid sequence, the TK polypeptide sequence, the DNA pol nucleic acid sequence and the DNA pol polypeptide sequence of this HSV-2 sequence corresponds to SEQ ID NO: 5, SEQ ID NO: 6, SEQ ID NO: 7, SEQ ID NO: 8, respectively.

In one embodiment, a reference HSV-1 TK nucleic acid comprises (or consists of) the sequence of SEQ ID NO: 1, or a sequence having at least 90% sequence identity thereto, suitably at least 91%, 92%, 93%, 94%, 95%, 96%, 97%, 98%, or 99% sequence identity thereto. In one embodiment, a reference HSV-1 TK polypeptide comprises (or consists of) the sequence of SEQ ID NO: 2, or a sequence having at least 90% sequence identity thereto, suitably at least 91%, 92%, 93%, 94%, 95%, 96%, 97%, 98%, or 99% sequence identity thereto. In one embodiment, a reference HSV-1 DNA pol nucleic acid comprises (or consists of) the sequence of SEQ ID NO: 3, or a sequence having at least 90% sequence identity thereto, suitably at least 91%, 92%, 93%, 94%, 95%, 96%, 97%, 98%, or 99% sequence identity thereto. In one embodiment, a reference HSV-1 DNA pol polypeptide comprises (or consists of) the sequence of SEQ ID NO: 4, or a sequence having at least 90% sequence identity thereto, suitably at least 91%, 92%, 93%, 94%, 95%, 96%, 97%, 98%, or 99% sequence identity thereto. In one embodiment, a reference HSV-2 TK nucleic acid comprises (or consists of) the sequence of SEQ ID NO: 5, or a sequence having at least 90% sequence identity thereto, suitably at least 91%, 92%, 93%, 94%, 95%, 96%, 97%, 98%, or 99% sequence identity thereto. In one embodiment, a reference HSV-2 TK polypeptide comprises (or consists of) the sequence of SEQ ID NO: 6, or a sequence having at least 90% sequence identity thereto, suitably at least 91%, 92%, 93%, 94%, 95%, 96%, 97%, 98%, or 99% sequence identity thereto. In one embodiment, a reference HSV-2 DNA pol nucleic acid comprises (or consists of) the sequence of SEQ ID NO: 7, or a sequence having at least 90% sequence identity thereto, suitably at least 91%, 92%, 93%, 94%, 95%, 96%, 97%, 98%, or 99% sequence identity thereto. In one embodiment, a reference HSV-2 DNA pol polypeptide comprises (or consists of) the sequence of SEQ ID NO: 8, or a sequence having at least 90% sequence identity thereto, suitably at least 91%, 92%, 93%, 94%, 95%, 96%, 97%, 98%, or 99% sequence identity thereto.

A reference HSV-1 TK polypeptide may comprise the sequence obtainable with a UniProt accession number selected from G8HBD6, C0L307, C0L309, A0A0U2UZK2, 12FEY2, C0L308, K4JR12, and C0L314. A reference HSV-1 DNA pol polypeptide may comprise the sequence obtainable with a UniProt accession number selected from G8HBE4, E1B1U3, P04293, I1YAD1, I1YAC1, 11YA98, A0A1C3K996, and E1B1Y8. A reference HSV-2 TK polypeptide may comprise the sequence obtainable with a UniProt accession number selected from P89446, Q6L709, E1B1R4, E1B1Y2, A0A0B4WW69, A0A0K0KND3, E1B1Y1, and A0A0B4WUV0. A reference HSV-2 DNA pol polypeptide may comprise the sequence obtainable with a UniProt accession number selected from P89453, E1B1W8, E1B202, E1B1X6, E1B212, A0A1U9ZMP4, A0A1U9ZLW2, I1YAG2 and A0A0K0KNB4.

The reference HSV sequence may be obtained either within (i.e. constituting a step of) or externally to methods of the invention. In one embodiment, the methods of the invention comprise a step of obtaining a reference HSV sequence, preferably wherein the reference HSV sequence is the sequence of a HSV which is not resistant to an antiviral drug described herein. In one embodiment, the reference HSV sequence is/are obtained externally to the method of the invention and accessed during the detecting and/or identifying step of the present invention.

In one embodiment, the term "at least one" when used in the context of a TK mutation described herein means at least 1, 2, 3, 4, 5, 6, 7, 8, 9, 10, 11, 10, 12, 13, 14, 15, 16, 17, 18, 19, 20, 21, 22 or all of the TK polymorphisms. In one embodiment, the term "at least one" when used in the context of a DNA pol mutation described herein means at least 1, 2, 3, 4, 5, 6, 7, 8, 9, 10, 11, 10, or all of the DNA pol mutations.

A mutation causing antiviral drug resistance as described herein is distinct from "mutation not associated with antiviral drug resistance" (e.g. a "non-antiviral drug resistance associated mutation" or "non-antiviral drug resistance associated polymorphism") which does not cause antiviral drug resistance. A HSV may comprise a multitude of "mutations not associated with antiviral drug resistance", many of which occur naturally and do not alter the structure and/or function of HSV polypeptides. The present inventors have identified a number of 'natural' mutations i.e. non-antiviral drug resistance associated. Furthermore, the present inventors have elucidated the phenotype of an HSV comprising one or more of said "mutations not associated with antiviral drug resistance", namely susceptibility to an antiviral drug. A "mutation not associated with antiviral drug resistance" as described herein is one which does not result in resistance to an antiviral drug. Advantageously, the detection of such 'natural' polymorphism increases the robustness of the interpretation of a resistance-associated mutation (e.g. the interpretation of a database of resistance associated mutations, and algorithm for their detection). Advantageously, by providing such 'natural' polymorphisms, the present invention avoids the problem of false-positive detection of antiviral drug resistance.

A mutation not associated with antiviral drug resistance in the TK sequence of HSV-1 (with the corresponding/resulting amino acid substitution shown in parentheses) may be one or more selected from 110C>T (A37V), 205C>A (L69M), 1072A>C or 1072A>T (1358L), 574G>A (A192T), 766C>T (R256W).

A mutation not associated with antiviral drug resistance in the TK sequence of HSV-2 (with the corresponding/resulting amino acid substitution shown in parentheses) may be one or more selected from 100C>T (R34C), 373G>A (A125T), 639A>C or 639A>T (E213D), or 1094T>C (L365P) (preferably 373G>A, 639A>C or 639A>T, or 1094T>C).

A mutation not associated with antiviral drug resistance in the DNA pol sequence of HSV-1 (with the corresponding/resulting amino acid substitution shown in parentheses) may be one or more selected from 64G>A (G22R), 160A>G (T54A), 248A>C (D83A), 361G>A (G121S), 415G>A or 415G>C (G139R), 716C>T (S239L), 1255C>A (L419I), 2039A>C (E680A), 2042G>A (R681Q), 2249A>C (K750T), 2548G>C (E850Q), 2732G>A (S911N), 2741C>T (S914L), 2915C>T (A972V), 2954G>A (G985E), 2974G>A (E992K), 2977C>T (R993C), 3137A>C (N1046T), 3343G>A (A1115T), 3359A>C (E1120A), 3505G>A (A1169T), and 3595C>A (P1199T).

A mutation not associated with antiviral drug resistance in the DNA pol sequence of HSV-2 (with the corresponding/resulting amino acid substitution shown in parentheses) may be one or more selected from 520G>T (D174Y), 1339A>C or 1339A>T (M447L), 1481T>C (M494T), 2141A>G (H714R), 2281G>A (E761K), 2323C>T (R775C), 2325C>G (R775W), and 2326G>C (E776Q).

Alternatively or additionally (preferably additionally), a method of the invention comprises:

a. identifying one or more HSV-1 TK mutation (e.g. natural mutation) selected from: 110C>T, 205C>A, 1072A>C, 1072A>T, 574G>A, and 766C>T;
b. identifying one or more HSV-2 TK mutation (e.g. natural mutation) selected from: 100C>T, 373G>A, 639A>C or 639A>T, and 1094T>C (preferably 373G>A, 639A>C or 639A>T, or 1094T>C);
c. identifying one or more HSV-1 DNA Pol mutation (e.g. natural mutation) selected from: 64G>A, 160A>G, 248A>C, 361G>A, 415G>A or 415G>C, 716C>T, 1255C>A, 2039A>C, 2042G>A, 2249A>C, 2548G>C, 2732G>A, 2741C>T, 2915C>T, 2954G>A, 2974G>A, 2977C>T, 3137A>C, 3343G>A, 3359A>C, 3505G>A, and 3595C>A; and/or
d. identifying one or more HSV-2 DNA Pol mutation (e.g. natural mutation) selected from: 520G>T, 1339A>C or 1339A>T, 1481T>C, 2141A>G, 2281G>A, 2323C>T, 2325C>G, and 2326G>C;
wherein the presence of said one or more HSV mutation is indicative of the absence of an antiviral drug-resistant HSV.

Alternatively or additionally (preferably additionally), a method of the invention comprises:

a. identifying one or more HSV-1 TK polymorphism (e.g. natural polymorphism) selected from: A37V, L69M, 1358L, A192T, and R256W;
b. identifying one or more HSV-2 TK polymorphism (e.g. natural polymorphism) selected from: R34C, A125T, E213D, and L365P (preferably A125T, E213D, or L365P);
c. identifying one or more HSV-1 DNA Pol polymorphism (e.g. natural polymorphism) selected from: G22R, T54A, D83A, G121S, G139R, S239L, L4191, E680A, R681Q, K750T, E850Q, S911N, S914L, A972V, G985E, E992K, R993C, N1046T, A1115T, E1120A, A1169T, and P1199T; and/or d. identifying one or more HSV-2 DNA Pol polymorphism (e.g. natural polymorphism) selected from: D174Y, M447L, M494T, H714R, E761K, R775C, R775W, and E776Q; wherein the presence of said one or more HSV polymorphism is indicative of the absence of an antiviral drug-resistant HSV.

In one aspect, the invention provides a method for identifying a therapeutic suitable for treating an antiviral drug-resistant HSV (e.g. HSV-1 and/or HSV-2) infection, comprising:

a. incubating a test sample in the presence of a candidate therapeutic, wherein said test sample comprises a HSV comprising one or more mutation selected from (i) a TK mutation is selected from 100C>T (HSV-1), 268C>T (HSV-2), 373C>T (HSV-1), 376C>T (HSV-2), 146T>G (HSV-1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>C (HSV-1), 938T>C (HSV-2), 437_438 insA (HSV-1), 169delC (HSV-1), 170delC (HSV-1), 171delC (HSV-1), 172delC (HSV-1), 276delG (HSV-2), 278delG (HSV-2), 279delG (HSV-2), 280delG (HSV-2), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1); and (ii) a DNA pol mutation selected from 18790>G (HSV-1), 18820>G (HSV-2), 2405T>G (HSV-1), 2420T>G (HSV-2), 2500G>T (HSV-1), 2515G>T (HSV-2), 2515A>G (HSV-1), 2530A>G (HSV-2), 2892_2893 insT (HSV-1), 2893_2894 insT (HSV-1), 2894_2895 insT (HSV-1), 2895_2896 insT (HSV-1), 2907_2908 insT (HSV-2), 2908_2909 insT (HSV-2), 2909_2910 insT (HSV-2), and 2910_2911 insT (HSV-2);
b. identifying said candidate therapeutic as suitable for treating an antiviral drug-resistant HSV infection when the viral load of said HSV comprising said one or more mutation in the test sample is lower than the viral load of a HSV comprising said one or more mutation in a control sample, wherein the control sample is incubated in the absence of an antiviral drug; or
c. identifying said candidate therapeutic as not suitable for treating an antiviral drug-resistant HSV infection when the viral load of said HSV comprising said one or more mutation in the test sample is the same as (or greater than) the viral load of a HSV comprising said one or more mutation in a control sample, wherein the control sample is incubated in the absence of an antiviral drug.

In a preferable embodiment, said thymidine kinase (TK) mutation is selected from 250G>A (HSV-2), 100C>T (HSV-1), 268C>T (HSV-2), 373C>T (HSV-1), 146T>G (HSV-1), 363G>A (HSV-1), 497T>A (HSV-1), 558G>T (HSV-2), 641A>G (HSV-2), 715T>C (HSV-1), 938T>C (HSV-2), 437_438 insA (HSV-1), 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1). In a preferable embodiment, said DNA polymerase (DNA pol) mutation is selected from 1882C>G (HSV-2), 2405T>G (HSV-1), 2500G>T (HSV-1), 2515A>G (HSV-1), 2892_2893 insT (HSV-1), 2893_2894 insT (HSV-1), 2894_2895 insT (HSV-1), and 2895_2896insT (HSV-1).

The skilled person understands that where the methods of the invention comprise a comparison step between two samples (e.g. between a "test sample" and a "control sample") that conditions (e.g. assay conditions during the method) should be kept consistent. For example, the viral load (e.g. starting viral load) of the HSV in both the test sample and control sample should be the same, as should culture conditions, etc.

The viral load of a HSV comprising said one or more mutation in a control sample may be determined either within (i.e. constituting a step of) or externally to methods of the invention. In one embodiment, the methods of the invention comprise a step of incubating a control sample in the absence of an antiviral drug. In one embodiment, the concentration of a HSV comprising said one or more mutation in a control sample is obtained externally to the method of the invention and accessed during the comparison step of the present invention.

Another aspect provides a method for monitoring the efficacy of an HSV therapy in a subject infected with an antiviral drug-resistant HSV (e.g. HSV-1 and/or HSV-2), said method comprising:

a. providing an isolated sample from a patient administered said therapy;
b. detecting the concentration of a HSV comprising said one or more mutation selected from: (i) a TK mutation selected from 100C>T (HSV-1), 268C>T (HSV-2), 373C>T (HSV-1), 376C>T (HSV-2), 146T>G (HSV- 1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>(HSV-1), 938T>C (HSV-2), 437_438 insA (HSV-1), 169delC (HSV-1), 170delC (HSV-1), 171delC (HSV-1), 172delC (HSV-1), 276delG (HSV-2), 278delG (HSV-2), 279delG (HSV-2), 280delG (HSV-2), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1); and (ii) a DNA pol mutation selected from 1879C>G (HSV-1), 1882C>G (HSV-2), 2405T>G (HSV-1), 2420T>G (HSV-2), 2500G>T (HSV-1), 2515G>T (HSV-2), 2515A>G (HSV-1), 2530A>G (HSV-2), 2892_2893 insT (HSV-1), 2893_2894 insT (HSV-1), 2894_2895 insT (HSV-1), 2895_2896 insT (HSV-1), 2907_2908 insT (HSV-2), 2908_2909 insT (HSV-2), 2909_2910 insT (HSV-2), and 2910_2911 insT (HSV-2);

c. determining the relative change in viral load of said HSV comprising said one or more mutation by comparing the viral load of HSV comprising said one or more mutation detected in step (b) with the viral load of a HSV comprising said one or more mutation in an isolated sample obtained from the subject at an earlier timepoint; and confirming the presence of efficacy when the viral load is decreased; and confirming the absence of efficacy when the viral load is increased (or unchanged).

In a preferable embodiment, said thymidine kinase (TK) mutation is selected from 250G>A (HSV-2), 100C>T (HSV-1), 268C>T (HSV-2), 373C>T (HSV-1), 146T>G (HSV-1), 363G>A (HSV-1), 497T>A (HSV-1), 558G>T (HSV-2), 641A>G (HSV-2), 715T>C (HSV-1), 938T>C (HSV-2), 437_438 insA (HSV-1), 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1). In a preferable embodiment, said DNA polymerase (DNA pol) mutation is selected from 1882C>G (HSV-2), 2405T>G (HSV-1), 2500G>T (HSV-1), 2515A>G (HSV-1), 2892_2893 insT (HSV-1), 2893_2894 insT (HSV-1), 2894_2895 insT (HSV-1), and 2895_2896 insT (HSV-1).

The term "earlier timepoint" may refer to a timepoint of at least 24 hours, at least 48 hours, at least 72 hours, at least 96 hours, at least 120 hours, at least 1 week, at least 2 weeks, at least 3 weeks, at least 4 weeks, at least 8 weeks, at least 12 weeks, at least 16 weeks, at least 20 weeks, at least 30 weeks, at least 40 weeks, at least 52 weeks, at least 2 years, at least 3 years, or at least 4 years earlier.

In one aspect, there is provided an antiviral drug for use in a method for treating an infection of an antiviral drug-resistant HSV (e.g. HSV-1 and/or HSV-2), wherein said method comprises:

a. confirming an antiviral drug-resistant HSV comprises a TK mutation selected from 100C>T (HSV-1), 268C>T (HSV-2), 373C>T (HSV-1), 376C>T (HSV-2), 146T>G (HSV-1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>C (HSV-1), 938T>C (HSV-2), 437_438 insA (HSV-1), 169delC (HSV-1), 170delC (HSV-1), 171delC (HSV-1), 172delC (HSV-1), 276delG (HSV-2), 278delG (HSV-2), 279delG (HSV-2), 280delG (HSV-2), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1); and b. administering to said subject a drug selected from foscarnet, cidofovir drug and docosanol.

In a preferable embodiment, said thymidine kinase (TK) mutation is selected from 250G>A (HSV-2), 100C>T (HSV-1), 268C>T (HSV-2), 373C>T (HSV-1), 146T>G (HSV-1), 363G>A (HSV-1), 497T>A (HSV-1), 558G>T (HSV-2), 641A>G (HSV-2), 715T>C (HSV-1), 938T>C (HSV-2), 437_438 insA (HSV-1), 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1).

Suitably, the antiviral drug is selected from foscarnet, cidofovir drug, docosanol, BAY 54-6322, ASP2151 and BAY 57-1293.

In one aspect, there is provided an antiviral drug for use in a method for treating an infection of an antiviral drug-resistant HSV (e.g. HSV-1 and/or HSV-2), wherein said method comprises:

a. confirming an antiviral drug-resistant HSV comprises a DNA Pol mutation selected from 1879C>G (HSV-1), 1882C>G (HSV-2), 2405T>G (HSV-1), 2420T>G (HSV-2), 2500G>T (HSV-1), 2515G>T (HSV-2), 2515A>G (HSV-1), 2530A>G (HSV-2), 2892_2893 insT (HSV-1), 2893_2894 insT (HSV-1), 2894_2895 insT (HSV-1), 2895_2896 insT (HSV-1), 2907_2908 insT (HSV-2), 2908_2909 insT (HSV-2), 2909_2910 insT (HSV-2), and 2910_2911 insT (HSV-2); and b. administering to said subject a drug selected from a docosanol drug, BAY 54-6322, ASP2151 and BAY 57-1293.

In a preferable embodiment, said DNA polymerase (DNA pol) mutation is selected from 1882C>G (HSV-2), 2405T>G (HSV-1), 2500G>T (HSV-1), 2515A>G (HSV-1), 2892_2893 insT (HSV-1), 2893_2894 insT (HSV-1), 2894_2895 insT (HSV-1), and 2895_2896 insT (HSV-1).

In one aspect, there is provided use of a TK mutation selected from 100C>T (HSV-1), 268C>T (HSV-2), 373C>T (HSV-1), 376C>T (HSV-2), 146T>G (HSV-1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>C (HSV-1), 938T>C (HSV-2), 437_438 insA (HSV-1), 169delC (HSV-1), 170delC (HSV-1), 171delC (HSV-1), 172delC (HSV-1), 276delG (HSV-2), 278delG (HSV-2), 279delG (HSV-2), 280delG (HSV-2), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1), or a combination thereof for:

a. detecting the presence or absence of an antiviral drug-resistant HSV in a sample;

b. diagnosing an infection with an antiviral drug-resistant HSV;

c. determining prognosis of an infection with an antiviral drug-resistant HSV;

d. identifying therapy suitable for treating an antiviral drug-resistant HSV; or e. monitoring efficacy of an HSV therapy.

In a preferable embodiment, said thymidine kinase (TK) mutation is selected from 250G>A (HSV-2), 100C>T (HSV-1), 268C>T (HSV-2), 373C>T (HSV-1), 146T>G (HSV-1), 363G>A (HSV-1), 497T>A (HSV-1), 558G>T (HSV-2), 641A>G (HSV-2), 715T>C (HSV-1), 938T>C (HSV-2), 437_438 insA (HSV-1), 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1).

In another aspect, there is provided use of a DNA pol mutation selected from 1879C>G (HSV-1), 1882C>G (HSV-2), 2405T>G (HSV-1), 2420T>G (HSV-2), 2500G>T (HSV-1), 2515G>T (HSV-2), 2515A>G (HSV-1), 2530A>G (HSV-2), 2892_2893 insT (HSV-1), 2893_2894 insT (HSV-1), 2894_2895 insT (HSV-1), 2895_2896 insT (HSV-1), 2907_2908 insT (HSV-2), 2908_2909 insT (HSV-2), 2909_2910 insT (HSV-2), and 2910_2911 insT (HSV-2), or a combination thereof for:

a. detecting the presence or absence of an antiviral drug-resistant HSV in a sample;
b. diagnosing an infection with an antiviral drug-resistant HSV;
c. determining prognosis of an infection with an antiviral drug-resistant HSV;
d. identifying therapy suitable for treating an antiviral drug-resistant HSV; or
e. monitoring efficacy of an HSV therapy.

In a preferable embodiment, said DNA polymerase (DNA pol) mutation is selected from 1882C>G (HSV-2), 2405T>G (HSV-1), 2500G>T (HSV-1), 2515A>G (HSV-1), 2892_2893 insT (HSV-1), 2893_2894 insT (HSV-1), 2894_2895 insT (HSV-1), and 2895_2896 insT (HSV-1).

In one aspect, there is provided use of an HSV mutation selected from a TK polymorphism mutation from 100C>T (HSV-1), 268C>T (HSV-2), 373C>T (HSV-1), 376C>T (HSV-2), 146T>G (HSV-1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>C (HSV-1), 938T>C (HSV-2), 437_438 insA (HSV-1), 169delC (HSV-1), 170delC (HSV-1), 171delC (HSV-1), 172delC (HSV-1), 276delG (HSV-2), 278delG (HSV-2), 279delG (HSV-2), 280delG (HSV-2), 458delC (HSV-2), 459delC (HSV-2), 460delC (HSV-2), 461delC (HSV-2), 881delC (HSV-1), 882delC (HSV-1), 883delC (HSV-1), 884delC (HSV-1); and a DNA pol mutation selected from 1879C>G (HSV-1), 1882C>G (HSV-2), 2405T>G (HSV-1), 2420T>G (HSV-2), 2500G>T (HSV-1), 2515G>T (HSV-2), 2515A>G (HSV-1), 2530A>G (HSV-2), 2892_2893 insT (HSV-1), 2893_2894 insT (HSV-1), 2894_2895 insT (HSV-1), 2895_2896 insT (HSV-1), 2907_2908 insT (HSV-2), 2908_2909 insT (HSV-2), 2909_2910 insT (HSV-2), and 2910_2911 insT (HSV-2), or a combination thereof for:

a. detecting the presence or absence of an antiviral drug-resistant HSV in a sample;
b. diagnosing an infection with an antiviral drug-resistant HSV;
c. determining prognosis of an infection with an antiviral drug-resistant HSV;
d. identifying therapy suitable for treating an antiviral drug-resistant HSV; or
e. monitoring efficacy of an HSV therapy.

In a preferable embodiment, said thymidine kinase (TK) mutation is selected from 250G>A (HSV-2), 100C>T (HSV-1), 268C>T (HSV-2), 373C>T (HSV-1), 146T>G (HSV-1), 363G>A (HSV-1), 497T>A (HSV-1), 558G>T (HSV-2), 641A>G (HSV-2), 715T>C (HSV-1), 938T>C (HSV-2), 437_438 insA (HSV-1), 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1). In a preferable embodiment, said DNA polymerase (DNA pol) mutation is selected from 1882C>G (HSV-2), 2405T>G (HSV-1), 2500G>T (HSV-1), 2515A>G (HSV-1), 2892_2893 insT (HSV-1), 2893_2894 insT (HSV-1), 2894_2895 insT (HSV-1), and 2895_2896 insT (HSV-1).

In one embodiment, a method or use of the present invention comprises the step of recording on a suitable data carrier, the data obtained in the step of detecting the presence or absence said one or more HSV mutation.

In one aspect, there is provided a data carrier comprising the data obtained in the step of identifying one or more HSV mutation according to a method of the invention. In another aspect, there is provided data carrier comprising the data obtained in the step of detecting the presence or absence of said one or more HSV mutation according to a method of the invention for use in a method for diagnosing an infection with an antiviral drug-resistant HSV.

In another aspect, there is provided a kit comprising reagents for detecting the presence or absence of (e.g. identifying) one or more HSV mutation selected from: (i) a TK mutation selected from 100C>T (HSV-1), 268C>T (HSV-2), 373C>T (HSV-1), 376C>T (HSV-2), 146T>G (HSV-1), 250G>A (HSV-2), 253A>C (HSV-1), 256A>C (HSV-2), 363G>A (HSV-1), 366G>A (HSV-2), 497T>A (HSV-1), 500T>A (HSV-2), 558G>T (HSV-2), 715T>C (HSV-1), 718T>C (HSV-2), 935T>C (HSV-1), 938T>C (HSV-2), 437_438 insA (HSV-1), 169delC (HSV-1), 170delC (HSV-1), 171delC (HSV-1), 172delC (HSV-1), 276delG (HSV-2), 278delG (HSV-2), 279delG (HSV-2), 280delG (HSV-2), 458delC (HSV-2), 459delC (HSV-2), 460delC (HSV-2), 461delC (HSV-2), 881delC (HSV-1), 882delC (HSV-1), 883delC (HSV-1), 884delC (HSV-1); and (ii) a DNA pol mutation selected from 1879C>G (HSV-1), 1882C>G (HSV-2), 2405T>G (HSV-1), 2420T>G (HSV-2), 2500G>T (HSV-1), 2515G>T (HSV-2), 2515A>G (HSV-1), 2530A>G (HSV-2), 2892_2893 insT (HSV-1), 2893_2894 insT (HSV-1), 2894_2895 insT (HSV-1), 2895_2896 insT (HSV-1), 2907_2908 insT (HSV-2), 2908_2909 insT (HSV-2), 2909_2910 insT (HSV-2), and 2910_2911 insT (HSV-2); and instructions for use of the same.

In a preferable embodiment, said thymidine kinase (TK) mutation is selected from 250G>A (HSV-2), 100C>T (HSV-1), 268C>T (HSV-2), 373C>T (HSV-1), 146T>G (HSV-1), 363G>A (HSV-1), 497T>A (HSV-1), 558G>T (HSV-2), 641A>G (HSV-2), 715T>C (HSV-1), 938T>C (HSV-2), 437_438 insA (HSV-1), 169delC (HSV-1), 170delC (HSV-1), 171delC (HSV-1), 172delC (HSV-1), 458delC (HSV-2), 459delC (HSV-2), 460delC (HSV-2), 461delC (HSV-2), 881delC (HSV-1), 882delC (HSV-1), 883delC (HSV-1), 884delC (HSV-1), and 885delC (HSV-1). In a preferable embodiment, said DNA polymerase (DNA pol) mutation is selected from 18820>G (HSV-2), 2405T>G (HSV-1), 2500G>T (HSV-1), 2515A>G (HSV-1), 2892_2893 insT (HSV-1), 2893_2894 insT (HSV-1), 2894_2895 insT (HSV-1), and 2895_2896insT (HSV-1).

In one embodiment, the reagents of said kit are for detecting the presence or absence of one or more HSV mutation by DNA sequencing, sequence capture, mass spectrometry, Western Blot, Enzyme activity assay and/or Enzyme-Linked Immunosorbent Assay (ELISA) (e.g. preferably by DNA sequencing) (e.g. preferably by mass spectrometry).

Polypeptide Polymorphisms

The present inventors have also identified the polypeptide polymorphisms caused by the mutations described herein.

All aspects, embodiments and definitions relating to mutations (e.g. nucleic acid sequence mutations) are also applicable to the corresponding aspects/embodiments, wherein the "mutation" is simply replaced by the corresponding "polymorphism" (e.g. polypeptide polymorphism). Corresponding polymorphisms of preferable mutations are shown in Tables 1-3.

TABLE 1

| HSV-1 TK gene | | | | | |
|---|---|---|---|---|---|
| Polymorphism | Mutation | Level of resistance (SR = strong resistance; W/IR = weak/intermediate resistance) | Polymorphism | Mutation | Level of resistance (SR = strong resistance; W/IR = weak/ intermediate resistance) |
| Q34* | 100C > T | W/IR to aciclovir, and/or W/IR to penciclovir | V204G | 611T > G | W/IR to aciclovir, SR to aciclovir and/or SR to penciclovir |
| L49R | 146T > G | W/IR to aciclovir, and/or SR to penciclovir | Y239H | 715T > C | W/IR to aciclovir, and/or SR to penciclovir |
| M121I | 363G > A | W/IR to aciclovir, and/or SR to penciclovir | 85* or H58fs | 169delC, 170delC, 171delC, and/or 172delC | W/IR to aciclovir, and/or SR to penciclovir |
| Q125* | 373C > T | W/IR to aciclovir, and/or SR to penciclovir | 183* (or E146fs or D228*) | 437_438insA | W/IR to aciclovir, and/or SR to penciclovir |
| I166N | 497T > A | W/IR to aciclovir, and/or SR to penciclovir | Frame-shift | 881delC, 882delC, 883delC, 884delC, and/or 885delC | W/IR to aciclovir, and/or SR to penciclovir |
| Y172S | 515A > C | W/IR to aciclovir, SR to aciclovir and/or SR to penciclovir | | | |

TABLE 2

| HSV-2 TK gene | | | | | |
|---|---|---|---|---|---|
| Polymorphism | Mutation | Level of resistance (SR = strong resistance; W/IR = weak/ intermediate resistance) | Polymorphism | Mutation | Level of resistance (SR = strong resistance; W/IR = weak/ intermediate resistance) |
| E84K | 250G > A | SR to aciclovir and/or SR to penciclovir | L313S | 938T > C | W/IR to aciclovir, and/or SR to penciclovir |
| M86L | 256A > C | SR to aciclovir and/or SR to penciclovir | L365P | 1094T > C | |
| Q90stop | 268C > T | SR to acyclovir and/or SR to penciclovir | 98stop, or A94fs | 276delG, 278delG 279delG, and/or 280delG | SR to acyclovir, and/or SR to penciclovir |

TABLE 2-continued

| HSV-2 TK gene | | | | | |
|---|---|---|---|---|---|
| Polymorphism | Mutation | Level of resistance (SR = strong resistance; W/IR = weak/ intermediate resistance) | Polymorphism | Mutation | Level of resistance (SR = strong resistance; W/IR = weak/ intermediate resistance) |
| Q186H | 558G > T | W/IR to aciclovir, and/or SR to penciclovir | 183stop, or P154fs | 458delC, 459delC, 460delC, and/or 461delC | W/IR to aciclovir, and/or SR to penciclovir |

TABLE 3

| HSV-1 pol gene | | | | | |
|---|---|---|---|---|---|
| Polymorphism | Mutation | Level of resistance (SR = strong resistance; W/IR = weak/ intermediate resistance) | Polymorphism | Mutation | Level of resistance (SR = strong resistance; W/IR = weak/ intermediate resistance) |
| L802R | 2405T > G | SR to acyclovir, SR to penciclovir and/or SR to foscarnet | 966*, or F965_I9 66insF | 2892_2893insT, 2893_2894insT, and/or 2894_2895insT, 2895_2896insT | SR to cidofovir |
| A834S | 2500G > T | SR to acyclovir, SR to penciclovir and/or SR to foscarnet | T839A | 2515G > T | SR to acyclovir, and/or SR to penciclovir |

An HSV-2 DNA pol mutation of 18820>G results in a R628G polymorphism. Suitably, an HSV-2 comprising said mutation/polymorphism has weak/intermediate resistance to acyclovir.

In one aspect there is provided a method for detecting the presence or absence of an antiviral drug-resistant HSV (e.g. in a subject), comprising:

a. identifying one or more HSV polymorphism selected from:
   i. a thymidine kinase (TK) polymorphism selected from Q34* (HSV-1), Q90* (HSV-2), Q125* (HSV-1), Q126* (HSV-2), L49R (HSV-1), E84K (HSV-2), M85L (HSV-1), M86L (HSV-2), M1211 (HSV-1), M1221 (HSV-2), 1166N (HSV-1), 1167N (HSV-2), Q186H (HSV-2), Y239H (HSV-1), Y240H (HSV-2), L312S (HSV-1), L313S (HSV-2), T183* (HSV-1), M85* (HSV-1), L98* (HSV-2), M183* (HSV-2), A294fs (HSV-1), P295fs (HSV-1), E296fs (HSV-1); and
   ii. a DNA polymerase (DNA pol) polymorphism selected from R627G (HSV-1), R628G (HSV-2), L802R (HSV-1), L807R (HSV-2), A834S (HSV-1), A839S (HSV-2), T839A (HSV-1), T844A (HSV-2), 1966* (HSV-1), and 1971* (HSV-2);

wherein the presence of said one or more HSV polymorphism confirms the presence of an antiviral drug-resistant HSV, and the absence of said one or more HSV polymorphism is indicative of the absence of an antiviral drug-resistant HSV.

Optionally, a description of a polymorphism may be preceded by the sign p. to denote identification of a polymorphism in a polypeptide. For example, a polymorphism L49R may be referred to as p.L49R.

In one aspect, there is provided a method for treating an infection of an antiviral drug-resistant HSV in a subject, comprising:

a. confirming an antiviral drug-resistant HSV comprises a TK polymorphism selected from Q34* (HSV-1), Q90* (HSV-2), Q125* (HSV-1), Q126* (HSV-2), L49R (HSV-1), E84K (HSV-2), M85L (HSV-1), M86L (HSV-2), M1211 (HSV-1), M1221 (HSV-2), 1166N (HSV-1), 1167N (HSV-2), Q186H (HSV-2), Y239H (HSV-1), Y240H (HSV-2), L312S (HSV-1), L313S (HSV-2), T183* (HSV-1), M85* (HSV-1), L98* (HSV-2), M183* (HSV-2), A294fs (HSV-1), P295fs (HSV-1), E296fs (HSV-1); and
b. administering to said subject a drug selected from foscarnet, cidofovir drug and docosanol.

In one embodiment, step b. comprises administering to said subject a drug selected from a foscarnet drug, cidofovir drug, a docosanol drug, BAY 54-6322, ASP2151 and BAY 57-1293.

In one aspect, there is provided a method for treating an infection of an antiviral drug-resistant HSV in a subject, comprising:

a. confirming an antiviral drug-resistant HSV comprises a DNA Pol polymorphism selected from R627G (HSV-1), R628G (HSV-2), L802R (HSV-1), L807R (HSV-2), A834S (HSV-1), A839S (HSV-2), T839A (HSV-1), T844A (HSV-2), 1966* (HSV-1), and 1971* (HSV-2); and b. administering to said subject a drug selected from a docosanol drug, BAY 54-6322, ASP2151 and BAY 57-1293.

In one aspect, there is provided an antiviral drug for use in a method for treating an infection of an antiviral drug-resistant HSV (e.g. HSV-1 and/or HSV-2), wherein said method comprises:

a. confirming an antiviral drug-resistant HSV comprises a TK polymorphism selected from Q34* (HSV-1), Q90* (HSV-2), Q125* (HSV-1), Q126* (HSV-2), L49R (HSV-1), E84K (HSV-2), M85L (HSV-1), M86L (HSV-2), M1211 (HSV-1), M1221 (HSV-2), 1166N (HSV-1), 1167N (HSV-2), Q186H (HSV-2), Y239H (HSV-1), Y240H (HSV-2), L312S (HSV-1), L313S (HSV-2), T183* (HSV-1), M85* (HSV-1), L98* (HSV-2), M183* (HSV-2), A294fs (HSV-1), P295fs (HSV-1), E296fs (HSV-1); and b. administering to said subject a drug selected from foscarnet, cidofovir drug and docosanol.

In one embodiment, step b. comprises administering to said subject a drug selected from a foscarnet drug, cidofovir drug, a docosanol drug, BAY 54-6322, ASP2151 and BAY 57-1293.

In one aspect, there is provided an antiviral drug for use in a method for treating an infection of an antiviral drug-resistant HSV (e.g. HSV-1 and/or HSV-2), wherein said method comprises:

a. confirming said an antiviral drug-resistant HSV comprises a DNA Pol polymorphism selected from R627G (HSV-1), R628G (HSV-2), L802R (HSV-1), L807R (HSV-2), A834S (HSV-1), A839S (HSV-2), T839A (HSV-1), T844A (HSV-2), 1966* (HSV-1), and 1971* (HSV-2); and b. administering to said subject a drug selected from a docosanol drug, BAY 54-6322, ASP2151 and BAY 57-1293.

In another aspect, there is provided a kit comprising reagents for detecting the presence or absence of one or more HSV mutation selected from: (i) a TK polymorphism selected from Q34* (HSV-1), Q90* (HSV-2), Q125* (HSV-1), Q126* (HSV-2), L49R (HSV-1), E84K (HSV-2), M85L (HSV-1), M86L (HSV-2), M1211 (HSV-1), M1221 (HSV-2), I166N (HSV-1), I167N (HSV-2), Q186H (HSV-2), Y239H (HSV-1), Y240H (HSV-2), L312S (HSV-1), L313S (HSV-2), T183* (HSV-1), M85* (HSV-1), L98* (HSV-2), M183* (HSV-2), A294fs (HSV-1), P295fs (HSV-1), E296fs (HSV-1); and (ii) a DNA polymerase (DNA pol) polymorphism selected from R627G (HSV-1), R628G (HSV-2), L802R (HSV-1), L807R (HSV-2), A834S (HSV-1), A839S (HSV-2), T839A (HSV-1), T844A (HSV-2), 1966* (HSV-1), and 1971* (HSV-2); and instructions for use of the same.

In a preferable embodiment, said TK polymorphism selected from E84K (HSV-2), Q34* (HSV-1), Q90* (HSV-2), Q125* (HSV-1), L49R (HSV-1), M1211 (HSV-1), 1166N (HSV-1), Q186H (HSV-2), H214R (HSV-2), E146fs (HSV-1), D228* (HSV-1), Y239H (HSV-1), L313S (HSV-2), T183* (HSV-1), H58fs (HSV-1), M85* (HSV-1), P154fs (HSV-2), M183* (HSV-2), A294fs (HSV-1), P295fs (HSV-1), and E296fs (HSV-1). In a preferable embodiment, R628G (HSV-2), L802R (HSV-1), A834S (HSV-1), T839A (HSV-1), F965_I966insF (HSV-1), and 1966* (HSV-1).

The methods of the present invention encompass identifying a mutation in the nucleic acid of a HSV and/or a polymorphism in the polypeptide sequence of a HSV. As such, a mutation or polymorphism may be described either by the nucleic acid mutation or the resulting amino acid polymorphism. For example, a "611T>G" single nucleotide polymorphism in the nucleic acid sequence of a HSV-1 TK results in the amino acid polymorphism (e.g. substitution) "V204G" in the polypeptide sequence of said HSV-1 TK. Thus, in one embodiment a nucleic acid mutation is identified. In another embodiment, a polypeptide polymorphism is identified.

The polypeptide polymorphisms resulting from the mutations described herein are outlined below. Thus, the mutation may be detected either directly within a nucleotide sequence or within a polypeptide sequence (e.g. by inferring the presence or absence of a mutation by detecting the presence of absence of the resulting polypeptide polymorphism). All references to "identifying one or more HSV mutation" herein may be substituted for "identifying one or more HSV polymorphism".

In one embodiment, the TK and/or DNA Pol polymorphism is a stop codon (e.g. early stop codon).

In one embodiment, a HSV-1 TK stop codon (e.g. early stop codon) polypeptide polymorphism is selected from Q34* (or Q34X), Q125* (or Q125X), M85* (or M85X), and T183* (or T183X). In one embodiment, a HSV-2 TK stop codon (e.g. early stop codon) polypeptide polymorphism is selected from Q126* (or Q126X), Q90* (or Q90X) and L98* (or L98X) (preferably Q126*).

In one embodiment, a HSV-1 DNA pol stop codon (e.g. early stop codon) polypeptide polymorphism is 1966* (or G966X).

In one embodiment, a HSV-1 TK stop codon (e.g. early stop codon) polypeptide polymorphism is selected from Q34* (or Q34X), Q125* (or Q125X), M85* (or M85X), and T183* (or T183X); a HSV-2 TK stop codon (e.g. early stop codon) polypeptide polymorphism is selected from Q126* (or Q126X), Q90* (or Q90X) and L98* (or L98X); and a HSV-1 DNA pol stop codon (e.g. early stop codon) polypeptide polymorphism is 1966* (or 1966X).

The skilled person understands that the asterix sign "*" (or, in alternative nomenclature, the "X" sign) denotes that the amino acid referred to is not expressed, as the codon encoding it is substituted with a stop codon (e.g. TAA, TAG, or TGA). For example, where the stop codon polymorphism is Q34* (or Q34X), this means that the glutamine ("Q") at position 34 of the TK polypeptide sequence is not translated, and that translation of the polypeptide ceases after amino acid 33. As such, the TK polypeptide is truncated.

In one embodiment, the TK and/or DNA Pol polymorphism is a (amino acid) substitution.

In one embodiment, a HSV-1 TK substitution polymorphism is selected from L49R, M85L, M1211, 1166N, Y239H, and L312S (preferably L49R, M1211, 1166N, and/or Y239H). In one embodiment, a HSV-2 TK substitution polymorphism is selected from E84K, M86L, M1221, 1167N, Q186H, Y240H, and L313S (preferably E84K, Q186H, and/or L313S).

In one embodiment, a HSV-1 DNA pol substitution polymorphism is selected from R627G, L802R, A834S, and T839A (preferably L802R, A834S, and/or T839A). In one embodiment, a HSV-2 DNA pol substitution polymorphism is selected from R628G, L807R, A839S, and T844A (preferably R628G).

In one embodiment, a HSV-1 TK substitution polymorphism is selected from L49R, M85L, M1211, 1166N, Y239H, and L312S (preferably L49R, M1211, 1166N, and/or Y239H); a HSV-2 TK substitution polymorphism is selected from E84K, M86L, M1221, 1167N, Q186H, Y240H, and L313S preferably E84K, Q186H, and/or L313S); a HSV-1 DNA pol substitution polymorphism is selected from R627G, L802R, A834S, and T839A (preferably L802R, A834S, and/or T839A); and a HSV-2 DNA pol substitution polymorphism is selected from R628G, L807R, A839S, and T844A (preferably R628G).

The skilled person understands the nomenclature used herein in the context of a substitution polymorphism. For example, where the substitution polymorphism is L49R, this means the lysine ("L") amino acid at position 49 of the TK polypeptide is substituted for arginine ("R").

In one embodiment, the TK and/or DNA Pol polymorphism is a frameshift.

In one embodiment, a HSV-1 TK frameshift polymorphism is selected from E146FS, H58fs, and E296fs. In one embodiment, a HSV-1 TK frameshift polymorphism is selected from A294fs, P295fs, and E296fs.

The sign "fs" denotes a frameshift (e.g. throughout the remainder of the polypeptide sequence) beginning at the amino acid referred to.

In a preferable embodiment, one or more (preferably all) of the polymorphisms described herein are not present in a reference (e.g. wild-type) HSV sequence.

Amino Acids

Amino acids relevant to the present invention are outlined below. The one letter code for said amino acids is presented in parentheses.

- Basic: arginine (R), lysine (K), histidine (H)
- Acidic: glutamic acid (E), aspartic acid (D)
- Polar: glutamine (Q), asparagine (B)
- Hydrophobic: leucine (L), isoleucine (I), valine (V)
- Aromatic: phenylalanine (F), tryptophan (W), tyrosine (Y)
- Small: glycine (G), alanine (A), serine (S), threonine (T), methionine (M)

Amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Sequence Identity

Any reference sequence described herein may differ from any other reference (e.g. wild-type) sequence due to natural sequence variation, yet be substantially homologous (e.g. have high sequence identity). The skilled person also understands how to employ appropriate sequence alignment to identify homologous/analogous nucleic acid/polypeptide positions amongst such sequences.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position—Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics:1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

Alignment Scores for Determining Sequence Identity

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |

-continued

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

The percent identity is then calculated as:

$$\frac{\text{Total number of identical matches}}{\text{[length of the longer sequence plus the number of gaps introducted into the longer sequence in order to align the two sequences]}} \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a mutation" includes a plurality of such polymorphisms and reference to "the mutation" includes reference to one or more polymorphisms and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

BRIEF DESCRIPTION OF THE DRAWINGS

Embodiments of the invention will now be described, by way of example only, with reference to the following Figures and Examples.

EXAMPLES

Materials & Methods

Subjects

Figure 1A:
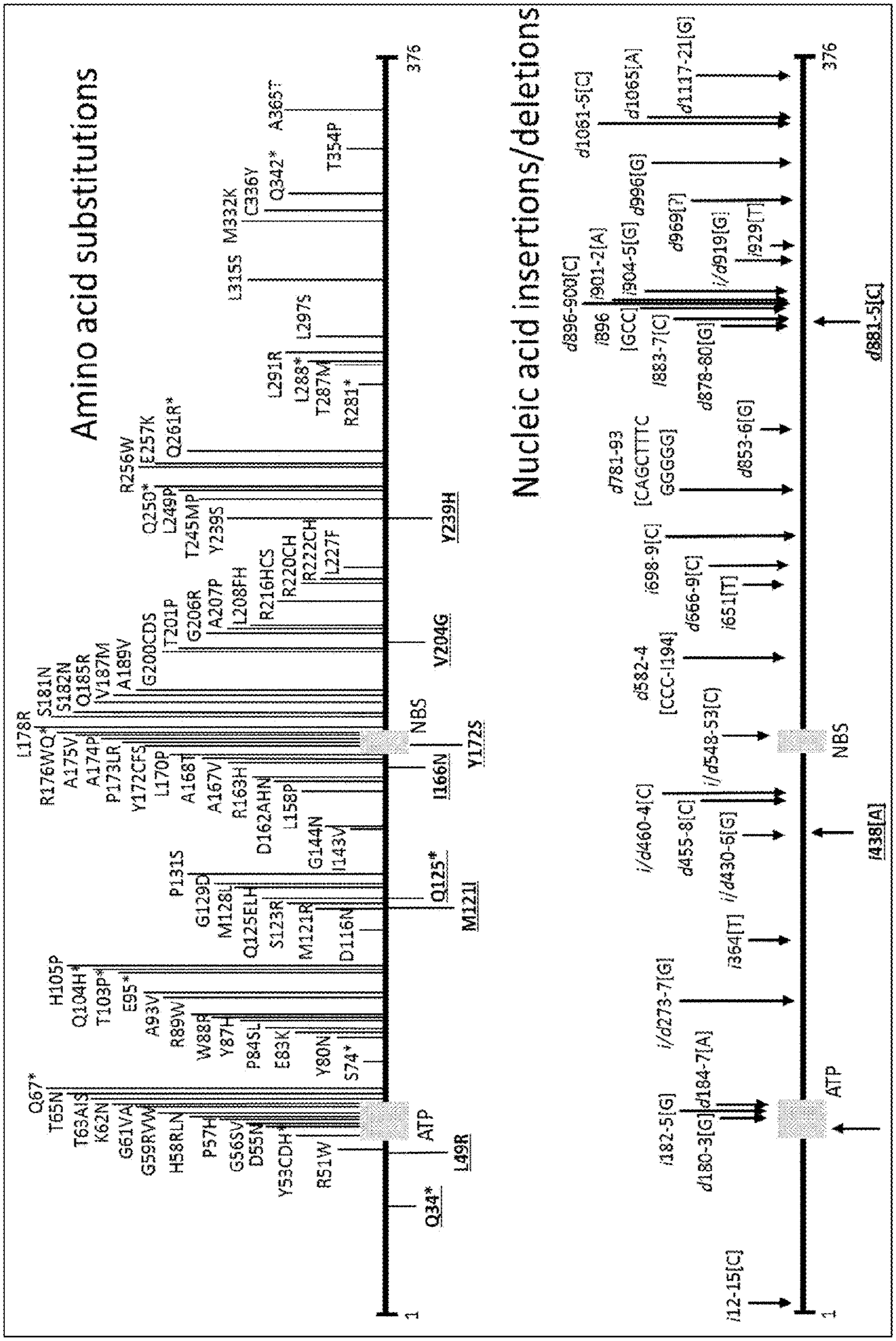
FIG. 1 (A-F) shows schemes demonstrating the TK and DNA pol mutations/polymorphism associated with antiviral drug resistance. Underlined font=resistance-associated mutations of the present invention/natural polymorphisms detected by the present inventors for the first time. *=stop codon; i=insertion; d=deletion. (A) HSV-1 TK resistance-associated mutations; (B) HSV-1 TK natural polymorphisms; (C) HSV-2 TK resistance-associated mutations; (D) HSV-2 TK polymorphisms; (E) HSV-1/HSV-2 DNA pol resistance-associated mutations; (F) HSV-1//HSV-2 DNA pol polymorphisms.
Figure 1B:
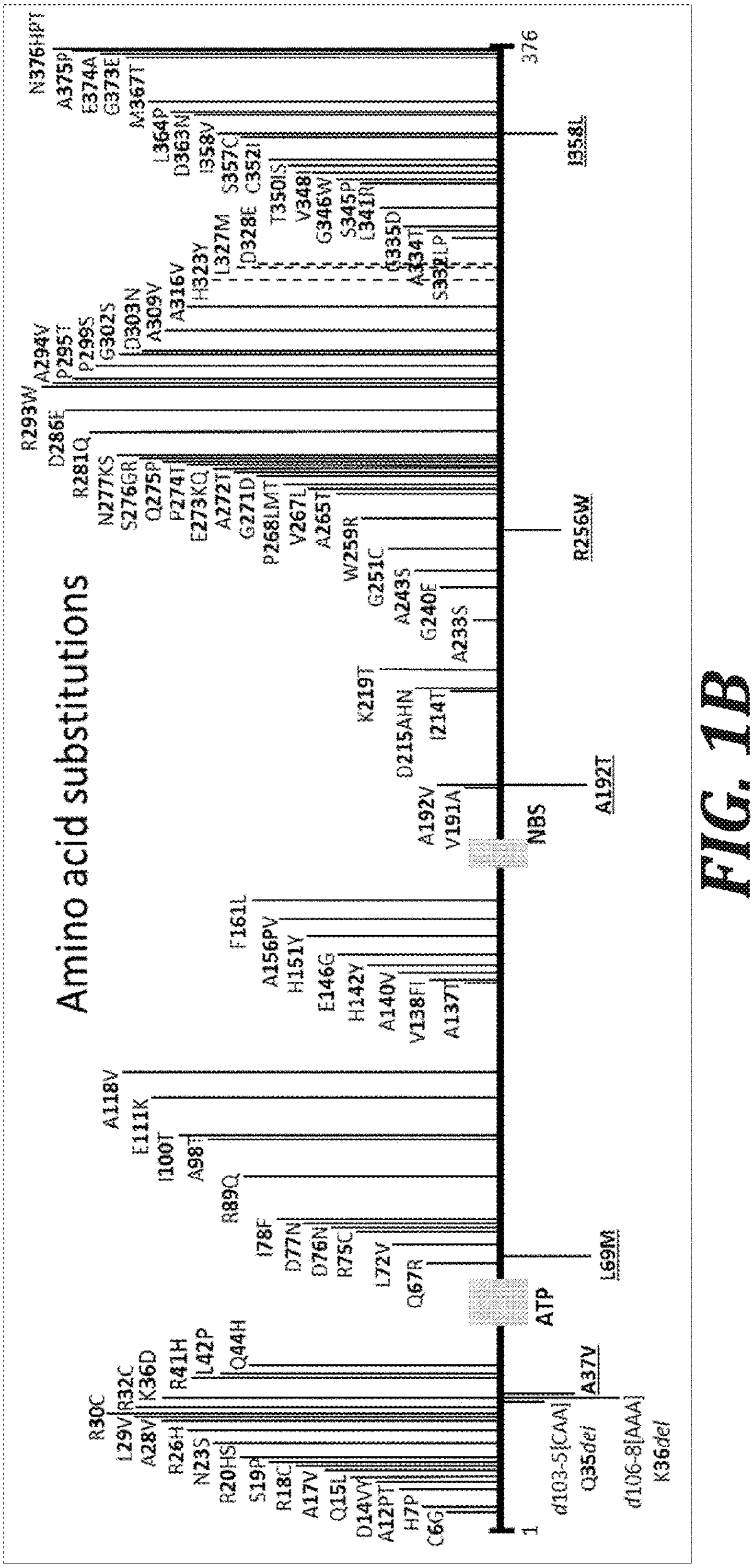
Figure 1C:
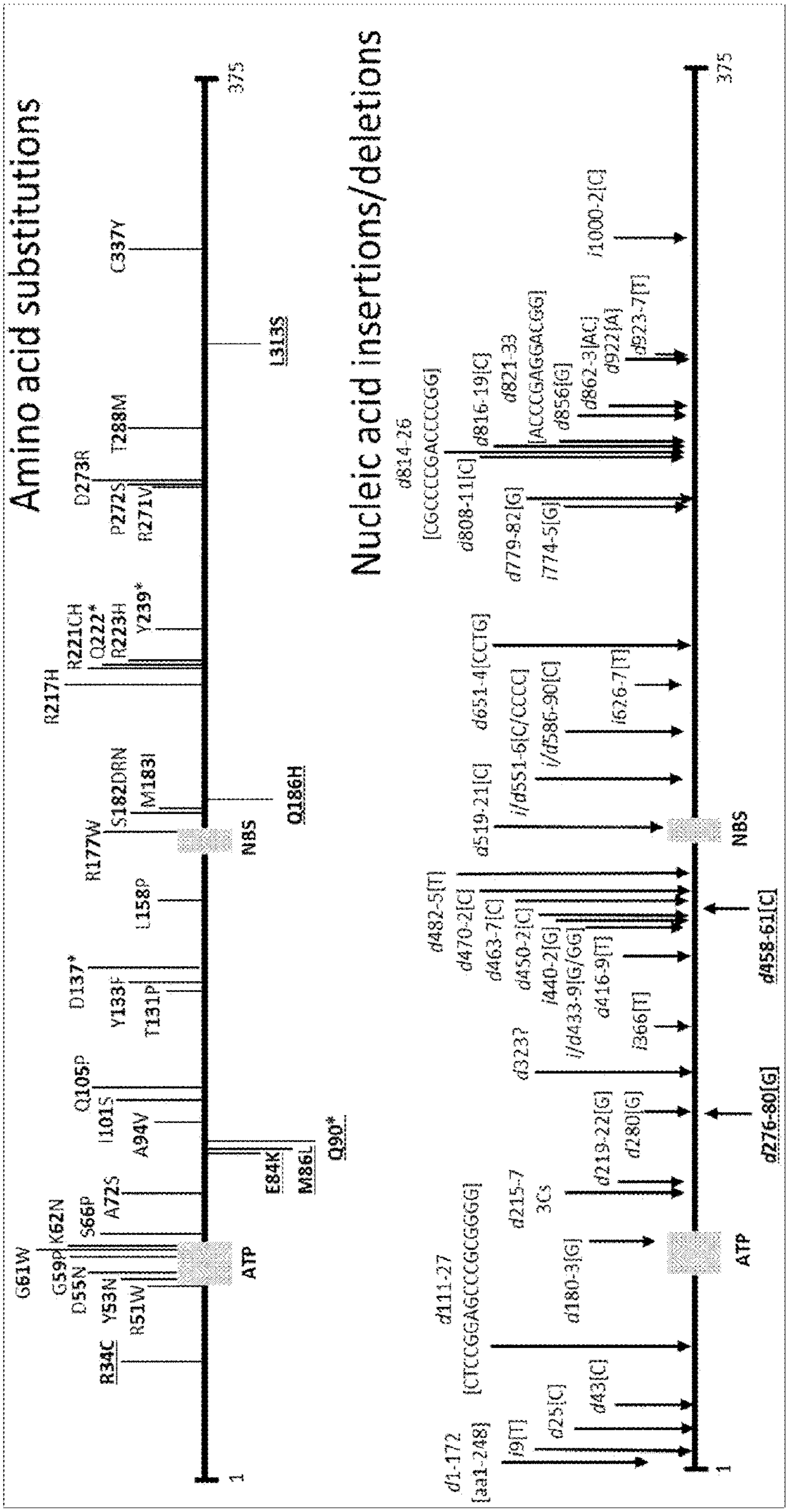
Figure 1D:
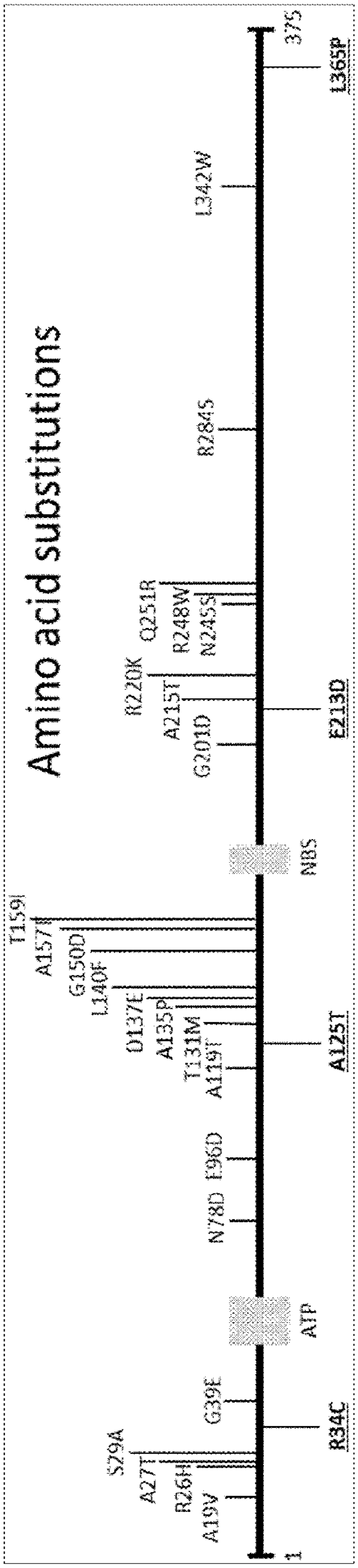
Figure 1E:
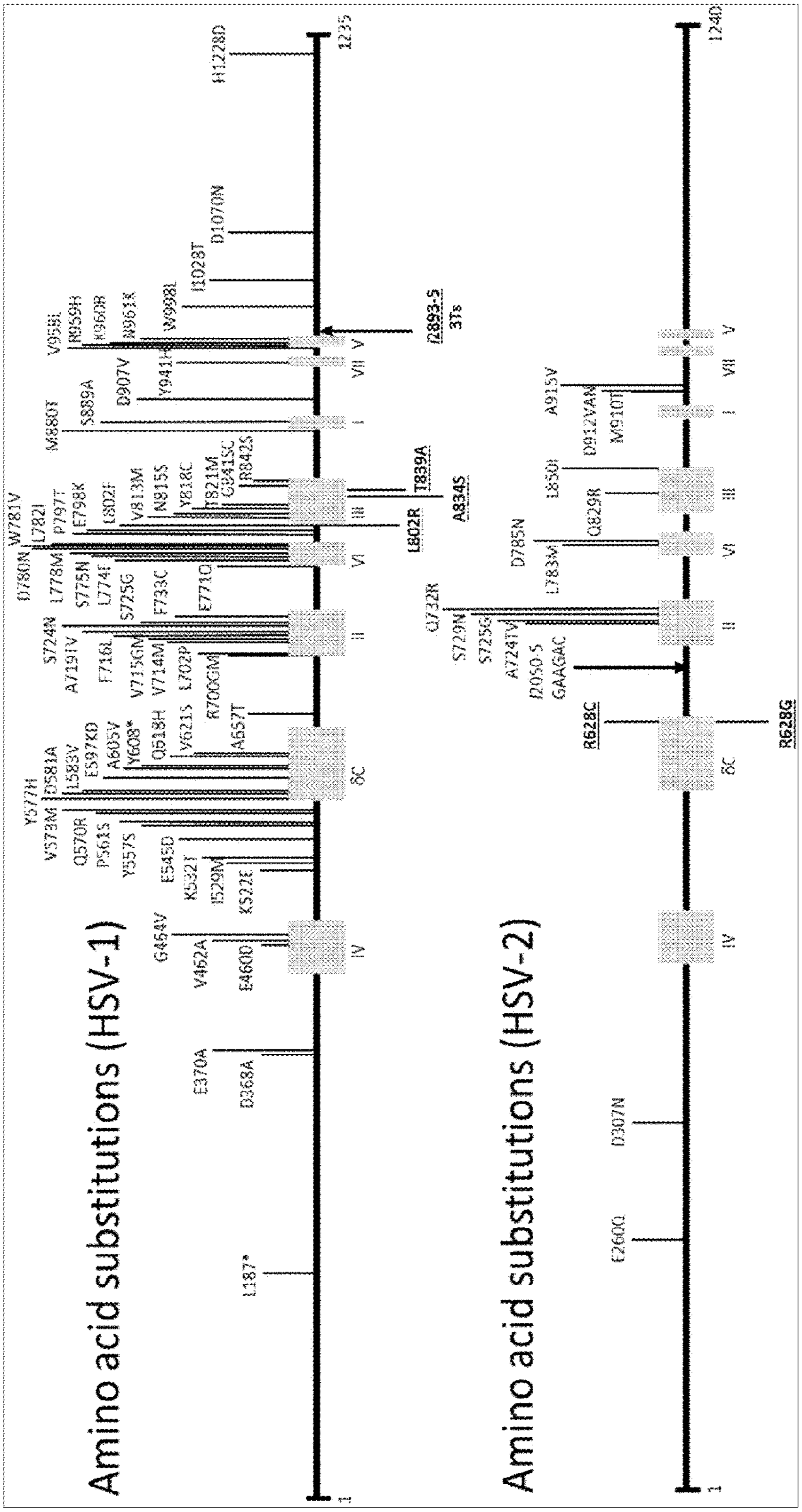
Figure 1F:
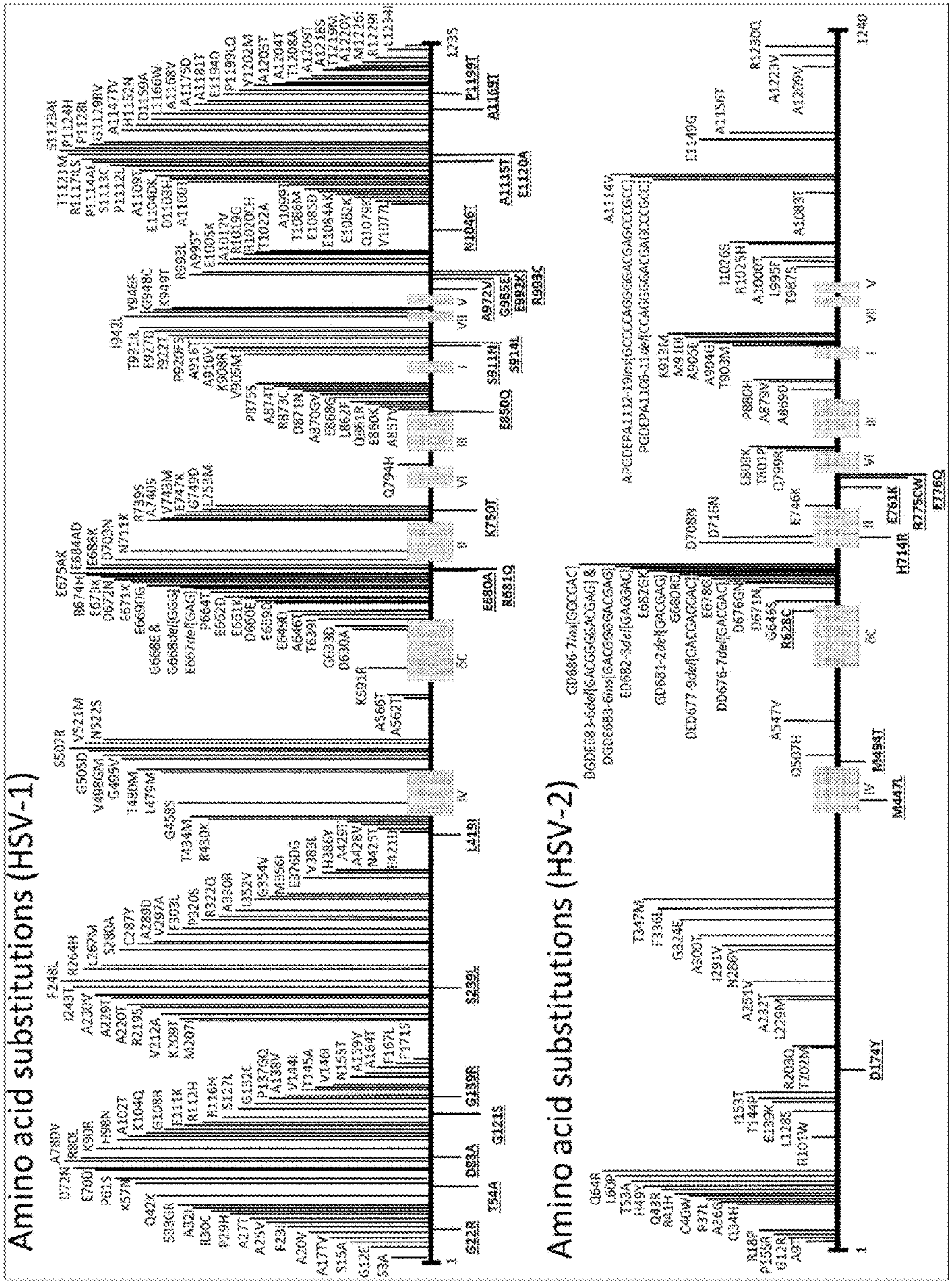

The samples tested and validated for resistance were obtained from Ireland, London, the midlands, north, south and east of England, Scotland and Wales. Thus, the results provided are representative of HSV strains present over widespread geographic regions. Samples were isolated from patients infected with a HSV and who did not respond (e.g. respond sufficiently) to treatment with one or more antiviral drugs (e.g. acyclovir, penciclovir, foscarnet, cidofovir).

Sample Preparation

The viruses were typically isolated from clinical swabs taken from patient lesions. The viruses were either cultured directly from the patient samples, or the virus or relevant segments thereof were amplified and cloned into recombinant vectors (e.g. using unique restriction sites or by homologous recombination). The recombinant vectors are then typically introduced into cells by transfection to produce recombinant and/or pseudotyped viruses.

Isolated viruses are typically titrated e.g. using monolayers of African green monkey kidney cells (Vero cells).

The samples were anonymized e.g. by removal of any patient identifiable information and assignment of a non-specific project number.

Detection of Mutation

Mutations were typically detected by DNA sequencing.

To prepare viral DNA for sequencing, confluent monolayers of cells (e.g. Vero cells) were infected at 5 PFUs/cell for 24 to 48 hours, until cytopathic effect became apparent. Viral supernatants were harvested by freeze-thawing and passed through a 0.45 μM filter. Four ml of the virus supernatant was incubated with 20 U/ml DNase (Promega) for 3 hours at 37° C. before loading onto a 1.5 ml 20% sucrose cushion and centrifuged at 100,000 g for 1 hour. Viral pellets were re-suspended in TE containing DNase chelator and extracted with the Pure-Link Viral RNA/DNA Mini Kit (Invitrogen) following manufacturer's instructions. Alternatively, viral DNA was extracted directly from a clinical sample using QIAamp DNA mini kit (Qiagen) or Pure-Link RNA/DNA mini kit (Invitrogen).

Regions of interest (e.g. the UL23 and/or UL30 genes) were then amplified by PCR. Primers which flank the UL23 and/or UL30 genes were typically used, although primers designed to amplify only a fragment of said gene in which a polymorphism may be expected to occur may also be suitable. The resulting amplicons were then sequenced using typical DNA sequencing technology available to the skilled person. The DNA sequences are then used to determine the corresponding polypeptide sequence.

The nucleotide and/or amino acid changes in the amplified sequence are detected by comparison with wild-type reference strains (or pretreatment sequences). Suitable wild-type reference strains include GenBank accession number JN555585.1 and JQ673480.1 as reference for HSV-1; and Z86099.2 and JN561323.2 as reference for HSV-2.

Plaque Reduction Assay

Viral sample were typically phenotypically characterised using the plaque reduction assay.

Viral isolates were used to infect a sub-confluent monolayer of Vero cells at a concentration of 75 or 50 plaque forming units (PFU) per well for HSV-1 and HSV-2, respectively. After 1 hour incubation at 37° C. cells were overlaid with CMC medium (4% Carboxymethyl cellulose in PBS) containing a serial dilution of the antiviral drugs acyclovir (ACV), pencyclovir (PCV), cidofovir (CDV) and foscarnet (FOS) or CMC alone, as a no drug control, and incubated for a further 72 hours until plaques became apparent. CMC medium typically used to create a semisolid interface and prevents indiscrimate viral spreading. Other materials (e.g. agar) may also be used to create this interface.

Cells were fixed with 10% formalin and stained with crystal violet before enumeration of the plaques (microscopic observation or use of fluorescent antibodies for detection is also suitable). The data obtained from these experiments were then expressed as percent inhibition of viral infectivity relative to the no drug control. The data was then used to determine $IC_{50}$ values for all four drugs using linear regression—i.e. dose-response curves were constructed from which the drug concentrations required to inhibit virus replication by 50% ($IC_{50}$) were determined.

Definitions of phenotypic drug susceptibility classification as sensitive or resistant were as follows: ACV, <3 μM or >40 μM; PCV, <10 μM or >40 μM; CDV, <24 μM or >30 μM; FOS, <250 μM or >400 μM; and ACV, <6.5 μM or >40 μM; PCV, <38 μM or >40 μM; FOS, <250 μM or >400 μM for HSV-1 and HSV-2, respectively. Any $IC_{50}$ values falling in between these sensitive and resistant cut-offs were reported as intermediate resistance.

The ratio of the $IC_{50}$ of patient-derived virus may also be divided by that of a wild-type reference virus (e.g. a virus known to be susceptible to the drug under investigation) to provide a fold change and determine the susceptibility of the patient-derived virus. A fold change greater than one means that the patient-derived virus is less susceptible to that particular drug compared with wild-type virus and vice versa.

A fold change greater than one does not necessarily mean that the patient will not respond to the treatment; therefore, $IC_{50}$ or fold change cutoff values have to be determined for each drug at which a patient-derived virus is considered to be susceptible or resistant. Different types of cutoff values can be used but the most pertinent is the 'clinical cutoff' which takes into consideration the relationship between $IC_{50}$ or fold change values and virological response or clinical outcome.

Example 1

Detecting Mutations

Viral samples were isolated from patients suspected of being infected with an antiviral-drug resistant HSV. The mutation (where relevant) resulting in resistance was detected by DNA sequencing as described above. Aligning the TK and/or DNA pol sequence of the antiviral-resistant virus with that of a wild-type reference sequence demonstrated the relevant mutation.

Example 2

Phenotypes of Detected TK and DNA Pol Mutations/Polymorphisms

The phenotype (i.e. reactivity to a drug) of the virus was characterised by the plaque reduction assay as described above. The present inventors have characterised the resistance-causing phenotype of a large number of TK and DNA pol mutations. Numerous natural polymorphisms (which do not cause drug resistance) have also been detected and characterised. The mutations, polymorphisms and associated phenotypes are demonstrated in Tables 4-7.

Definitions of phenotypic drug susceptibility classification: Acyclovir (ACV): <3 uM, 3-40 uM, >40 uM; Pencyclovir (PCV): <10 uM, 10-40 uM, >40 uM; Foscarnet (FOS): <250 uM, 250-400 uM, >400 uM; Cidofovir (CDV): <24 uM, 24-30 uM, >30 uM for HSV-1 and ACV: <6.5 μM, 6.5-40 μM, >40 μM; PCV: <38 μM, 38-40 μM, >40 μM; FOS: <250 μM, 250-400 μM, >400 μM for HSV-2, for sensitive, intermediate and resistant samples, respectively.

Table 4 presents 'natural' polymorphisms and resistance-associated substitutions and indels in HSV-1 TK gene and their effect on antiviral susceptibility. R=resistance (ACV and PCV $IC_{50}$>40 μM; FOS $IC_{50}$>400 μM; CDV $IC_{50}$>30 μM); IR=intermediate resistance (ACV $IC_{50}$>3 μM<40 μM; PCV $IC_{50}$>10 μM<40 μM; FOS $IC_{50}$>250<400 μM; CDV $IC_{50}$>24 μM<30 μM); S=susceptible (ACV $IC_{50}$<3 μM; PCV $IC_{50}$<10 μM; FOS $IC_{50}$<250 μM; CDV $IC_{50}$<24 μM); ND=not done; [a]mutation in non-conserved region in a sample which also contains Y239H in TK gene at a position associated with resistance; [b]sample also contains S914L and A1169AT mutations in non-conserved region of DNA pol gene; % ample also contains A1169AT mutations in non-conserved region of DNA pol gene; [d]sample also contains known resistance-associated mutation T287M in TK gene.

TABLE 4

| | Amino | | Drug susceptibility ($IC_{50}$ value) | | | |
|---|---|---|---|---|---|---|
| Study ID no. | acid change | Nucleotide change | Aciclovir (ACV) | Penciclovir (PCV) | Foscarnet (FOS) | Cidofovir (CDV) |
| HPG052 | Q34* | 100C >T | IR (8.45 μM) | IR (25 μM) | S (76.9 μM) | S (4.77 μM) |
| HPG050 | Q34* | 100C > T | R (>40 μM) | R (>160 μM) | S (169 μM) | ND |
| HPG005 | A37V | 110C > T | S (1.46 μM) | S (5.19 μM) | S (36.9 μM) | S (2.21 μM) |
| HPG045 | L49R | 146T > G | IR (31.5 μM) | R (>160 μM) | S (75 μM) | S (<1.56 μM) |
| HPG037 | L69M[a] | 205 > A | IR (24.8 μM) | R (>160 μM) | S (80 μM) | S (4.39 μM) |
| HPG013 | M121I | 363G > A | IR (18.77 μM) | R (105.29 μM) | S (77.98 μM) | S (3.11 μM) |
| HPG010 | Q125* | 373C > T | IR (9.21 μM) | R (87.14 μM) | S (46.66 μM) | S (<1.56 μM) |
| HPG011 | Q125* | 373C > T | IR (13.85 μM) | R (108.24 μM) | S (55.95 μM) | S (<1.56 μM) |
| HPG046 | I166N | 497T > A | IR (11.4 μM) | R (98.5 μM) | S (<50 μM) | S (2.1 μM) |
| HPG029 | Y172S | 515A > C | R (>40 μM) | R (>160 μM) | S (110.81 μM) | S (2.99 μM) |
| HPG003 | Y172S | 515A > C | IR (28 μM) | R (106 μM) | S (79 μM) | S (<1.56 μM) |
| HPG005 | A192T | 574G > A | S (1.46 μM) | S (5.19 μM) | S (<50 μM) | S (2.21 μM) |
| HPG008 | V204G | 611T > G | IR (22.5 μM) | R (>160 μM) | S (58.33 μM) | S (3.56 μM) |
| HPG027 | V204G[b] | 611T > G | R (>40 μM) | R (>160 μM) | S (216 μM) | S (3.93 μM) |
| HPG055 | V204G[c] | 611T > G | IR (5.1 μM) | S (9.34 μM) | S (<50 μM) | S (<1.56 μM) |
| HPG037 | Y239H | 715T > C | IR (24.8 μM) | R (>160 μM) | S (80 μM) | S (4.39 μM) |
| HPG037 | R256W | 766C > T | IR (24.8 μM) | R (>160 μM) | S (80 μM) | S (4.39 μM) |
| HPG033 | I358L[d] | 1072A > C | IR (38.9 μM) | R (>160 μM) | S (88.3 μM) | S (15 μM) |
| HPG039 | 85* or H58fs | 169delC, 170delC, 171delC, or 172delC | IR (25.6 μM) | R (158 μM) | S (59.8 μM) | S (2.97 μM) |
| HPG043 | 183* | 437_438insA (or E146fs or D228*) | IR (28.5 μM) | R (>160 μM) | S (69 μM) | S (1.65 μM) |
| HPG032 | 183* | 437_438insA (or E146fs or D228*) | IR (27.4 μM) | R (>160 μM) | S (100 μM) | S (3.61 μM) |
| HPG018 | frameshift | 881delC, 882delC, 883delC, 884delC, or 885delC | IR (24.7 μM) | R (117 μM) | S (66.7 μM) | S (3.03 μM) |
| HPG042 | frameshift | 881delC, 882delC, 883delC, 884delC, or 885delC | IR (>40 μM) | R (>160 μM) | S (60.7 μM) | S (<1.56 μM) |

Table 5 presents 'natural' polymorphisms and resistance-associated substitutions and indels in HSV-2 TK gene and their effect on antiviral susceptibility. R=resistance (ACV and PCV $IC_{50}$>40 μM; FOS $IC_{50}$>400 μM); IR=intermediate resistance (ACV $IC_{50}$>6.5 μM<40 μM; PCV $IC_{50}$>38 μM<40 μM; FOS $IC_{50}$>250<400 μM); S=susceptible (ACV $IC_{50}$<6.5 μM; PCV $IC_{50}$<38 μM; FOS $IC_{50}$<250 μM); ND=not done; [b]mutation in non-conserved region of TK gene but virus was not isolated and therefore phenotypic drug susceptibility testing could not be performed

TABLE 5

| Study ID no. | Amino acid change | Nucleotide change | Drug susceptibility ($IC_{50}$ value) Aciclovir (ACV) | Penciclovir (PCV) | Foscarnet (FOS) | Cidofovir (CDV) |
|---|---|---|---|---|---|---|
| HPG038 | R34C | 100C > T | S (2.04 μM) | S (9.64 μM) | S (73.7 μM) | ND |
| HPG036 | E84K | 250G > A | R (>40 μM) | R (>160 μM) | S (78.75 μM) | ND |
| HPG044 | M86L | 256A > C | R (>40 μM) | R (>160 μM) | S (73.8 μM) | ND |
| HPG048 | Q90stop | 268C > T | R (>40 μM) | R (>160 μM) | S (56.9 μM) | ND |
| HPG030 | Q90stop | 268C > T | R (>40 μM) | R (>160 μM) | S (92.3 μM) | ND |
| HPG001 | A125T | 373G > A | S (1.53 μM) | S (8.2 μM) | S (236 μM) | ND |
| HPG023 | Q186H | 558G > T | IR (12.08 μM) | S (31.07 μM) | S (77.98 μM) | ND |
| HPG017 | Q186H | 558G > T | IR (10.23 μM) | R (64.67 μM) | S (117.82 μM) | ND |
| HPG022 | E213D | 639A > C | S (4.46 μM) | S (26.86 μM) | S (82.05 μM) | ND |
| HPG024 | E213D | 639A > C | S (2.5 μM) | S (9.08 μM) | S (88.72 μM) | ND |
| HPG034 | L313S | 938A > C | IR (35.8 μM) | R (>160 μM) | S (73.5 μM) | ND |
| HPG049 | L365P[b] | 1094T > C | ND | ND | ND | ND |
| HPG057 | 98stop, or A94fs | 276delG, 278delG 279delG, or 280delG | R (>40 μM) | R (>160 μM) | S (98.5 μM) | ND |
| HPG028 | 98stop, or A94fs | 276delG, 278delG 279delG, or 280delG | R (>40 μM) | R (>160 μM) | S (98.8 μM) | ND |
| HPG058 | 183stop, or P154fs | 458delC, 459delC, 460delC, or 461delC | IR (36.2 μM) | R (>160 μM) | S (59 μM) | ND |

Table 6 presents 'natural' resistance-associated substitutions and indels in HSV-1 pol gene and their effect on antiviral susceptibility. R=resistance (ACV and PCV $IC_{50}$>40 μM; FOS $IC_{50}$>400 μM; CDV $IC_{50}$>30 μM); IR=intermediate resistance (ACV $IC_{50}$>3 μM<40 μM; PCV $IC_{50}$>10 μM<40 μM; FOS $IC_{50}$>250<400 μM; CDV $IC_{50}$>24 μM<30 μM); S=susceptible (ACV $IC_{50}$<3 μM; PCV $IC_{50}$<10 μM; FOS $IC_{50}$<250 μM; CDV $IC_{50}$<24 μM). Also contain A1169T mutation in non-conserved region; [a]mutation in non-conserved region in a sample which also contains the deletion (C) nt 881-885 in TK gene associated with resistance; [b]mutation in non-conserved region in a sample which also contains the mutation M1211 in TK gene; [c]mutation in non-conserved region in a sample which also contains the mutation R176stop in TK gene associated with resistance; [a]mutation in non-conserved region in a sample which also contains the mutation Q261stop in TK gene associated with resistance; [a]mutation in non-conserved region in a sample which also contains the deletion (G) nt 430-436 in TK gene associated with resistance; [f]mutation in non-conserved region in a sample which also contains the mutation S724N in DNA pol gene associated with resistance; [g]mutation in non-conserved region in a sample which also contains the mutation L49R in TK gene; [i]mutation in non-conserved region in a sample which also contains the deletion (C) nt 548-553 in TK gene associated with resistance; [j]mutation in non-conserved region in a sample which also contains deletion (G) nt 430-436 in TK gene associated with resistance; [k]mutation in non-conserved region in a sample which also contains deletion (G) nt 430-436 in TK gene associated with resistance; [l]mutations in conserved region (and for L802R on site associated with resistance) in a sample which also contains mutation R176W in TK gene associated with resistance; [m]mutation in conserved region in a sample which also contains deletion (G) nt 430-436 in TK gene associated with resistance; [n]mutation in non-conserved region in a sample which also contains mutation R216C in TK gene associated with resistance; [o]mutation in non-conserved region in a sample which also contains mutation deletion (C) nt 896-900 in TK gene associated with resistance; [p] mutation in non-conserved region in a sample which also contains mutation V204G in TK gene associated with resistance; [q]mutation in non-conserved region in a sample which also contains mutation A93V in TK gene associated with resistance; [r]mutation in non-conserved region in a sample which also contains mutation insert (G) nt 430-436 in TK gene associated with resistance; [s]mutation in non-conserved region in a sample which also contains mutation T287M in TK gene associated with resistance; [t]mutation in non-conserved region in a sample which also contains mutation deletion (C) nt 881-885 in TK gene, also Q substitution at this site is a known polymorphism

TABLE 6

| | Amino | | Drug susceptibility ($IC_{50}$ value) | | | |
|---|---|---|---|---|---|---|
| Study ID no. | acid change | Nucleotide change | Aciclovir (ACV) | Penciclovir (PCV) | Foscarnet (FOS) | Cidofovir (CDV) |
| HPG042‡ | G22R[a] | 64G > A | R (>40 μM) | R (>160 μM) | S (60.7 μM) | S (<1.56 μM) |
| HPG014 | T54A | 160A > G | S (1.41 μM) | S (5.66 μM) | S (140.54 μM) | S (17.24 μM) |
| HPG013‡ | D83A[b] | 248A > C | IR (18.77 μM) | R (105.29 μM) | S (77.98 μM) | S (3.11 μM) |
| HPG051 | D83A[c] | 248A > C | IR (29.2 μM) | R (>160 μM) | S (82.6 μM) | S (4.94 μM) |
| HPG006 | G121S[a] | 361G > A | R (>40 μM) | R (>160 μM) | S (115 μM) | S (6.14 μM) |
| HPG031 | G139R[e] | 415G > C or 415G > A | IR (27.65 μM) | R (155.68 μM) | S (108.47 μM) | S (4.8 μM) |
| HPG035 | S239L[f] | 716C > T | IR (5.43 μM) | IR (14.6 μM) | R (701 μM) | R (39.58 μM) |
| HPG045‡ | L419I[g] | 1255C > A | IR (31.5 μM) | R (>160 μM) | S (75 μM) | S (<1.56 μM) |
| HPG047‡ | E680[i] | 2039A > C | IR (22.43 μM) | R (>160 μM) | S (92.36 μM) | S (2.88 μM) |
| HPG021 | R681Q[j] | 2042G > A | R (>40 μM) | R (>160 μM) | S (156 μM) | S (<1.56 μM) |
| HPG019‡ | K750T[K] | 2249A > C | R (>40 μM) | R (>160 μM) | S (190 μM) | S (20.35 μM) |
| HPG053 | L802R + A834S[l] | 2405T > G 2500G > T | R (>40 μM) | R (>160 μM) | R (625.97 μM) | S (7.72 μM) |
| HPG021 | T839A[m] | 2515A > G | R (>40 μM) | R (>160 μM) | S (156 μM) | S (<1.56 μM) |
| HPG025 | E850Q[n] | 2548G > C | IR (22.2 μM) | R (118 μM) | S (99.1 μM) | S (<1.56 μM) |
| HPG026‡ | E850Q[n] | 2548G > C | IR (18.13 μM) | IR (35 μM) | S (68.3 μM) | S (<1.56 μM) |
| HPG020‡ | S911N | 2732G > A | S (0.56 μM) | S (2.48 μM) | S (99.3 μM) | S (4.38 μM) |
| HPG041‡ | S911N | 2732G > A | S (0.5 μM) | S (3 μM) | S (89.51 μM) | S (17.97 μM) |
| HPG040‡ | S911N[o] | 2732G > A | R (>40 μM) | R (>160 μM) | S (137 μM) | S (11.3 μM) |
| HPG053‡ | S911N[l] | 2732G > A | R (>40 μM) | R (>160 μM) | R (625.97 μM) | S (7.72 μM) |
| HPG027‡ | S914L[p] | 2741C > T | R (>40 μM) | R (>160 μM) | S (216 μM) | S (3.93 μM) |
| HPG042‡ | A972V[a] | 2915C > T | R (>40 μM) | R (>160 μM) | S (60.7 μM) | S (<1.56 μM) |
| HPG012 | G985E[q] | 2954G > A | R (>40 μM) | IR (9.67 μM) | S (92.13 μM) | S (2.84 μM) |
| HPG002‡ | E992K[r] | 2974G > A | IR (21.6 μM) | R (>160 μM) | S (<50 μM) | S (6.09 μM) |
| HPG009‡ | E992K | 2974G > A | S (1.3 μM) | S (4.05 μM) | S (77.47 μM) | S (9.44 μM) |
| HPG054‡ | E992K[r] | 2974G > A | IR (8.25 μM) | R (>160 μM) | S (52.9 μM) | S (3.85 μM) |
| HPG014 | R993C | 2977C > T | S (1.41 μM) | S (5.66 μM) | S (140.54 μM) | S (17.24 μM) |
| HPG015 | 966stop, or F965_1966insF | 2892_2893 insT, 2893_2894 insT, 2894_2895 insT, or 2895_2896 insT | S (2.4 μM) | S (8.48 μM) | S (162 μM) | R (45.08 μM) |
| HPG033‡ | N1046T[s] | 3137A > C | IR (38.9 μM) | R (>160 μM) | S (88.3 μM) | S (15 μM) |
| HPG014 | A1115T | 3343G > A | S (1.41 μM) | S (5.66 μM) | S (140.54 μM) | S (17.24 μM) |
| HPG031 | E1120A[e] | 3359A > C | IR (27.65 μM) | R (155.68 μM) | S (108.47 μM) | S (4.8 μM) |
| HPG016 | A1169T | 3505G > A | S (3.55 μM) | S (7.19 μM) | S (154.4 μM) | S (16.52 μM) |
| HPG018‡ | P1199T[t] | 3595C > A | IR (24.7 μM) | R (117 μM) | S (66.7 μM) | S (3.03 μM) |

Table 7 presents resistance-associated substitutions in HSV-2 pol gene and their effect on antiviral susceptibility. R=resistance (ACV and PCV $IC_{50}$>40 μM; FOS $IC_{50}$>400 μM); IR=intermediate resistance (ACV $IC_{50}$>6.5 μM<40 μM; PCV $IC_{50}$>38 μM<40 μM; FOS $IC_{50}$>250<400 μM); S=susceptible (ACV $IC_{50}$<6.5 μM; PCV $IC_{50}$<38 μM; FOS $IC_{50}$<250 μM); [a]mutation in non-conserved region in a sample which also contains mutation S729N in DNA pol associated with resistance; [b]mutation in non-conserved region in a sample which also contains mutation Q90stop in TK gene; [c]mutation in non-conserved region in a sample which also contains mutation deletion (G) nt 276-280 in TK gene.

TABLE 7

| | Amino | | Drug susceptibility ($IC_{50}$ value) | | | |
|---|---|---|---|---|---|---|
| Study ID no. | acid change | Nucleotide change | Aciclovir (ACV) | Penciclovir (PCV) | Foscarnet (FOS) | Cidofovir (CDV) |
| HPG022 | D174Y | 520G > T | S (4.46 μM) | S (26.86 μM) | S (82.05 μM) | ND |
| HPG056 | M447L | 1339A > C | S 1.56 μM) | S (8.61 μM) | S (88.05 μM) | ND |
| HPG004 | M494T[a] | 1481T > C | R (>40 μM) | R (>160 μM) | IR (348.71 μM) | ND |
| HPG007 | R628G | 1882C > G | IR (28.6 μM) | R (>160 μM) | R (783 μM) | ND |
| HPG001 | H714R | 2141A > G | S (1.53 μM) | S (8.2 μM) | S (236 μM) | ND |
| HPG048 | E761K[b] | 2281G > A | R (>40 μM) | R (>160 μM) | S (56.9 μM) | ND |
| HPG030 | E761K[b] | 2281G > A | R (>40 μM) | R (>160 μM) | S (92.3 μM) | ND |
| HPG028 | R775C[c]; R775W[c] | 2323C > T; 2325C > G | R (>40 μM) | R (>160 μM) | S (98.8 μM) | ND |
| HPG028 | E776Q[c] | 2326G > C | R (>40 μM) | R (>160 μM) | S (98.8 μM) | ND |

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

SEQUENCES (HSV-1 TK nucleic acid sequence)

SEQ ID NO: 1

ATGGCTTCGTACCCCTGCCATCAACACGCGTCTGCGTTCGACCAGGCTGCGCGTTCTC

GCGGCCATAACAACCGACGTACGGCGTTGCGCCCTCGCCGGCAGCAAAAAGCCACGG

AAGTCCGCCTGGAGCAGAAAATGCCCACGCTACTGCGGGTTTATATAGACGGTCCCCA

CGGGATGGGGAAAACCACCACCACGCAACTGCTGGTGGCCCTGGGTTCGCGCGACGA

TATCGTCTACGTACCCGAGCCGATGACTTACTGGCGGGTGTTGGGGGCTTCCGAGACA

ATCGCGAACATCTACACCACACAACACCGCCTCGACCAGGGTGAGATATCGGCCGGGG

ACGCGGCGGTGGTAATGACAAGCGCCCAGATAACAATGGGCATGCCTTATGCCGTGAC

CGACGCCGTTCTGGCTCCTCATATCGGGGGGGAGGCTGGGAGCTCACATGCCCCGCC

CCCGGCCCTCACCCTCATCTTCGACCGCCATCCCATCGCCGCCCTCCTGTGCTACCCG

GCCGCGCGATACCTTATGGGCAGCATGACCCCCCAGGCCGTGCTGGCGTTCGTGGCC

CTCATCCCGCCGACCTTGCCCGGCACAAACATCGTGTTGGGGGCCCTTCCGGAGGACA

GACACATCGACCGCCTGGCCAAACGCCAGCGCCCCGGCGAGCGGCTTGACCTGGCTA

TGCTGGCCGCGATTCGCCGCGTTTATGGGCTGCTTGCCAATACGGTGCGGTATCTGCA

GGGCGGCGGGTCGTGGCGGGAGGATTGGGGACAGCTTTCGGGGGCGGCCGTGCCGC

CCCAGGGTGCCGAGCCCCAGAGCAACGCGGGCCCACGACCCCATATCGGGGACACGT

TATTTACCCTGTTTCGGGCCCCCGAGTTGCTGGCCCCCAACGGCGACCTGTATAACGT

GTTTGCCTGGGCTTTGGACGTCTTGGCCAAACGCCTCCGTCCCATGCACGTCTTTATCC

TGGATTACGACCAATCGCCCGCCGGCTGCCGGGACGCCCTGCTGCAACTTACCTCCGG

GATGGTCCAGACCCACGTCACCACCCCAGGCTCCATACCGACGATCTGCGACCTGGCG

CGCACGTTTGCCCGGGAGATGGGGGAGGCTAACTGA (HSV-1 TK polypeptide sequence)

SEQ ID NO: 2

MASYPCHQHASAFDQAARSRGHNNRRTALRPRRQQKATEVRLEQKMPTLLRVYIDGPHG

MGKTTTTQLLVALGSRDDIVYVPEPMTYWRVLGASETIANIYTTQHRLDQGEISAGDAAVVM

TSAQITMGMPYAVTDAVLAPHIGGEAGSSHAPPPALTLIFDRHPIAALLCYPAARYLMGSMT

PQAVLAFVALIPPTLPGTNIVLGALPEDRHIDRLAKRQRPGERLDLAMLAAIRRVYGLLANTV

RYLQGGGSWREDWGQLSGAAVPPQGAEPQSNAGPRPHIGDTLFTLFRAPELLAPNGDLYN

VFAWALDVLAKRLRPMHVFILDYDQSPAGCRDALLQLTSGMVQTHVTTPGSIPTICDLARTF

AREMGEAN (HSV-1 DNA pol nucleic acid sequence)

SEQ ID NO: 3

ATGTTTTCCGGTGGCGGCGGCCCGCTGTCCCCCGGAGGAAAGTCGGCGGCCAGGGCG

GCGTCCGGGTTTTTTGCGCCCGCCGGCCCTCGCGGAGCCAGCCGGGGACCCCCGCCT

TGTTTGAGGCAAAACTTTTACAACCCCTACCTCGCCCCAGTCGGGACGCAACAGAAGCC

GACCGGGCCAACCCAGCGCCATACGTACTATAGCGAATGCGATGAATTTCGATTCATCG

CCCCGCGGGTGCTGGACGAGGATGCCCCCCCGGAGAAGCGCGCCGGGGTGCACGAC

GGTCACCTCAAGCGCGCCCCCAAGGTGTACTGCGGGGGGGACGAGCGCGACGTCCTC

-continued

CGCGTCGGGTCGGGCGGCTTCTGGCCGCGGCGCTCGCGCCTGTGGGGCGGCGTGGA

CCACGCCCCGGCGGGGTTCAACCCCACCGTCACCGTCTTTCACGTGTACGACATCCTG

GAGAACGTGGAGCACGCGTACGGCATGCGCGCGGCCCAGTTCCACGCGCGGTTTATG

GACGCCATCACACCGACGGGGACCGTCATCACGCTCCTGGGCCTGACTCCGGAAGGC

CACCGGGTGGCCGTTCACGTTTACGGCACGCGGCAGTACTTTTACATGAACAAGGAGG

AGGTCGACAGGCACCTACAATGCCGCGCCCCACGAGATCTCTGCGAGCGCATGGCCG

CGGCCCTGCGCGAGTCCCCGGGCGCGTCGTTCCGCGGCATCTCCGCGGACCACTTCG

AGGCGGAGGTGGTGGAGCGCACCGACGTGTACTACTACGAGACGCGCCCCGCTCTGT

TTTACCGCGTCTACGTCCGAAGCGGGCGCGTGCTGTCGTACCTGTGCGACAACTTCTG

CCCGGCCATCAAGAAGTACGAGGGTGGGGTCGACGCCACCACCCGGTTCATCCTGGA

CAACCCCGGGTTCGTCACCTTCGGCTGGTACCGTCTCAAACCGGGCCGGAACAACACG

CTAGCCCAGCCGCGGGCCCCGATGGCCTTCGGGACATCCAGCGACGTCGAGTTTAACT

GTACGGCGGACAACCTGGCCATCGAGGGGGGCATGAGCGACCTACCGGCATACAAGC

TCATGTGCTTCGATATCGAATGCAAGGCGGGGGGGGAGGACGAGCTGGCCTTTCCGGT

GGCCGGGCACCCGGAGGACCTGGTCATCCAGATATCCTGTCTGCTCTACGACCTGTCC

ACCACCGCCCTGGAGCACGTCCTCCTGTTTTCGCTCGGTTCCTGCGACCTCCCCGAAT

CCCACCTGAACGAGCTGGCGGCCAGGGGCCTGCCCACGCCCGTGGTTCTGGAATTCG

ACAGCGAATTCGAGATGCTGTTGGCCTTCATGACCCTTGTGAAACAGTACGGCCCCGA

GTTCGTGACCGGGTACAACATCATCAACTTCGACTGGCCCTTCTTGCTGGCCAAGCTGA

CGGACATTTACAAGGTCCCCCTGGACGGGTACGGCCGCATGAACGGCCGGGGCGTGT

TTCGCGTGTGGGACATAGGCCAGAGCCACTTCCAGAAGCGCAGCAAGATAAAGGTGAA

CGGCATGGTGAACATCGACATGTACGGGATTATAACCGACAAGATCAAGCTCTCGAGCT

ACAAGCTCAACGCCGTGGCCGAAGCCGTCCTGAAGGACAAGAAGAAGGACCTGAGCTA

TCGCGACATCCCCGCCTACTACGCCGCCGGGCCCGCGCAACGCGGGGTGATCGGCGA

GTACTGCATACAGGATTCCCTGCTGGTGGGCCAGCTGTTTTTTAAGTTTTTGCCCCATCT

GGAGCTCTCGGCCGTCGCGCGCTTGGCGGGTATTAACATCACCCGCACCATCTACGAC

GGCCAGCAGATCCGCGTCTTTACGTGCCTGCTGCGCCTGGCCGACCAGAAGGGCTTTA

TTCTGCCGGACACCCAGGGGCGATTTAGGGGCGCCGGGGGGGAGGCGCCCAAGCGT

CCGGCCGCAGCCCGGGAGGACGAGGAGCGGCCAGAGGAGGAGGGGGAGGACGAGG

ACGAACGCGAGGAGGGGGGGGGCGAGCGGGAGCCGGAGGGCGCGCGGGAGACCGC

CGGCAGGCACGTGGGGTACCAGGGGGCCAGGGTCCTTGACCCCACTTCCGGGTTTCA

CGTGAACCCCGTGGTGGTGTTCGACTTTGCCAGCCTGTACCCCAGCATCATCCAGGCC

CACAACCTGTGCTTCAGCACGCTCTCCCTGAGGGCCGACGCAGTGGCGCACCTGGAG

GCGGGCAAGGACTACCTGGAGATCGAGGTGGGGGGGCGACGGCTGTTCTTCGTCAAG

GCTCACGTGCGAGAGAGCCTCCTCAGCATCCTCCTGCGGGACTGGCTCGCCATGCGAA

AGCAGATCCGCTCGCGGATTCCCCAGAGCAGCCCCGAGGAGGCCGTGCTCCTGGACA

AGCAGCAGGCCGCCATCAAGGTCGTGTGTAACTCGGTGTACGGGTTCACGGGAGTGCA

GCACGGACTCCTGCCGTGCCTGCACGTTGCCGCGACGGTGACGACCATCGGCCGCGA

GATGCTGCTCGCGACCCGCGAGTACGTCCACGCGCGCTGGGCGGCCTTCGAACAGCT

CCTGGCCGATTTCCCGGAGGCGGCCGACATGCGCGCCCCCGGGCCCTATTCCATGCG

-continued

CATCATCTACGGGGACACGGACTCCATCTTTGTGCTGTGCCGCGGCCTCACGGCCGCC

GGGCTGACGGCCGTGGGCGACAAGATGGCGAGCCACATCTCGCGCGCGCTGTTTCTG

CCCCCCATCAAACTCGAGTGCGAAAAGACGTTCACCAAGCTGCTGCTGATCGCCAAGA

AAAAGTACATCGGCGTCATCTACGGGGGTAAGATGCTCATCAAGGGCGTGGATCTGGT

GCGCAAAAACAACTGCGCGTTTATCAACCGCACCTCCAGGGCCCTGGTCGACCTGCTG

TTTTACGACGATACCGTCTCCGGAGCGGCCGCCGCGTTAGCCGAGCGCCCCGCGGAG

GAGTGGCTGGCGCGACCCCTGCCCGAGGGACTGCAGGCGTTCGGGGCCGTCCTCGTA

GACGCCCATCGGCGCATCACCGACCCGGAGAGGGACATCCAGGACTTTGTCCTCACCG

CCGAACTGAGCAGACACCCGCGCGCGTACACCAACAAGCGCCTGGCCCACCTGACGG

TGTATTACAAGCTCATGGCCCGCCGCGCGCAGGTCCCGTCCATCAAGGACCGGATCCC

GTACGTGATCGTGGCCCAGACCCGCGAGGTAGAGGAGACGGTCGCGCGGCTGGCCGC

CCTCCGCGAGCTAGACGCCGCCGCCCCAGGGGACGAGCCCGCCCCCCCCGCGGCCC

TGCCCTCCCCGGCCAAGCGCCCCCGGGAGACGCCGTCGCCTGCCGACCCCCCGGGA

GGCGCGTCCAAGCCCCGCAAGCTGCTGGTGTCCGAGCTGGCCGAGGATCCCGCATAC

GCCATTGCCCACGGCGTCGCCCTGAACACGGACTATTACTTCTCCCACCTGTTGGGGG

CGGCGTGCGTGACATTCAAGGCCCTGTTTGGGAATAACGCCAAGATCACCGAGAGTCT

GTTAAAAAGGTTTATTCCCGAAGTGTGGCACCCCCCGGACGACGTGGCCGCGCGGCTC

CGGACCGCAGGGTTCGGGGCGGTGGGTGCCGGCGCTACGGCGGAGGAAACTCGTCG

AATGTTGCATAGAGCCTTTGATACTCTAGCATGAGCCCCCCGTCGAAGCTGATGTCCCT

CATTTTACAATAAA (HSV-1 DNA pol polypeptide sequence)

SEQ ID NO: 4

MFSGGGGPLSPGGKSAARAASGFFAPAGPRGASRGPPPCLRQNFYNPYLAPVGTQQKPT

GPTQRHTYYSECDEFRFIAPRVLDEDAPPEKRAGVHDGHLKRAPKVYCGGDERDVLRVGS

GGFWPRRSRLWGGVDHAPAGFNPTVTVFHVYDILENVEHAYGMRAAQFHARFMDAITPTG

TVITLLGLTPEGHRVAVHVYGTRQYFYMNKEEVDRHLQCRAPRDLCERMAAALRESPGASF

RGISADHFEAEVVERTDVYYYETRPALFYRVYVRSGRVLSYLCDNFCPAIKKYEGGVDATTR

FILDNPGFVTFGWYRLKPGRNNTLAQPRAPMAFGTSSDVEFNCTADNLAIEGGMSDLPAYK

LMCFDIECKAGGEDELAFPVAGHPEDLVIQISCLLYDLSTTALEHVLLFSLGSCDLPESHLNE

LAARGLPTPVVLEFDSEFEMLLAFMTLVKQYGPEFVTGYNIINFDWPFLLAKLTDIYKVPLDG

YGRMNGRGVFRVWDIGQSHFQKRSKIKVNGMVNIDMYGIITDKIKLSSYKLNAVAEAVLKDK

KKDLSYRDIPAYYAAGPAQRGVIGEYCIQDSLLVGQLFFKFLPHLELSAVARLAGINITRTIYD

GQQIRVFTCLLRLADQKGFILPDTQGRFRGAGGEAPKRPAAAREDEERPEEEGEDEDEREE

GGGEREPEGARETAGRHVGYQGARVLDPTSGFHVNPVVVFDFASLYPSIIQAHNLCFSTLS

LRADAVAHLEAGKDYLEIEVGGRRLFFVKAHVRESLLSILLRDWLAMRKQIRSRIPQSSPEEA

VLLDKQQAAIKVVCNSVYGFTGVQHGLLPCLHVAATVTTIGREMLLATREYVHARWAAFEQL

LADFPEAADMRAPGPYSMRIIYGDTDSIFVLCRGLTAAGLTAVGDKMASHISRALFLPPIKLE

CEKTFTKLLLIAKKKYIGVIYGGKMLIKGVDLVRKNNCAFINRTSRALVDLLFYDDTVSGAAAA

LAERPAEEWLARPLPEGLQAFGAVLVDAHRRITDPERDIQDFVLTAELSRHPRAYTNKRLAH

LTVYYKLMARRAQVPSIKDRIPYVIVAQTREVEETVARLAALRELDAAAPGDEPAPPAALPSP

AKRPRETPSPADPPGGASKPRKLLVSELAEDPAYAIAHGVALNTDYYFSHLLGAACVTFKAL

FGNNAKITESLLKRFIPEVWHPPDDVAARLRTAGFGAVGAGATAEETRRMLHRAFDTLA

-continued (HSV-2 TK nucleic acid sequence)

SEQ ID NO: 5

ATGGCTTCTCACGCCGGCCAACAGCACGCGCCTGCGTTCGGTCAGGCTGCTCGTGCGA

GCGGGCCTACCGACGGCCGCGCGGCGTCCCGTCCTAGCCATCGCCAGGGGGCCTCC

GGAGCCCGCGGGGATCCGGAGCTGCCCACGCTGCTGCGGGTTTATATAGACGGACCC

CACGGGGTGGGGAAGACCACCACCTCCGCGCAGCTGATGGAGGCCCTGGGGCCGCG

CGACAATATCGTCTACGTCCCCGAGCCGATGACTTACTGGCAGGTGCTGGGGGCCTCC

GAGACCCTGACGAACATCTACAACACGCAGCACCGTCTGGACCGCGGCGAGATATCGG

CCGGGGAGGCGGCGGTGGTAATGACCAGCGCCCAGATAACAATGAGCACGCCTTATG

CGGCGACGGACGCCGTTTTGGCTCCTCATATCGGGGGGGAGGCTGTGGGCCCGCAAG

CCCCGCCCCCGGCCCTCACCCTTGTTTTCGACCGGCACCCTATCGCCTCCCTGCTGTG

CTACCCGGCCGCGCGGTACCTCATGGGAAGCATGACCCCCCAGGCCGTGTTGGCGTT

CGTGGCCCTCATGCCCCCGACCGCGCCCGGCACGAACCTGGTCCTGGGTGTCCTTCC

GGAGGCCGAACACGCCGACCGCCTGGCCAGACGCCAACGCCCGGGCGAGCGGCTTG

ACCTGGCCATGCTGTCCGCCATTCGCCGTGTCTACGATCTACTCGCCAACACGGTGCG

GTACCTGCAGCGCGGCGGGAGGTGGCGGGAGGACTGGGGCCGGCTGACGGGGGTCG

CCGCGGCGACCCCGCGCCCCGACCCCGAGGACGGCGCGGGGTCTCTGCCCCGCATC

GAGGACACGCTGTTTGCCCTGTTCCGCGTTCCCGAGCTGCTGGCCCCCAACGGGGACT

TGTACCACATTTTTGCCTGGGTCTTGGACGTCTTGGCCGACCGCCTCCTTCCGATGCAT

CTATTTGTCCTGGATTACGATCAGTCGCCCGTCGGGTGTCGAGACGCCCTGTTGCGCC

TCACCGCCGGGATGATCCCAACCCGCGTCACAACCGCCGGGTCCATCGCCGAGATAC

GCGACCTGGCGCGCACGTTTGCCCGCGAGGTGGGGGGAGTTTAG (HSV-2 TK polypeptide sequence)

SEQ ID NO: 6

MASHAGQQHAPAFGQAARASGPTDGRAASRPSHRQGASGARGDPELPTLLRVYIDGPHG

VGKTTTSAQLMEALGPRDNIVYVPEPMTYWQVLGASETLTNIYNTQHRLDRGEISAGEAAVV

MTSAQITMSTPYAATDAVLAPHIGGEAVGPQAPPPALTLVFDRHPIASLLCYPAARYLMGSM

TPQAVLAFVALMPPTAPGTNLVLGVLPEAEHADRLARRQRPGERLDLAMLSAIRRVYDLLAN

TVRYLQRGGRWREDWGRLTGVAAATPRPDPEDGAGSLPRIEDTLFALFRVPELLAPNGDL

YHIFAWVLDVLADRLLPMHLFVLDYDQSPVGCRDALLRLTAGMIPTRVTTAGSIAEIRDLART

FAREVGGV (HSV-2 DNA pol nucleic acid sequence)

SEQ ID NO: 7

ATGTTTTGTGCCGCGGGCGGCCCGGCTTCCCCCGGGGGGAAGCCGGCGGCTCGGGC

GGCGTCTGGGTTTTTTGCCCCCCACAACCCCCGGGGAGCCACCCAGACGGCACCGCC

GCCTTGCCGCCGGCAGAACTTCTACAACCCCCACCTCGCTCAGACCGGAACGCAGCCA

AAGGCCCTCGGGCCGGCTCAGCGCCATACGTACTACAGCGAGTGCGACGAATTTCGAT

TTATCGCCCCGCGTTCGCTGGACGAGGACGCCCCCGCGGAGCAGCGCACCGGGGTCC

ACGACGGCCGCCTCCGGCGCGCCCCTAAGGTGTACTGCGGGGGGGACGAGCGCGAC

GTCCTCCGCGTGGGCCCGGAGGGCTTCTGGCCGCGTCGCTTGCGCCTGTGGGGCGGT

GCGGACCATGCCCCCGAGGGGTTCGACCCCACCGTCACCGTCTTCCACGTGTACGACA

TCCTGGAGCACGTGGAACACGCGTACAGCATGCGCGCCGCCCAGCTCCACGAGCGAT

TTATGGACGCCATCACGCCCGCCGGGACCGTCATCACGCTTCTGGGTCTGACCCCCGA

-continued

AGGCCATCGCGTCGCCGTTCACGTCTACGGCACGCGGCAGTACTTTTACATGAACAAG

GCGGAGGTGGATCGGCACCTGCAGTGCCGTGCCCCGCGCGATCTCTGCGAGCGCCTG

GCGGCGGCCCTGCGCGAGTCGCCGGGGGCGTCGTTCCGCGGCATCTCCGCGGACCA

CTTCGAGGCGGAGGTGGTGGAGCGCGCCGACGTGTACTATTACGAAACGCGCCCGAC

CCTGTACTACCGCGTCTTCGTGCGAAGCGGGCGCGCGCTGGCCTACCTGTGCGACAAC

TTTTGCCCCGCGATCAGGAAGTACGAGGGGGGCGTCGACGCCACCACCCGGTTTATCC

TGGACAACCCGGGGTTTGTCACCTTCGGCTGGTACCGCCTCAAGCCCGGCCGCGGGA

ACGCGCCGGCCCAACCGCGCCCCCCGACGGCGTTCGGAACCTCGAGCGACGTCGAGT

TTAACTGCACGGCGGACAACCTGGCCGTCGAGGGGGCCATGTGTGACCTGCCGGCCT

ACAAGCTCATGTGCTTCGATATCGAATGCAAGGCCGGGGGGGAGGACGAGCTGGCCTT

TCCGGTCGCGGAACGCCCGGAAGACCTCGTCATCCAGATCTCCTGTCTGCTCTACGAC

CTGTCCACCACCGCCCTCGAGCACATCCTCCTGTTTTCGCTCGGATCCTGCGACCTCCC

CGAGTCCCACCTCAGCGATCTCGCCTCCAGGGGCCTGCCGGCCCCCGTCGTCCTGGA

GTTTGACAGCGAATTCGAGATGCTGCTGGCCTTCATGACCTTCGTCAAGCAGTACGGCC

CCGAGTTCGTGACCGGGTACAACATCATCAACTTCGACTGGCCCTTCGTCCTGACCAAG

CTGACGGAGATCTACAAGGTCCCGCTCGACGGGTACGGGCGCATGAACGGCCGGGGT

GTGTTCCGCGTGTGGGACATCGGCCAGAGCCACTTTCAGAAGCGCAGCAAGATCAAGG

TGAACGGGATGGTGAACATCGACATGTACGGCATCATCACCGACAAGGTCAAACTCTCC

AGCTACAAGCTGAACGCCGTCGCCGAGGCCGTCTTGAAGGACAAGAAGAAGGATCTGA

GCTACCGCGACATCCCCGCCTACTACGCCTCCGGGCCCGCGCAGCGCGGGGTGATCG

GCGAGTATTGTGTGCAGGACTCGCTGCTGGTCGGGCAGCTGTTCTTCAAGTTTCTGCC

GCACCTGGAGCTTTCCGCCGTCGCGCGCCTGGCGGGCATCAACATCACCCGCACCATC

TACGACGGCCAGCAGATCCGCGTCTTCACGTGCCTCCTGCGCCTTGCGGGCCAGAAG

GGCTTCATCCTGCCGGACACCCAGGGGCGGTTTCGGGGCCTCGACAAGGAGGCGCCC

AAGCGCCCGGCCGTGCCTCGGGGGGAAGGGGAGCGGCCGGGGGACGGGAACGGGG

ACGAGGATAAGGACGACGACGAGGACGGGGACGAGGACGGGGACGAGCGCGAGGAG

GTCGCGCGCGAGACCGGGGGCCGGCACGTTGGGTACCAGGGGGCCCGGGTCCTCGA

CCCCACCTCCGGGTTTCACGTCGACCCCGTGGTGGTGTTTGACTTTGCCAGCCTGTAC

CCCAGCATCATCCAGGCCCACAACCTGTGCTTCAGTACGCTCTCCCTGCGGCCCGAGG

CCGTCGCGCACCTGGAGGCGGACCGGGACTACCTGGAGATCGAGGTGGGGGGCCGA

CGGCTGTTCTTCGTGAAGGCCCACGTACGCGAGAGCCTGCTGAGCATCCTGCTGCGCG

ACTGGCTGGCCATGCGAAAGCAGATCCGCTCGCGGATCCCCCAGAGCACCCCCGAGG

AGGCCGTCCTCCTCGACAAGCAACAGGCCGCCATCAAGGTGGTGTGCAACTCGGTGTA

CGGGTTCACCGGGGTGCAGCACGGTCTTCTGCCCTGCCTGCACGTGGCCGCCACCGT

GACGACCATCGGCCGCGAGATGCTCCTCGCGACGCGCGCGTACGTGCACGCGCGCTG

GGCGGAGTTCGATCAGCTGCTGGCCGACTTTCCGGAGGCGGCCGGCATGCGCGCCCC

CGGTCCGTACTCCATGCGCATCATCTACGGGGACACGGACTCCATTTTCGTTTTGTGCC

GCGGCCTCACGGCCGCGGGCCTGGTGGCCATGGGCGACAAGATGGCGAGCCACATCT

CGCGCGCGCTGTTCCTCCCCCCGATCAAGCTCGAGTGCGAAAAAACGTTCACCAAGCT

GCTGCTCATCGCCAAGAAAAAGTACATCGGCGTCATCTGCGGGGGCAAGATGCTCATC

AAGGGCGTGGATCTGGTGCGCAAAAACAACTGCGCGTTTATCAACCGCACCTCCAGGG

-continued

CCCTGGTCGACCTGCTGTTTTACGACGATACCGTATCCGGAGCGGCCGCCGCGTTAGC

CGAGCGCCCCGCAGAGGAGTGGCTGGCGCGACCCCTGCCCGAGGGACTGCAGGCGT

TCGGGGCCGTCCTCGTAGACGCCCATCGGCGCATCACCGACCCGGAGAGGGACATCC

AGGACTTTGTCCTCACCGCCGAACTGAGCAGACACCCGCGCGCGTACACCAACAAGCG

CCTGGCCCACCTGACGGTGTATTACAAGCTCATGGCCCGCCGCGCGCAGGTCCCGTCC

ATCAAGGACCGGATCCCGTACGTGATCGTGGCCCAGACCCGCGAGGTAGAGGAGACG

GTCGCGCGGCTGGCCGCCCTCCGCGAGCTAGACGCCGCCGCCCCAGGGGACGAGCC

CGCCCCCCCAGCGGCCCTGCCCTCCCCGGCCAAGCGCCCCCGGGAGACGCCGTCGC

ATGCCGACCCCCCGGGAGGCGCGTCCAAGCCCCGCAAGCTGCTGGTGTCCGAGCTGG

CGGAGGATCCCGGGTACGCCATCGCCCGGGGCGTTCCGCTCAACACGGACTATTACTT

CTCGCACCTGCTGGGGGCGGCCTGCGTGACGTTCAAGGCCCTGTTTGGAAATAACGCC

AAGATCACCGAGAGTCTGTTAAAGAGGTTTATTCCCGAGACGTGGCACCCCCCGGACG

ACGTGGCCGCGCGGCTCAGGGCCGCGGGGTTCGGGCCGGCGGGGGCCGGCGCTAC

GGCGGAGGAAACTCGTCGAATGTTGCATAGAGCCTTTGATACTCTAGCATGAGCCCCC

CGTCGAAGCTGATGTCCCGCATCTTGCAATAAA (HSV-2 DNA pol polypeptide sequence)

SEQ ID NO: 8

MFCAAGGPASPGGKPAARAASGFFAPHNPRGATQTAPPPCRRQNFYNPHLAQTGTQPKA

LGPAQRHTYYSECDEFRFIAPRSLDEDAPAEQRTGVHDGRLRRAPKVYCGGDERDVLRVG

PEGFWPRRLRLWGGADHAPEGFDPTVTVFHVYDILEHVEHAYSMRAAQLHERFMDAITPA

GTVITLLGLTPEGHRVAVHVYGTRQYFYMNKAEVDRHLQCRAPRDLCERLAAALRESPGAS

FRGISADHFEAEVVERADVYYYETRPTLYYRVFVRSGRALAYLCDNFCPAIRKYEGGVDATT

RFILDNPGFVTFGWYRLKPGRGNAPAQPRPPTAFGTSSDVEFNCTADNLAVEGAMCDLPA

YKLMCFDIECKAGGEDELAFPVAERPEDLVIQISCLLYDLSTTALEHILLFSLGSCDLPESHLS

DLASRGLPAPVVLEFDSEFEMLLAFMTFVKQYGPEFVTGYNIINFDWPFVLTKLTEIYKVPLD

GYGRMNGRGVFRVWDIGQSHFQKRSKIKVNGMVNIDMYGIITDKVKLSSYKLNAVAEAVLK

DKKKDLSYRDIPAYYASGPAQRGVIGEYCVQDSLLVGQLFFKFLPHLELSAVARLAGINITRTI

YDGQQIRVFTCLLRLAGQKGFILPDTQGRFRGLDKEAPKRPAVPRGEGERPGDGNGDEDK

DDDEDGDEDGDEREEVARETGGRHVGYQGARVLDPTSGFHVDPVVVFDFASLYPSIIQAH

NLCFSTLSLRPEAVAHLEADRDYLEIEVGGRRLFFVKAHVRESLLSILLRDWLAMRKQIRSRI

PQSTPEEAVLLDKQQAAIKVVCNSVYGFTGVQHGLLPCLHVAATVTTIGREMLLATRAYVHA

RWAEFDQLLADFPEAAGMRAPGPYSMRIIYGDTDSIFVLCRGLTAAGLVAMGDKMASHISR

ALFLPPIKLECEKTFTKLLLIAKKKYIGVICGGKMLIKGVDLVRKNNCAFINRTSRALVDLLFYD

DTVSGAAAALAERPAEEWLARPLPEGLQAFGAVLVDAHRRITDPERDIQDFVLTAELSRHPR

AYTNKRLAHLTVYYKLMARRAQVPSIKDRIPYVIVAQTREVEETVARLAALRELDAAAPGDEP

APPAALPSPAKRPRETPSHADPPGGASKPRKLLVSELAEDPGYAIARGVPLNTDYYFSHLLG

AACVTFKALFGNNAKITESLLKRFIPETWHPPDDVAARLRAAGFGPAGAGATAEETRRMLHR

AFDTLA

The invention claimed is:

1. A method of detecting a variant Herpes simplex virus 1 (HSV-1) thymidine kinase (TK) in a biofluid sample, comprising:

a. obtaining a biofluid sample from a patient; and b. detecting a variant HSV-1 TK 100C>T mutation present in the biofluid sample, by amplifying the variant HSV-1 TK gene, or fragment thereof using a set of primers to produce amplified nucleic acids, sequencing the amplified nucleic acids, and detecting said variant HSV-1 TK gene, or fragment thereof; or c. detecting a variant HSV-1 TK Q34* (Q34STOP mutation) present in the biofluid sample by performing mass spectrometry, a Western Blot, an Enzyme activity assay and/or an Enzyme-Linked Immunosorbent Assay (ELISA).

2. The method according to claim 1, further comprising detecting the presence of additional HSV-1 or HSV-2 TK or DNA polymerase (DNA pol) variants in the biological sample using:

a. a set of primers to produce amplified nucleic acids and sequencing the amplified nucleic acids, wherein the additional variants are selected from the group consisting of: HSV-2 TK 268C>T, HSV-1 TK 373C>T, HSV-1 TK 146T>G, HSV-1 TK 363G>A, HSV-1 TK 497T>A, HSV-2 TK 558G>T, HSV-2 TK 641A>G, HSV-1 TK 715T>C, HSV-2 TK 938T>C, HSV-1 TK 437_438insA, HSV-1 TK 169delC, HSV-1 TK 170delC, HSV-1 TK 171delC, HSV-1 TK 172delC, HSV-2 TK 458delC, HSV-2 TK 459delC, HSV-2 TK 460delC, HSV-2 TK 461delC, HSV-1 TK 881delC, HSV-2 TK 882dclC, HSV-1 TK 883delC, HSV-1 TK 884delC, HSV-1 TK 885delC, HSV-1 TK 110C>T, HSV-1 TK 205C>A, HSV-1 TK 1072A>C, HSV-1 1072A>T, HSV-1 TK 574G>A, HSV-1 TK_766C>T, HSV-2 TK 373G>A, HSV-2 TK 639A>C, HSV-2 TK 639A>T, HSV-2 TK 1094T>C, HSV-1 DNA Pol 2405T>G, HSV-1 DNA Pol 2500G>T, HSV-1 DNA Pol 2515A>G, HSV-1 DNA Pol 2892_2893insT, HSV-1 DNA Pol 2893_2894insT, HSV-1 DNA Pol 2894_2895insT, HSV-1 DNA Pol 2895_2896insT, HSV-1 DNA Pol 64G>A, HSV-1 DNA Pol 160A>G, HSV-1 DNA Pol 248A>C, HSV-1 DNA Pol 361G>A, HSV-1 DNA Pol 415G>A, HSV-1 DNA Pol 415G>C, HSV-1 DNA Pol 716C>T, HSV-1 DNA Pol 1255C>A, HSV-1 DNA Pol 2039A>C, HSV-1 DNA Pol 2042G>A, HSV-1 DNA Pol 2249A>C, HSV-1 DNA Pol 2548G>C, HSV-1 DNA Pol 2732G>A, HSV-1 DNA Pol 2741C>T, HSV-1 DNA Pol 2915C>T, HSV-1 DNA Pol 2954G>A, HSV-1 DNA Pol 2974G>A, HSV-1 DNA Pol 2977C>T, HSV-1 DNA Pol 3137A>C, HSV-1 DNA Pol 3343G>A, HSV-1 DNA Pol 3359A>C, HSV-1 DNA Pol 3505G>A, HSV-1 DNA Pol 3595C>A, HSV-2 DNA Pol 520G>T, HSV-2 DNA Pol 1339A>C, HSV-2 DNA Pol 1339A>T, HSV-2 DNA Pol 1481T>C, HSV-2 DNA Pol 2141A>G, HSV-2 DNA Pol 2281G>A, HSV-2 DNA Pol 2323C>T, HSV-2 DNA Pol 2325C>G, and HSV-2 DNA Pol 2326G>C; and/or b. mass spectrometry, a Western Blot, an Enzyme activity assay and/or ELISA, wherein the additional variants are selected from the group consisting of HSV-2 TK Q90* (Q90STOP), HSV-1 TK Q125* (Q25STOP), HSV-1 TK L49R, HSV-1 TK M1211, HSV-1 TK 1166N, HSV-2 TK Q186H, HSV-2 TK H214R, HSV-1 TK E146fs, HSV-1 TK Y239H, HSV-2 TK L313S, HSV-1 TK T183* (T183STOP), HSV-1 TK H58fs, HSV-1 TK M85* (M85STOP), HSV-2 TK P154fs, HSV-1 TK A294fs, HSV-1 TK P295fs, HSV-1 TK E296fs, HSV-1 DNA Pol L802R, HSV-1 DNA Pol A834S, HSV-1 DNA Pol T839A, HSV-1 DNA Pol F965_1966insF, HSV-1 DNA Pol 1966* (1966STOP), HSV-1 TK A37V, HSV-1 TK L69M, HSV-1 TK 1358L, HSV-1 TK A192T, HSV-1 TK R256W, HSV-2 TK A125T, HSV-2 TK E213D, HSV-2 TK L365P, HSV-1 DNA Pol G22R, HSV-1 DNA Pol T54A, HSV-1 DNA Pol D83A, HSV-1 DNA Pol G121S, HSV-1 DNA Pol G139R, HSV-1 DNA Pol S239L, HSV-1 DNA Pol L419I, HSV-1 DNA Pol E680A, HSV-1 DNA Pol R681Q, HSV-1 DNA Pol K750T, HSV-1 DNA Pol E850Q, HSV-1 DNA Pol S911N, HSV-1 DNA Pol S914L, HSV-1 DNA Pol A972V, HSV-1 DNA Pol G985E, HSV-1 DNA Pol E992K, HSV-1 DNA Pol R993C, HSV-1 DNA Pol N1046T, HSV-1 DNA Pol A1115T, HSV-1 DNA Pol E1120A, HSV-1 DNA Pol A1169T, HSV-1 DNA Pol P1199T, HSV-2 DNA Pol D174Y, HSV-2 DNA Pol M447L, HSV-2 DNA Pol M494T, HSV-2 DNA Pol H714R, HSV-2 DNA Pol E761K, HSV-2 DNA Pol R775C, HSV-2 DNA Pol R775W, and HSV-2 DNA Pol E776Q.

3. A method for treating an infection of an antiviral drug-resistant HSV-1 in a subject, comprising:

a. confirming the subject has an antiviral drug-resistant HSV-1 comprising a TK 100C>T (HSV 1), and/or Q34* (Q34STOP) mutation; and b. administering to said subject a drug comprising a foscarnet drug, a cidofovir drug, a docosanol drug; or a non-penciclovir that suppresses HSV and/or a non-acyclovir antiviral drug that suppresses HSV.

4. The method according to claim 1, wherein the HSV-1 TK mutation is relative to a reference wild-type HSV-1 TK sequence, and wherein the reference wild-type HSV-1 TK sequence comprises:

a. the nucleic acid sequence of SEQ ID NO: 1; and/or b. the polypeptide sequence of SEQ ID NO: 2.

5. The method according to claim 1, further comprising the step of recording on a suitable data carrier, the data obtained in the step of detecting the variant HSV-1 TK 100C>T and/or Q34* (Q34STOP) mutation.

6. A method for amplifying a variant HSV-1 thymidine kinase (TK) sequence, the method comprising:

amplifying by PCR a variant HSV-1 TK gene, or a fragment thereof comprising a 100C>T mutation from a biofluid sample obtained from a subject using a set of primers to produce amplified nucleic acids, and sequencing the amplified nucleic acids.

* * * * *